(12) United States Patent
Chrisitian et al.

(10) Patent No.: US 7,678,108 B2
(45) Date of Patent: Mar. 16, 2010

(54) LOOP ABLATION APPARATUS AND METHOD

(75) Inventors: Steven C. Chrisitian, Brooklyn Park, MN (US); David E. Francischelli, Brooklyn Park, MN (US); Adam A. Podbeliski, St. Paul, MN (US); Daniel Charles Haeg, Champlin, MN (US); Marie T. Steinbrink, Woodbury, MN (US); Roderick E. Briscoe, Rogers, MN (US); Tom P. Daigle, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 1320 days.

(21) Appl. No.: 11/143,128

(22) Filed: Jun. 2, 2005

(65) Prior Publication Data

US 2006/0009759 A1 Jan. 12, 2006

Related U.S. Application Data

(60) Provisional application No. 60/576,244, filed on Jun. 2, 2004, provisional application No. 60/581,138, filed on Jun. 18, 2004.

(51) Int. Cl.
*A61B 18/14* (2006.01)
(52) U.S. Cl. ...................................................... 606/41
(58) Field of Classification Search ............... 606/41, 606/50, 32, 34, 45, 48
See application file for complete search history.

(56) References Cited

U.S. PATENT DOCUMENTS

| 3,736,936 A | 6/1973 | Basiulis et al. |
| 3,807,403 A | 4/1974 | Stumpf et al. |
| 3,823,575 A | 7/1974 | Parel |
| 3,823,718 A | 7/1974 | Tromovitch |
| 3,827,436 A | 8/1974 | Stumpf et al. |
| 3,830,239 A | 8/1974 | Stumpf |

(Continued)

FOREIGN PATENT DOCUMENTS

WO WO 02/38064 5/2002

OTHER PUBLICATIONS

Chitwood, "Will C. Sealy, MD: The Father of Arrhythmia Surgery—The Story of the Fisherman with a Fast Pulse," Annals of Thoracic Surgery 58:1228-1239, 1994.

(Continued)

*Primary Examiner*—Lee S Cohen
(74) *Attorney, Agent, or Firm*—Mike Jaro; Jeffrey J. Hohenshell

(57) ABSTRACT

Embodiments of the invention provide an ablation apparatus for ablating target tissue adjacent pulmonary veins of a patient. The ablation apparatus can include a tube capable of being advanced around the pulmonary veins to form a loop. The tube can receive or include electrodes to ablate target tissue. Some embodiments provide a loop ablation device, which may include a cannula and two or more electrode rods carrying two or more bipolar electrodes. The electrode rods can be advanced through the distal ends toward the proximal ends of the loop and toward the target tissue. The bipolar electrodes can receive energy to ablate the target tissue. The bipolar electrodes may be surrounded by the liquid within the cannula while ablating the target tissue. The loop ablation device can further include a rotating grasping mechanism coupled to the electrode rods.

10 Claims, 71 Drawing Sheets

U.S. PATENT DOCUMENTS

| | | | | |
|---|---|---|---|---|
| 3,859,986 | A | 1/1975 | Okada et al. | |
| 3,862,627 | A | 1/1975 | Hans, Sr. | |
| 3,886,945 | A | 6/1975 | Stumpf et al. | |
| 3,907,339 | A | 9/1975 | Stumpf et al. | |
| 3,910,277 | A | 10/1975 | Zimmer | |
| 3,913,581 | A | 10/1975 | Ritson et al. | |
| 3,924,628 | A | 12/1975 | Droegemueller et al. | |
| 4,018,227 | A | 4/1977 | Wallach | |
| 4,022,215 | A | 5/1977 | Benson | |
| 4,061,135 | A | 12/1977 | Widran et al. | |
| 4,063,560 | A | 12/1977 | Thomas et al. | |
| 4,072,152 | A | 2/1978 | Linehan | |
| 4,082,096 | A | 4/1978 | Benson | |
| 4,207,897 | A | 6/1980 | Lloyd et al. | |
| 4,248,224 | A | 2/1981 | Jones | |
| 4,275,734 | A | 6/1981 | Mitchiner | |
| 4,278,090 | A | 7/1981 | van Gerven | |
| 4,377,168 | A | 3/1983 | Rzasa et al. | |
| 4,519,389 | A | 5/1985 | Gudkin et al. | |
| 4,522,212 | A * | 6/1985 | Gelinas et al. | 600/374 |
| 4,598,698 | A | 7/1986 | Siegmund | |
| 4,601,290 | A | 7/1986 | Effron et al. | |
| 4,664,110 | A | 5/1987 | Schanzlin | |
| 4,736,749 | A | 4/1988 | Lundback | |
| 4,779,611 | A | 10/1988 | Grooters et al. | |
| 4,802,475 | A | 2/1989 | Weshahy | |
| 4,815,470 | A | 3/1989 | Curtis et al. | |
| 4,834,090 | A * | 5/1989 | Moore | 606/148 |
| 4,872,346 | A | 10/1989 | Kelly-Fry et al. | |
| 4,916,922 | A | 4/1990 | Mullens | |
| 4,917,095 | A | 4/1990 | Fry et al. | |
| 4,936,281 | A | 6/1990 | Stasz | |
| 4,946,460 | A | 8/1990 | Merry et al. | |
| 5,013,312 | A | 5/1991 | Parins et al. | |
| 5,029,574 | A | 7/1991 | Shimamura et al. | |
| 5,044,165 | A | 9/1991 | Linner et al. | |
| 5,078,713 | A | 1/1992 | Varney | |
| 5,078,716 | A * | 1/1992 | Doll | 606/47 |
| 5,080,102 | A | 1/1992 | Dory | |
| 5,080,660 | A | 1/1992 | Buelina | |
| 5,100,388 | A | 3/1992 | Behl et al. | |
| 5,108,390 | A | 4/1992 | Potocky et al. | |
| 5,147,355 | A | 9/1992 | Friedman et al. | |
| 5,178,133 | A | 1/1993 | Pena | |
| 5,207,674 | A | 5/1993 | Hamilton | |
| 5,207,686 | A * | 5/1993 | Dolgin | 606/113 |
| 5,217,860 | A | 6/1993 | Fahy et al. | |
| 5,222,501 | A | 6/1993 | Ideker et al. | |
| 5,224,943 | A | 7/1993 | Goddard | |
| 5,228,923 | A | 7/1993 | Hed | |
| 5,231,995 | A | 8/1993 | Desai | |
| 5,232,516 | A | 8/1993 | Hed | |
| 5,254,116 | A | 10/1993 | Baust et al. | |
| 5,263,493 | A | 11/1993 | Avitall | |
| 5,269,291 | A | 12/1993 | Carter | |
| 5,275,595 | A | 1/1994 | Dobak, III | |
| 5,277,201 | A | 1/1994 | Stern | |
| 5,281,213 | A | 1/1994 | Milder et al. | |
| 5,281,215 | A | 1/1994 | Milder | |
| 5,295,484 | A | 3/1994 | Marcus et al. | |
| 5,309,896 | A | 5/1994 | Moll et al. | |
| 5,316,000 | A | 5/1994 | Chapelon et al. | |
| 5,317,878 | A | 6/1994 | Bradshaw et al. | |
| 5,318,525 | A | 6/1994 | West et al. | |
| 5,318,564 | A * | 6/1994 | Eggers | 606/47 |
| 5,322,520 | A | 6/1994 | Milder | |
| 5,323,781 | A | 6/1994 | Ideker et al. | |
| 5,324,255 | A | 6/1994 | Passafaro et al. | |
| 5,324,284 | A | 6/1994 | Imran | |
| 5,324,286 | A | 6/1994 | Fowler | |
| 5,334,181 | A | 8/1994 | Rubinsky et al. | |
| 5,334,193 | A | 8/1994 | Nardella | |
| 5,348,554 | A | 9/1994 | Imran et al. | |
| 5,353,783 | A | 10/1994 | Nakao et al. | |
| 5,354,258 | A | 10/1994 | Dory | |
| 5,361,752 | A | 11/1994 | Moll et al. | |
| 5,385,148 | A | 1/1995 | Lesh et al. | |
| 5,396,887 | A | 3/1995 | Imran | |
| 5,397,304 | A | 3/1995 | Truckai | |
| 5,400,770 | A | 3/1995 | Nakao et al. | |
| 5,400,783 | A | 3/1995 | Pomeranz et al. | |
| 5,403,309 | A | 4/1995 | Coleman et al. | |
| 5,403,311 | A | 4/1995 | Abele et al. | |
| 5,405,376 | A | 4/1995 | Mulier et al. | |
| 5,409,483 | A | 4/1995 | Campbell et al. | |
| 5,423,807 | A | 6/1995 | Milder | |
| 5,423,811 | A | 6/1995 | Imran et al. | |
| 5,427,119 | A | 6/1995 | Swartz et al. | |
| 5,431,649 | A | 7/1995 | Mulier et al. | |
| 5,433,708 | A | 7/1995 | Nichols et al. | |
| 5,435,308 | A | 7/1995 | Gallup et al. | |
| 5,437,651 | A | 8/1995 | Todd et al. | |
| 5,437,665 | A * | 8/1995 | Munro | 606/47 |
| 5,443,463 | A | 8/1995 | Stern et al. | |
| 5,443,470 | A | 8/1995 | Stern et al. | |
| 5,450,843 | A | 9/1995 | Moll et al. | |
| 5,452,582 | A | 9/1995 | Longsworth | |
| 5,452,733 | A | 9/1995 | Sterman et al. | |
| 5,454,370 | A * | 10/1995 | Avitall | 600/374 |
| 5,462,545 | A | 10/1995 | Wang et al. | |
| 5,465,717 | A | 11/1995 | Imran et al. | |
| 5,469,853 | A | 11/1995 | Law et al. | |
| 5,472,876 | A | 12/1995 | Fahy | |
| 5,478,309 | A | 12/1995 | Sweezer et al. | |
| 5,478,330 | A | 12/1995 | Imran et al. | |
| 5,486,193 | A | 1/1996 | Bourne et al. | |
| 5,487,385 | A | 1/1996 | Avitall | |
| 5,487,757 | A | 1/1996 | Truckai et al. | |
| 5,496,312 | A | 3/1996 | Klicek | |
| 5,497,774 | A | 3/1996 | Swartz et al. | |
| 5,498,248 | A | 3/1996 | Milder | |
| 5,500,012 | A | 3/1996 | Brucker et al. | |
| 5,505,730 | A | 4/1996 | Edwards | |
| 5,516,505 | A | 5/1996 | McDow | |
| 5,520,682 | A | 5/1996 | Baust et al. | |
| 5,522,870 | A | 6/1996 | Ben-Zion | |
| 5,536,267 | A | 7/1996 | Edwards et al. | |
| 5,545,195 | A | 8/1996 | Lennox et al. | |
| 5,545,200 | A | 8/1996 | West et al. | |
| 5,549,661 | A | 8/1996 | Kordis et al. | |
| 5,555,883 | A | 9/1996 | Avitall | |
| 5,558,671 | A | 9/1996 | Yates | |
| 5,560,362 | A | 10/1996 | Silwa, Jr. et al. | |
| 5,562,720 | A | 10/1996 | Stern et al. | |
| 5,569,241 | A | 10/1996 | Edwards | |
| 5,571,088 | A | 11/1996 | Lennox et al. | |
| 5,571,215 | A | 11/1996 | Sterman et al. | |
| 5,573,532 | A | 11/1996 | Chang et al. | |
| 5,575,766 | A | 11/1996 | Swartz et al. | |
| 5,575,788 | A | 11/1996 | Baker et al. | |
| 5,575,810 | A | 11/1996 | Swanson et al. | |
| 5,578,007 | A | 11/1996 | Imran | |
| 5,582,609 | A | 12/1996 | Swanson et al. | |
| 5,588,432 | A | 12/1996 | Crowley | |
| 5,590,657 | A | 1/1997 | Cain et al. | |
| 5,593,405 | A * | 1/1997 | Osypka | 606/15 |
| 5,595,183 | A | 1/1997 | Swanson et al. | |
| 5,607,462 | A | 3/1997 | Imran | |
| 5,617,854 | A | 4/1997 | Munsif | |
| 5,630,837 | A | 5/1997 | Crowley | |
| 5,637,090 | A | 6/1997 | McGee et al. | |
| 5,643,197 | A | 7/1997 | Brucker et al. | |
| 5,647,867 | A * | 7/1997 | Neuberger et al. | 606/15 |
| 5,656,029 | A | 8/1997 | Imran et al. | |

| | | | |
|---|---|---|---|
| 5,658,278 A | 8/1997 | Imran et al. | |
| 5,671,747 A | 9/1997 | Connor | |
| 5,673,695 A | 10/1997 | McGee et al. | |
| 5,676,662 A | 10/1997 | Fleischhacker et al. | |
| 5,676,692 A | 10/1997 | Sanghvi et al. | |
| 5,676,693 A | 10/1997 | Lafontaine | |
| 5,678,550 A | 10/1997 | Bassen et al. | |
| 5,680,860 A | 10/1997 | Imran | |
| 5,681,278 A | 10/1997 | Igo et al. | |
| 5,681,308 A | 10/1997 | Edwards et al. | |
| 5,687,723 A | 11/1997 | Avitall | |
| 5,687,737 A | 11/1997 | Branham et al. | |
| 5,688,267 A | 11/1997 | Panescu et al. | |
| 5,690,611 A | 11/1997 | Swartz et al. | |
| 5,697,536 A | 12/1997 | Eggers et al. | |
| 5,697,882 A | 12/1997 | Eggers et al. | |
| 5,697,925 A | 12/1997 | Taylor | |
| 5,697,927 A | 12/1997 | Imran et al. | |
| 5,697,928 A | 12/1997 | Walcott et al. | |
| 5,713,942 A | 2/1998 | Stern | |
| 5,716,389 A | 2/1998 | Walinsky et al. | |
| 5,718,241 A | 2/1998 | Ben-Haim et al. | |
| 5,718,701 A | 2/1998 | Shai et al. | |
| 5,720,775 A | 2/1998 | Lanard | |
| 5,722,402 A | 3/1998 | Swanson et al. | |
| 5,730,074 A | 3/1998 | Peter | |
| 5,730,127 A | 3/1998 | Avitall | |
| 5,730,704 A | 3/1998 | Avitall | |
| 5,733,280 A * | 3/1998 | Avitall | 606/23 |
| 5,735,280 A | 4/1998 | Sherman et al. | |
| 5,735,290 A | 4/1998 | Sterman et al. | |
| 5,738,683 A * | 4/1998 | Osypka | 606/47 |
| 5,755,760 A | 5/1998 | Maguire et al. | |
| 5,769,846 A | 6/1998 | Edwards et al. | |
| 5,782,828 A | 7/1998 | Chen et al. | |
| 5,785,706 A | 7/1998 | Bednarek | |
| 5,788,636 A | 8/1998 | Curley | |
| 5,792,140 A | 8/1998 | Tu et al. | |
| 5,797,960 A | 8/1998 | Stevens et al. | |
| 5,800,428 A | 9/1998 | Nelson et al. | |
| 5,800,482 A * | 9/1998 | Pomeranz et al. | 607/101 |
| 5,810,764 A * | 9/1998 | Eggers et al. | 604/23 |
| 5,810,802 A | 9/1998 | Panescu et al. | |
| 5,827,216 A | 10/1998 | Igo et al. | |
| 5,836,947 A | 11/1998 | Fleischman et al. | |
| 5,840,030 A | 11/1998 | Ferek-Petric et al. | |
| 5,844,349 A | 12/1998 | Oakley et al. | |
| 5,846,187 A | 12/1998 | Wells et al. | |
| 5,846,191 A | 12/1998 | Wells et al. | |
| 5,849,028 A | 12/1998 | Chen | |
| 5,871,523 A | 2/1999 | Fleischman et al. | |
| 5,871,525 A | 2/1999 | Edwards et al. | |
| 5,873,845 A | 2/1999 | Cline et al. | |
| 5,876,399 A | 3/1999 | Chia et al. | |
| 5,879,295 A | 3/1999 | Li et al. | |
| 5,879,296 A | 3/1999 | Ockuly et al. | |
| 5,881,732 A | 3/1999 | Sung et al. | |
| 5,882,346 A | 3/1999 | Pomeranz et al. | |
| 5,885,278 A | 3/1999 | Fleischman | |
| 5,893,848 A | 4/1999 | Negus et al. | |
| 5,895,417 A | 4/1999 | Pomeranz et al. | |
| 5,897,553 A | 4/1999 | Mulier | |
| 5,897,554 A | 4/1999 | Chia et al. | |
| 5,899,898 A | 5/1999 | Arless et al. | |
| 5,899,899 A | 5/1999 | Arless et al. | |
| 5,902,289 A | 5/1999 | Swartz et al. | |
| 5,904,711 A | 5/1999 | Flom et al. | |
| 5,906,580 A | 5/1999 | Kline-Schoder et al. | |
| 5,906,587 A | 5/1999 | Zimmon | |
| 5,906,606 A | 5/1999 | Chee et al. | |
| 5,908,029 A | 6/1999 | Knudson et al. | |
| 5,916,213 A | 6/1999 | Haissaguerre et al. | |
| 5,916,214 A | 6/1999 | Cosio et al. | |
| 5,921,924 A * | 7/1999 | Avitall | 600/374 |
| 5,921,982 A | 7/1999 | Lesh et al. | |
| 5,927,284 A | 7/1999 | Borst et al. | |
| 5,928,191 A | 7/1999 | Houser et al. | |
| 5,931,810 A | 8/1999 | Grabek | |
| 5,931,848 A | 8/1999 | Saadat | |
| 5,954,661 A | 9/1999 | Greenspon et al. | |
| 5,971,980 A | 10/1999 | Sherman | |
| 5,971,983 A | 10/1999 | Lesh | |
| 5,993,447 A | 11/1999 | Blewett et al. | |
| 6,007,499 A | 12/1999 | Martin et al. | |
| 6,012,457 A | 1/2000 | Lesh | |
| 6,016,811 A | 1/2000 | Knopp et al. | |
| 6,042,556 A | 3/2000 | Beach et al. | |
| 6,063,081 A | 5/2000 | Mulier | |
| 6,071,279 A | 6/2000 | Whayne et al. | |
| 6,088,894 A | 7/2000 | Oakley | |
| 6,093,185 A * | 7/2000 | Ellis et al. | 606/28 |
| 6,096,037 A | 8/2000 | Mulier | |
| 6,113,592 A | 9/2000 | Taylor | |
| 6,117,101 A | 9/2000 | Diederich et al. | |
| 6,120,496 A | 9/2000 | Whayne et al. | |
| 6,142,993 A | 11/2000 | Whayne et al. | |
| 6,142,994 A * | 11/2000 | Swanson et al. | 606/41 |
| 6,152,920 A | 11/2000 | Thompson et al. | |
| 6,161,543 A | 12/2000 | Cox et al. | |
| 6,165,174 A | 12/2000 | Jacobs et al. | |
| 6,217,528 B1 * | 4/2001 | Koblish et al. | 600/585 |
| 6,217,576 B1 | 4/2001 | Tu et al. | |
| 6,224,592 B1 | 5/2001 | Eggers et al. | |
| 6,231,518 B1 | 5/2001 | Grabek et al. | |
| 6,235,024 B1 | 5/2001 | Tu | |
| 6,237,605 B1 | 5/2001 | Vaska et al. | |
| 6,238,347 B1 | 5/2001 | Nix et al. | |
| 6,238,393 B1 | 5/2001 | Mulier | |
| 6,245,061 B1 | 6/2001 | Panescu et al. | |
| 6,245,064 B1 | 6/2001 | Lesh et al. | |
| 6,245,065 B1 | 6/2001 | Panescu et al. | |
| 6,251,092 B1 | 6/2001 | Qin et al. | |
| 6,251,128 B1 | 6/2001 | Knopp et al. | |
| 6,270,471 B1 | 8/2001 | Hechel et al. | |
| 6,277,117 B1 * | 8/2001 | Tetzlaff et al. | 606/48 |
| 6,293,943 B1 | 9/2001 | Panescu et al. | |
| 6,296,619 B1 | 10/2001 | Brisken et al. | |
| 6,302,880 B1 | 10/2001 | Schaer | |
| 6,311,692 B1 | 11/2001 | Vaska et al. | |
| 6,312,383 B1 | 11/2001 | Lizzi et al. | |
| 6,314,962 B1 | 11/2001 | Vaska et al. | |
| 6,314,963 B1 | 11/2001 | Vaska et al. | |
| 6,325,797 B1 | 12/2001 | Stewart et al. | |
| 6,328,736 B1 | 12/2001 | Mulier | |
| 6,330,473 B1 * | 12/2001 | Swanson et al. | 604/21 |
| 6,332,881 B1 | 12/2001 | Carner et al. | |
| 6,358,248 B1 | 3/2002 | Mulier | |
| 6,361,531 B1 | 3/2002 | Hissong | |
| 6,364,876 B1 | 4/2002 | Erb et al. | |
| 6,368,275 B1 | 4/2002 | Sliwa et al. | |
| 6,371,955 B1 | 4/2002 | Fuimaono et al. | |
| 6,383,151 B1 | 5/2002 | Diederich et al. | |
| 6,385,472 B1 | 5/2002 | Hall et al. | |
| 6,398,792 B1 | 6/2002 | O'Connor | |
| 6,402,746 B1 * | 6/2002 | Whayne et al. | 606/41 |
| 6,409,722 B1 | 6/2002 | Hoey | |
| 6,413,254 B1 | 7/2002 | Hissong et al. | |
| 6,419,648 B1 | 7/2002 | Vitek et al. | |
| 6,425,867 B1 | 7/2002 | Vaezy et al. | |
| 6,430,426 B2 | 8/2002 | Avitall | |
| 6,440,130 B1 | 8/2002 | Mulier | |
| 6,443,952 B1 | 9/2002 | Mulier | |
| 6,447,507 B1 | 9/2002 | Bednarek et al. | |
| 6,461,314 B1 | 10/2002 | Pant et al. | |
| 6,461,356 B1 | 10/2002 | Patterson | |
| 6,464,700 B1 | 10/2002 | Koblish et al. | |

| | | |
|---|---|---|
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,484,727 B1 | 11/2002 | Vaska et al. |
| 6,488,680 B1 | 12/2002 | Francischelli |
| 6,502,575 B1 | 1/2003 | Jacobs et al. |
| 6,514,250 B1 | 2/2003 | Jahns |
| 6,517,498 B1 * | 2/2003 | Burbank et al. ............. 600/564 |
| 6,527,767 B2 | 3/2003 | Wang et al. |
| 6,537,248 B2 | 3/2003 | Mulier |
| 6,558,382 B2 | 5/2003 | Jahns |
| 6,565,525 B1 | 5/2003 | Burbank et al. |
| 6,569,159 B1 * | 5/2003 | Edwards et al. ............... 606/41 |
| 6,584,360 B2 | 6/2003 | Francischelli |
| 6,585,732 B2 | 7/2003 | Mulier |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,622,731 B2 * | 9/2003 | Daniel et al. ................ 128/898 |
| 6,645,199 B1 | 11/2003 | Jenkins et al. |
| 6,648,883 B2 | 11/2003 | Francischelli |
| 6,656,175 B2 | 12/2003 | Francischelli |
| 6,663,627 B2 | 12/2003 | Francischelli |
| 6,692,450 B1 | 2/2004 | Coleman |
| 6,699,240 B2 | 3/2004 | Francischelli |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,773,433 B2 | 8/2004 | Stewart et al. |
| 6,776,780 B2 | 8/2004 | Mulier |
| 6,807,968 B2 | 10/2004 | Francischelli |
| 6,827,715 B2 | 12/2004 | Francischelli |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,916,318 B2 | 7/2005 | Francischelli |
| 6,936,046 B2 | 8/2005 | Hissong |
| 6,949,097 B2 | 9/2005 | Stewart et al. |
| 6,949,098 B2 | 9/2005 | Mulier |
| 6,960,205 B2 | 11/2005 | Jahns |
| 6,962,589 B2 | 11/2005 | Mulier |
| 6,974,454 B2 * | 12/2005 | Hooven ....................... 606/41 |
| 2002/0026188 A1 * | 2/2002 | Balbierz et al. ............... 606/41 |
| 2002/0035361 A1 * | 3/2002 | Houser et al. ................. 606/15 |
| 2002/0077623 A1 | 6/2002 | Sinofsky |
| 2003/0014049 A1 | 1/2003 | Koblish et al. |
| 2003/0045872 A1 | 3/2003 | Jacobs |
| 2003/0105453 A1 * | 6/2003 | Stewart et al. ............. 604/537 |
| 2003/0130653 A1 * | 7/2003 | Sixto et al. .................. 606/45 |
| 2003/0144656 A1 | 7/2003 | Ocel |
| 2003/0163129 A1 * | 8/2003 | Lee et al. ...................... 606/47 |
| 2003/0191462 A1 | 10/2003 | Jacobs |
| 2003/0216724 A1 | 11/2003 | Jahns |
| 2004/0015106 A1 | 1/2004 | Coleman |
| 2004/0015219 A1 | 1/2004 | Francischelli |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0143729 A1 | 6/2005 | Francischelli |
| 2005/0165392 A1 | 7/2005 | Francischelli |
| 2005/0209564 A1 | 9/2005 | Bonner |
| 2005/0267454 A1 | 12/2005 | Hissong |
| 2006/0009756 A1 | 1/2006 | Francischelli |
| 2006/0009759 A1 | 1/2006 | Christian |

OTHER PUBLICATIONS

Gallagher et al., "Cryosurgical Ablation of Accessory Atrioventrical Connections: A Method for Correction of the Pre-excitation Syndrome," Circulation 55(3): 471-479, 1977.

Sealy, "Direct Surgical Treatment of Arrhythmias: The Last Frontier in Surgical Cardiology," Chest 75(5): 536-537, 1979.

Sealy, "The Evolution of the Surgical Methods for Interruption of Right Free Wall Kent Bundles," The Annals of Thoracic Surgery 36(1): 29-36, 1983.

Guiraudon et al., "Surgical Repair of Wolff-Parkinson-White Syndrome: A New Closed-Heart Techique," The Annals of Thoracic Surgery 37(1): 67-71, 1984.

Klein et al., "Surgical Correction of the Wolff-Parkinson-White Syndrome in the Closed Heart Using Cryosurgery: A Simplified Approach," JACC 3(2): 405-409, 1984.

Randall et al., "Local Epicardial Chemical Ablation of Vagal Input to Sino-Atrial and Atrioventricular Regions of the Canine Heart," Journal of the Autonomic Nervous System 11:145-159, 1984.

Guiraudon et al., "Surgical Ablation of Posterior Septal Accessory Pathways in the Wolf-Parkinson-White Syndrome by a Closed Heart Technique," Journal Thoracic Cardiovascular Surgery 92:406-413, 1986.

Gallagher et al., "Surgical Treatment of Arrhythmias," The American Journal of Cardiology 61:27A-44A, 1988.

Mahomed et al., "Surgical Division of Wolff-Parkinson-White Pathways Utilizing the Closed-Heart Technique: A 2-Year Experience in 47 Patients," The Annals of Thoracic Surgery 45(5): 495-504, 1988.

Cox et al., Surgery for Atrial Fibrillation; Seminars in Thoracic and Cardiovascular Surgery, vol. 1, No. 1 (Jul. 1989) pp. 67-73.

Bredikis and Bredikis; Surgery of Tachyarrhythmia: Intracardiac Closed Heart Cryoablation; PACE, vol. 13, pp. 1980-1984.

McCarthy et al., "Combined Treatment of Mitral Regurgitation and Atrial Fibrillation with Valvuloplasty and the Maze Procedure," The American Journal of Cardiology 71: 483-486, 1993.

Yamauchi et al. "Use of Intraoperative Mapping to Optimize Surgical Ablation of Atrial Flutter," The Annals of Thoracic Surgery 56: 337-342, 1993.

Graffigna et al., "Surgical Treatment of Wolff-Parkinson-White Syndrome: Epicardial Approach Without the Use of Cardiopulmonary Bypass," Journal of Cardiac Surgery 8: 108-116, 1993.

Siefert et al., "Radiofrequency Maze Ablation for Atrial Fibrillation," Circulation 90(4): I-594.

Surgical treatment of atrial fibrillation: a review; Europace (2004) 5, S20-S29.

Elvan et al., "Radiofrequency Catheter Ablation of the Atria Reduces Inducibility and Duration of Atrial Fibrillation in Dog," Circulation 91: 2235-2244, 1995.

Cox et al., "Modification of the Maze Procedure for Atrial Flutter and Atrial Fibrillation. I. Rational and Surgical Results," The Journal of Thoracic Cardiovascular Surgery 110: 473-484, 1995.

Cox, "The Maze III Procedure for Treatment of Atrial Fibrillation," Sabiston DC, ed Atlas of Cardiothoracic Surgery, Philadelphia: WB Saunders: 460-475, 1994.

Sueda et al., "Simple Left Atrial Procedure for Chronic Atrial Fibrillation Associated with Mitral Valve Disease," The Annals of Thoracic Surgery 62(6): 1796-1800, 1996.

Tsui et al., "Maze 3 for Atrial Fibrillation: Two Cuts Too Few?" PACE 17: 2163-2166, 1994.

Kosakai et al., "Cox Maze Procedure for Chronic Atrial Fibrillation Associated with Mitral Valve Disease," The Journal of Thoracic Cardiovascular Surgery 108: 1049-1055, 1994.

Cox et al., "The Surgical Treatment of Atrial Fibrillation, IV Surgical Technique," *J. of Thorac Cardiovasc Surg*, 1991: 101: 584-593.

Nardella, "Radio Frequency Energy and Impedance Feedback," SPIE vol. 1068, Catheter Based Sensing and Imaging Technology (1989).

Avitall et. al., "A Thoracoscopic Approach to Ablate Atrial Fibrillation Via Linear Radiofrequency Lesion Generation on the Epicardium of Both Atria," PACE, Apr. 1996;19(Part II):626,#241.

Sie et al., "Radiofrequency Ablation of Atrial Fibrillation in Patients Undergoing Mitral Valve Surgery. First Experience," Circulation (Nov. 1996) 96:450,I-675,#3946.

Sie et al., "Radiofrequency Ablation of Atrial Fibrillation in Patients Undergoing Valve Surgery," Circulation (Nov. 1997) 84:I450,#2519.

Jais et al., "Catheter Ablation for Paroxysmal Atrial Fibrillation: High Success Rates with Ablation in the Left Atrium," Circulation (Nov. 1996) 94:I-675,#3946.

Cox, "Evolving Applications of the Maze Procedure for Atrial Fibrillation," Ann Thorac Surg, 1993;55:578-580.

Cox et al. "Five-Year Experience with the Maze Procedure for Atrial Fibrillation," Ann Thorac Surg, 1993; 56:814-824.

Avitall et al., "New Monitoring Criteria for Transmural Ablation of Atrial Tissues," Circulation, 1996;94(Supp 1):I-493, #2889.

Cox et al., "An 8½ Year Clinical Experience with Surgery for Atrial Fibrillation," Annals of Surgery, 1996;224(3):267-275.

Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279.

Haissaguerre et al., "Right and Left Atrial Radiofrequency Catheter Therapy of Paroxysmal Atrial Fibrillation," Journal of Cardiovascular Electrophysiology, 1996;7(12):1132-1144.

Haissaguerre et al., "Role of Catheter Ablation for Atrial Fibrillation," Current Opinion in Cardiology, 1997;12:18-23.

Kawaguchi et al., "Risks and Benefits of Combined Maze Procedure for Atrial Fibrillation Associated with Organic Heart Disease," JACC, 1996;28(4):985-990.

Cox, et al., "Perinodal cryosurgery for atrioventricular node reentry tachycardia in 23 patients," Journal of Thoracic and Cardiovascular Surgery, 99:Mar. 3, 1990, pp. 440-450.

Cox, "Anatomic-Electrophysiologic Basis for the Surgical Treatment of Refractory Ischemic Ventricular Tachycardia," Annals of Surgery, Aug. 1983; 198:2;119-129.

Williams, et al., "Left atrial isolation," J Thorac Cardiovasc Surg; 1980; 80: 373-380.

Scheinman, "Catheter-based Techniques for Cure of Cardiac Arrhythmias," Advances in Cardiovascular Medicine, 1996, ISSN 1075-5527, pp. 93-100.

Sueda et al., "Efficacy of a Simple Left Atrial Procedure for Chronic Atrial Fibrillation in Mitral Valve Operations," Ann Thorac Surg, 1997;63:1070-1075.

\* cited by examiner

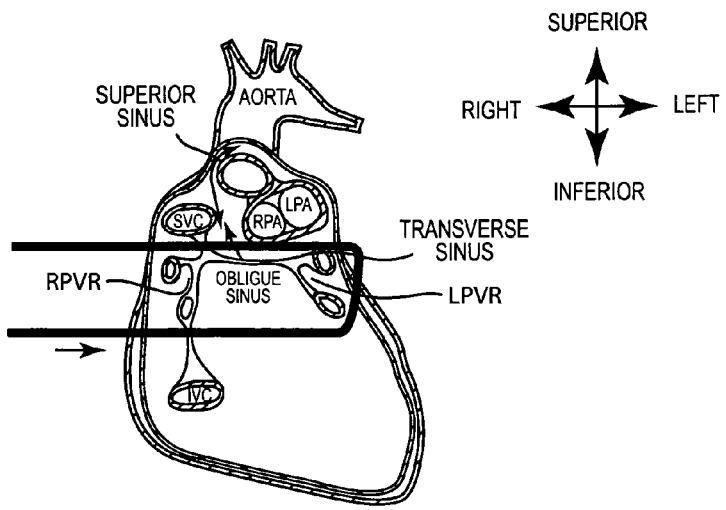
Fig. 2E
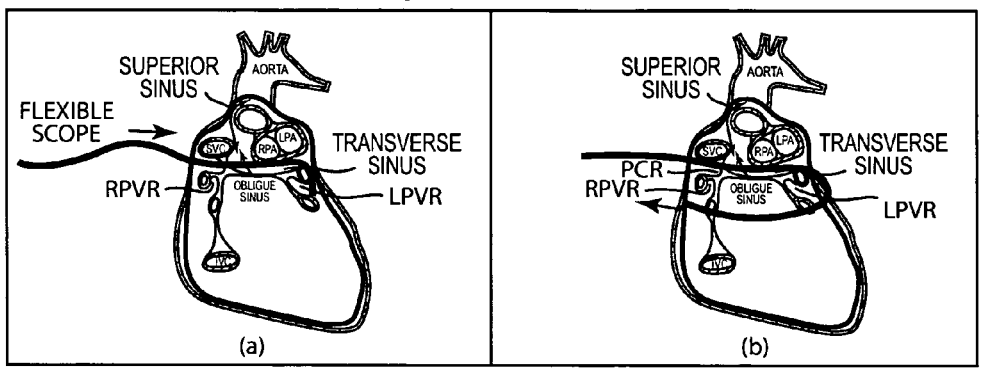
Fig. 2A  Fig. 2B
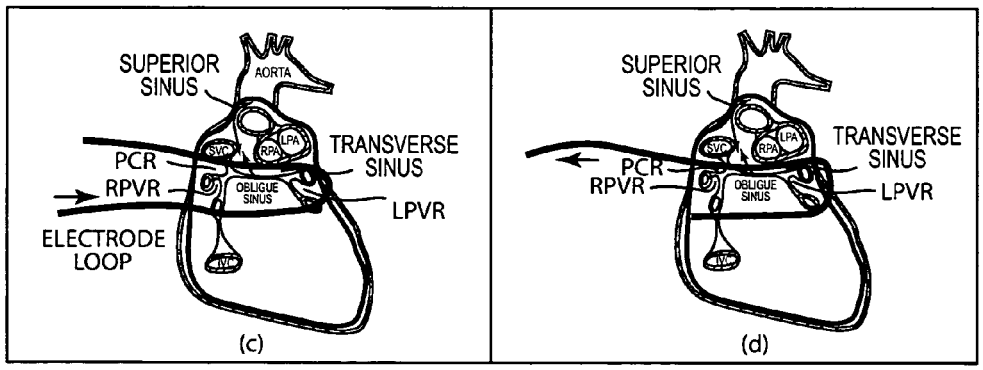
Fig. 2C  Fig. 2D

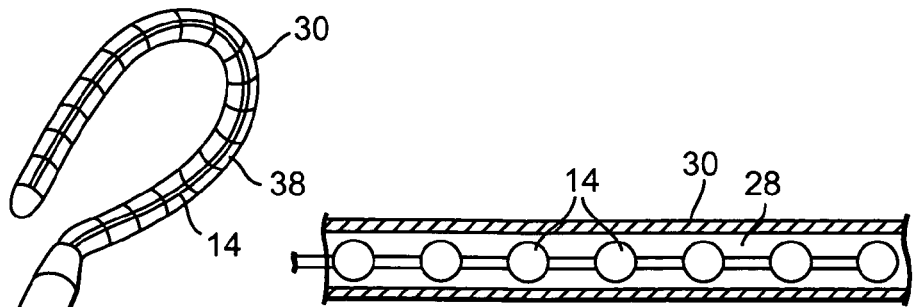
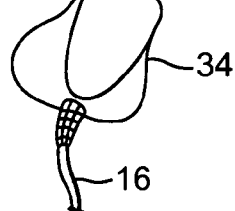
Fig. 6
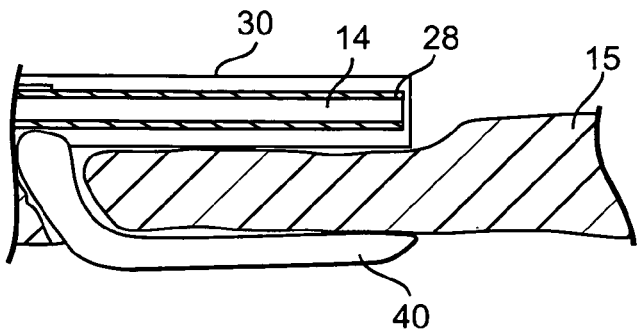
Fig. 7
Fig. 8
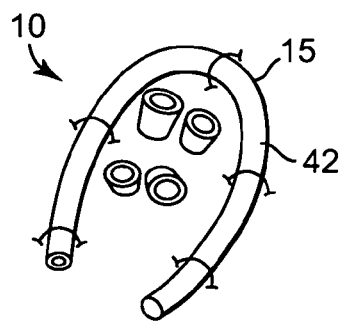
Fig. 9
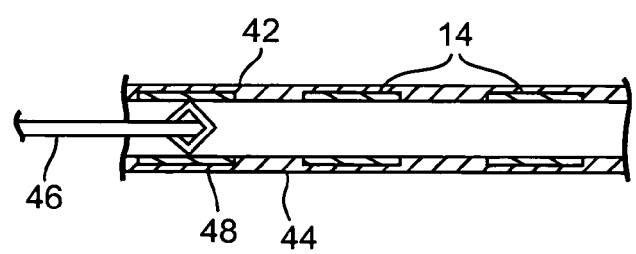
Fig. 10

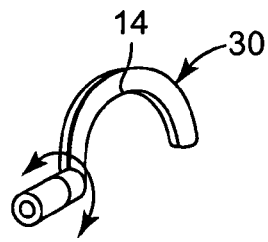
Fig. 11C
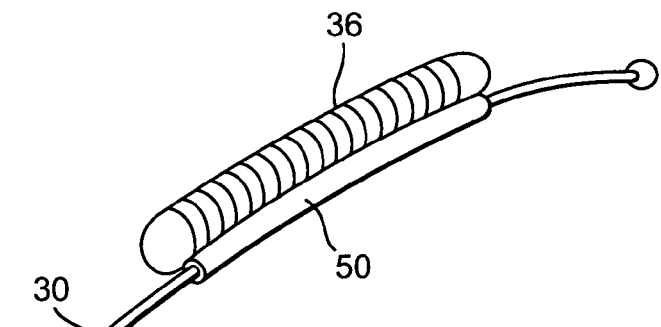
Fig. 11B
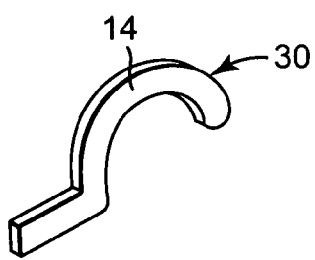
Fig. 11D
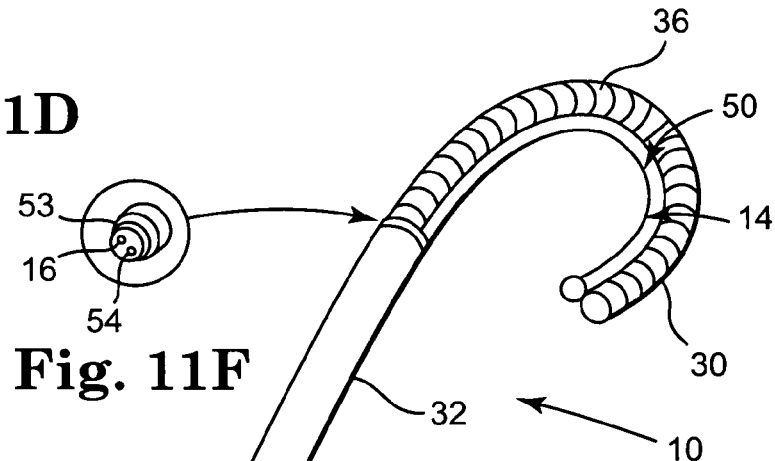
Fig. 11F
Fig. 11E
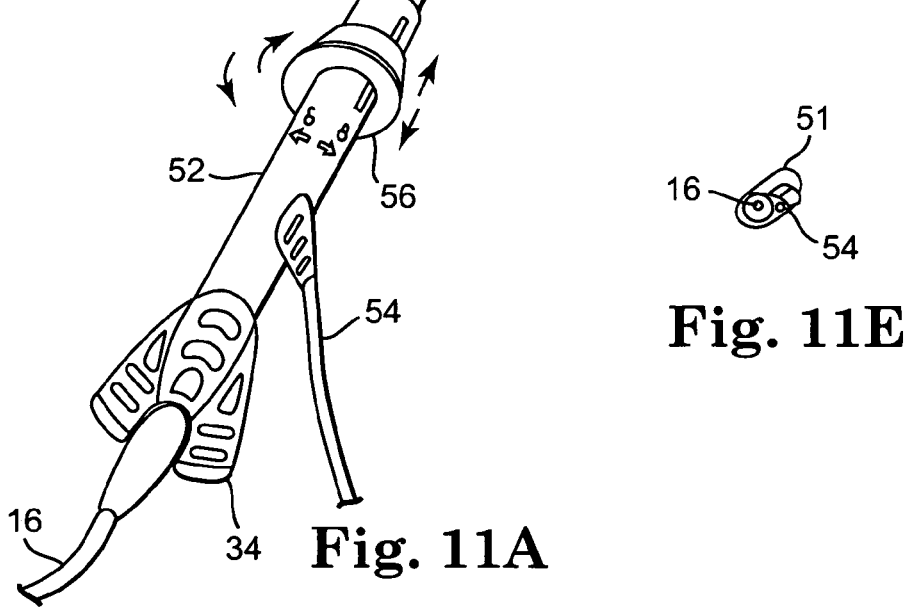
Fig. 11A

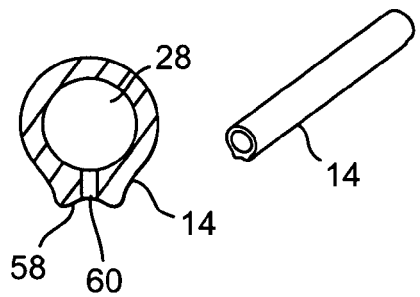
Fig. 12
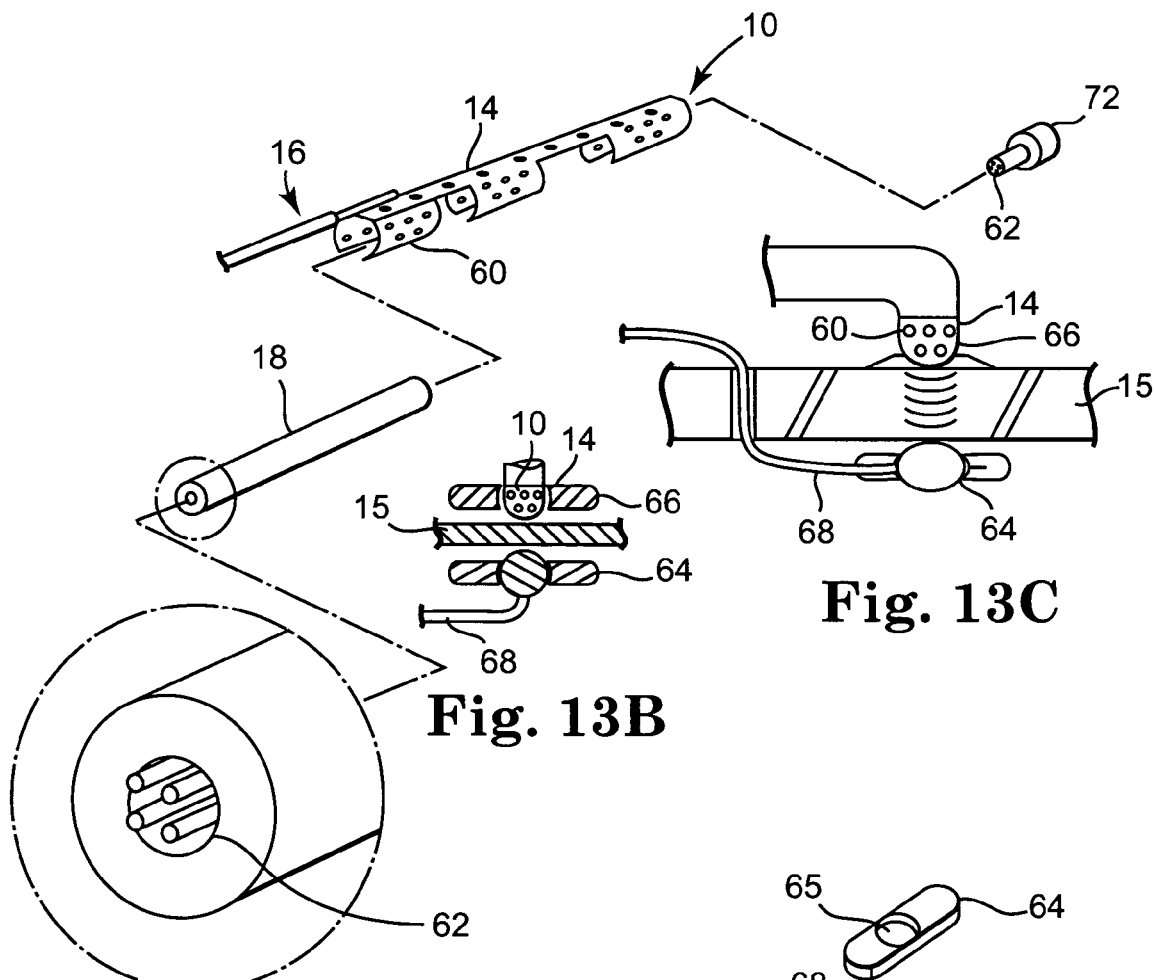
Fig. 13C
Fig. 13B
Fig. 13A
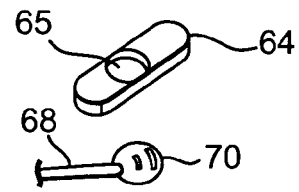
Fig. 13D

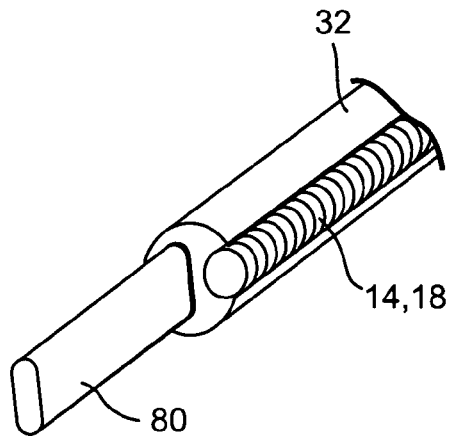
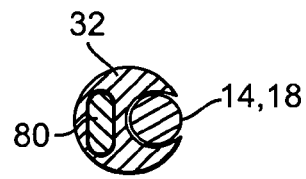
Fig. 18A        Fig. 18B
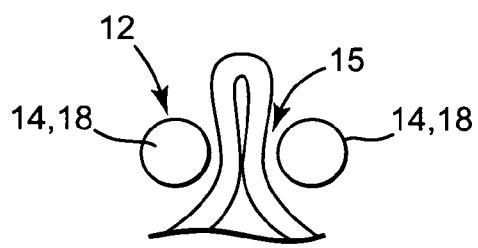
Fig. 19
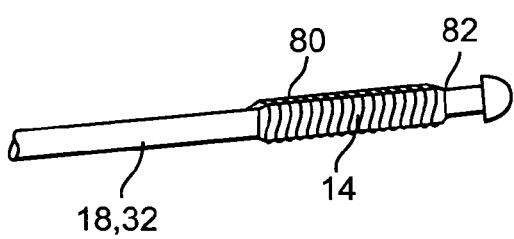
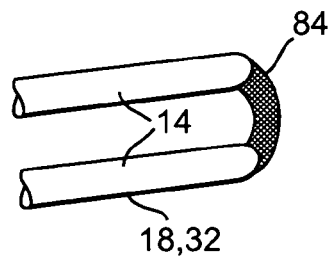
Fig. 20        Fig. 21

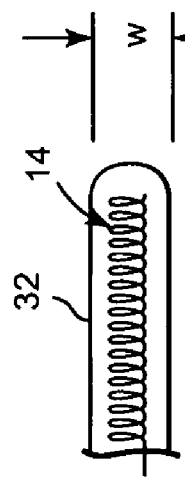
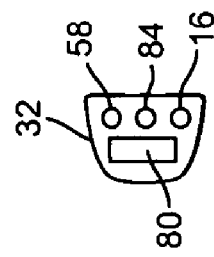
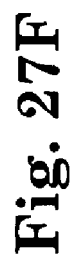
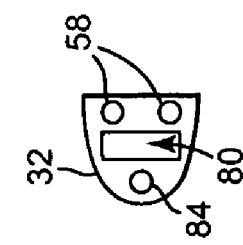
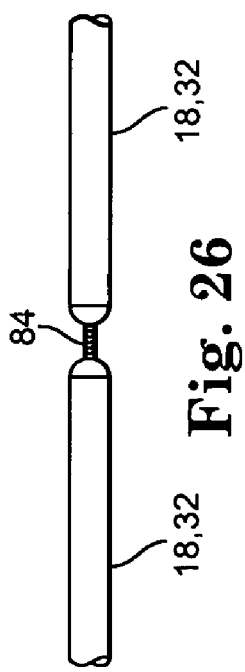
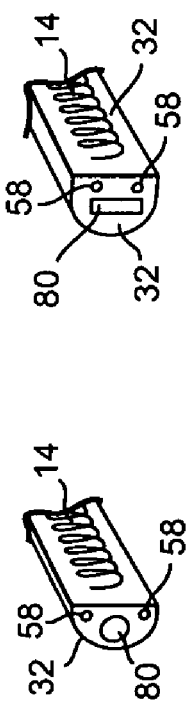

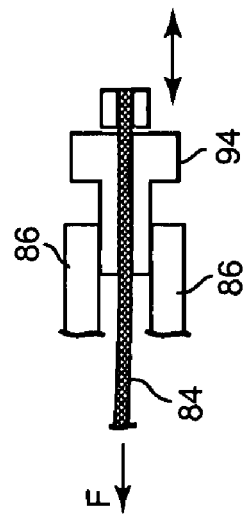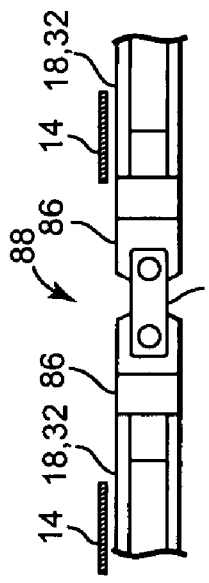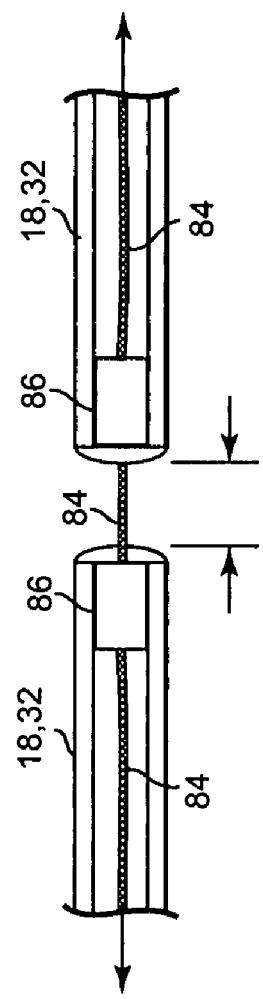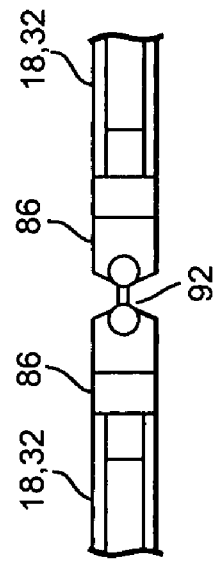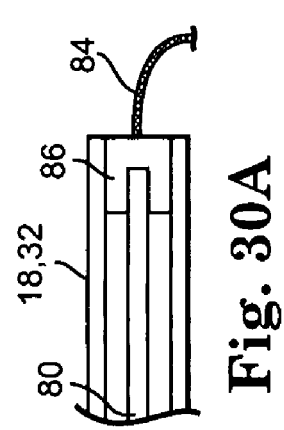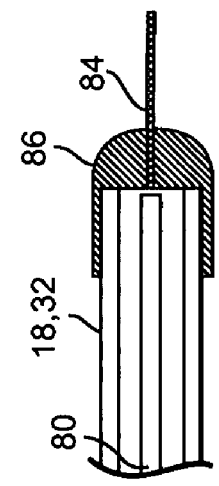

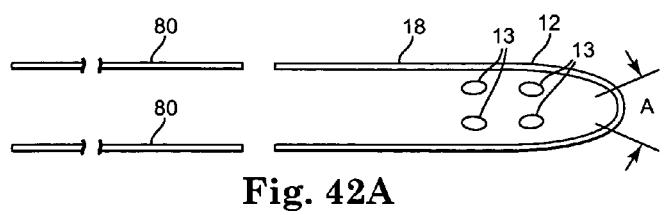
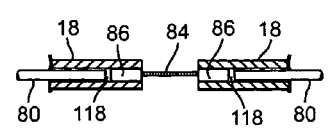
Fig. 42A    Fig. 42B
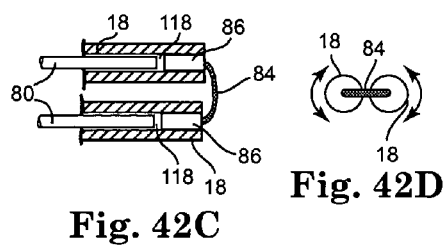
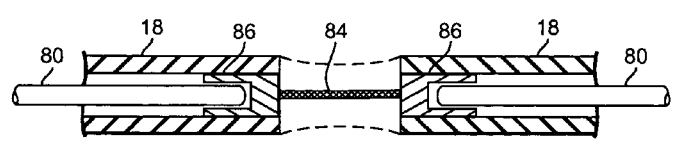
Fig. 42C    Fig. 42F
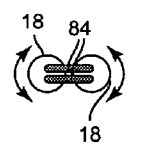 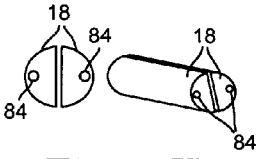
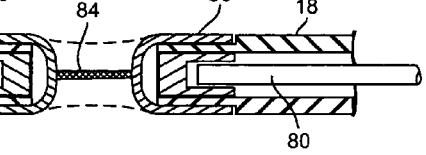
Fig. 42E    Fig. 42H    Fig. 42G

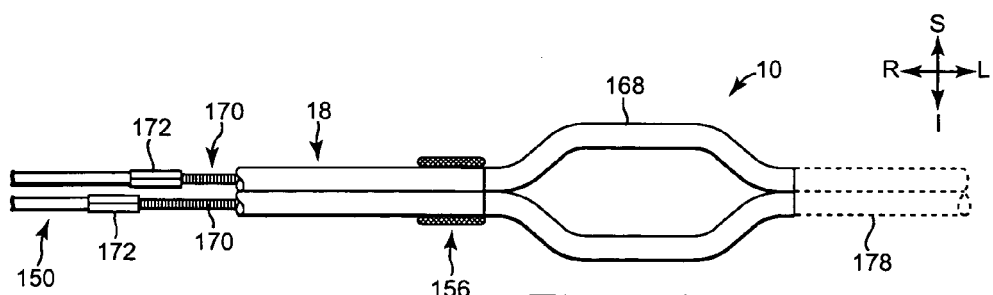
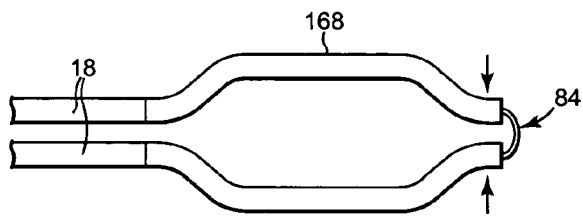 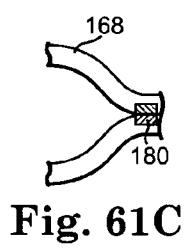 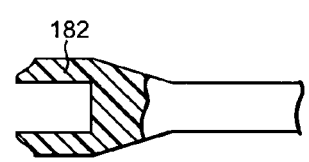
Fig. 61B    Fig. 61C    Fig. 61D
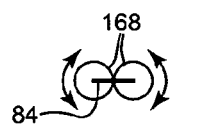
Fig. 61E
Fig. 61F
Fig. 61G

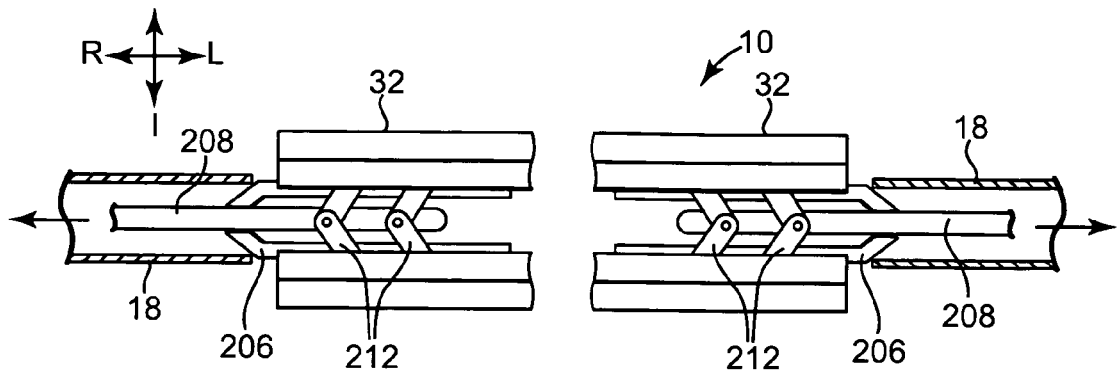
Fig. 65A
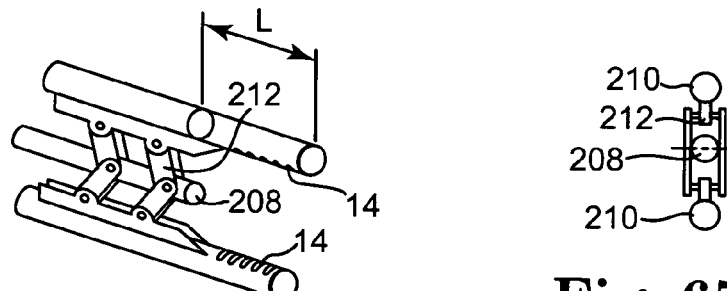
Fig. 65B
Fig. 65C
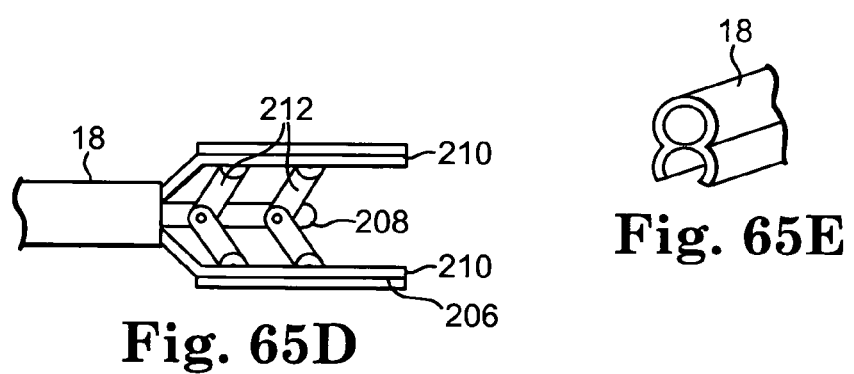
Fig. 65D
Fig. 65E

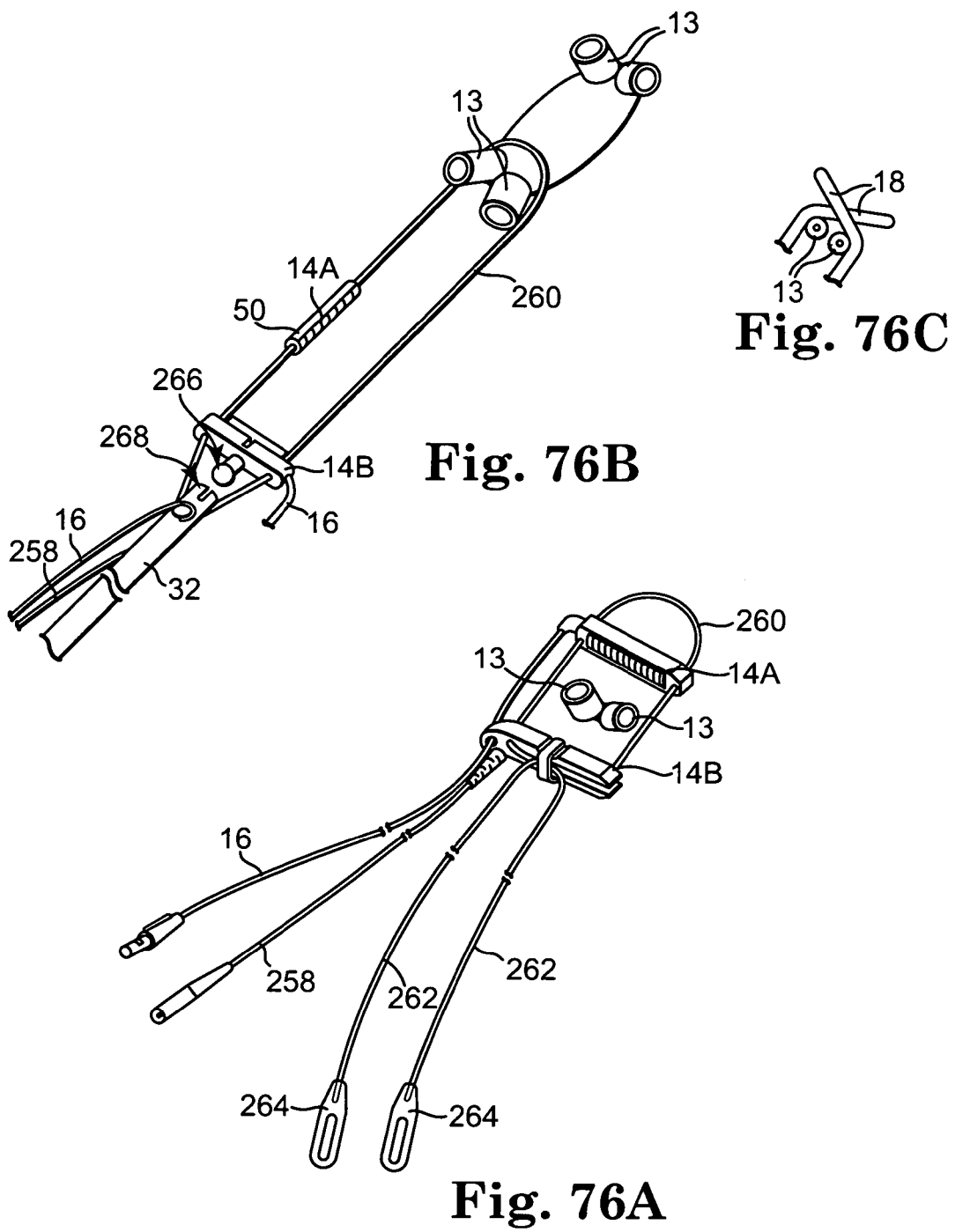
Fig. 76C
Fig. 76B
Fig. 76A
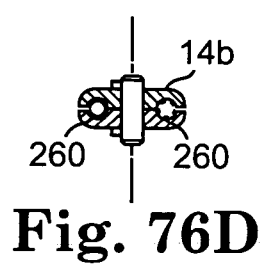
Fig. 76D
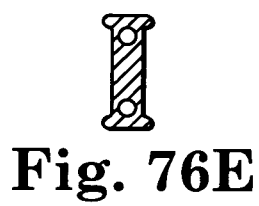
Fig. 76E

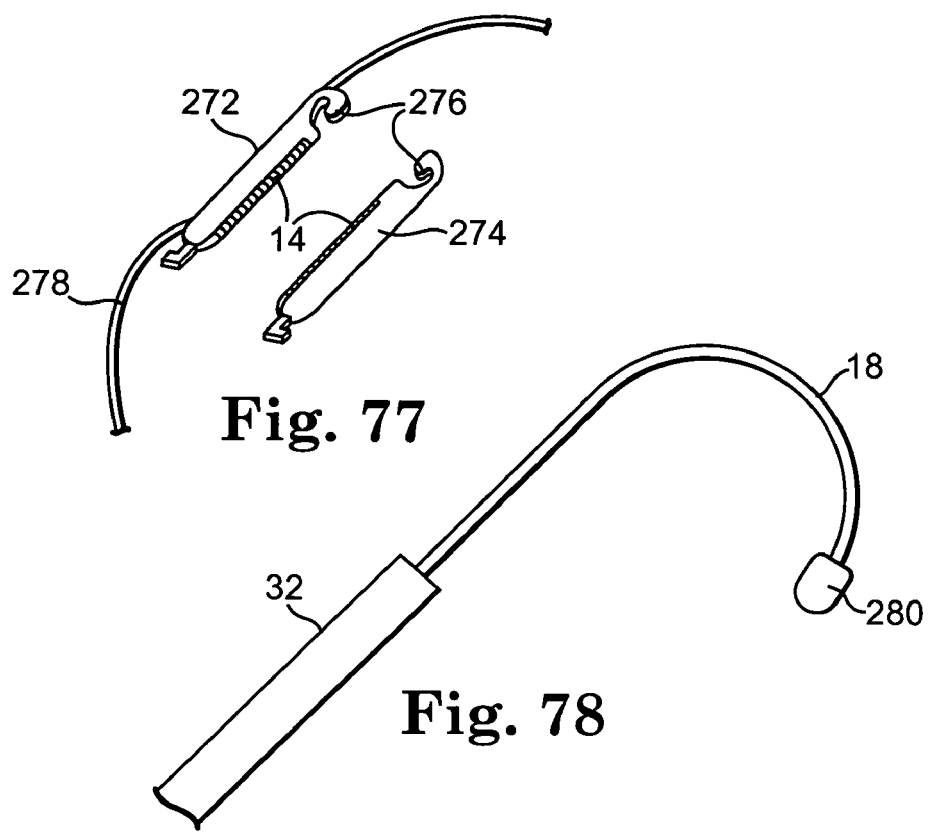
Fig. 77
Fig. 78
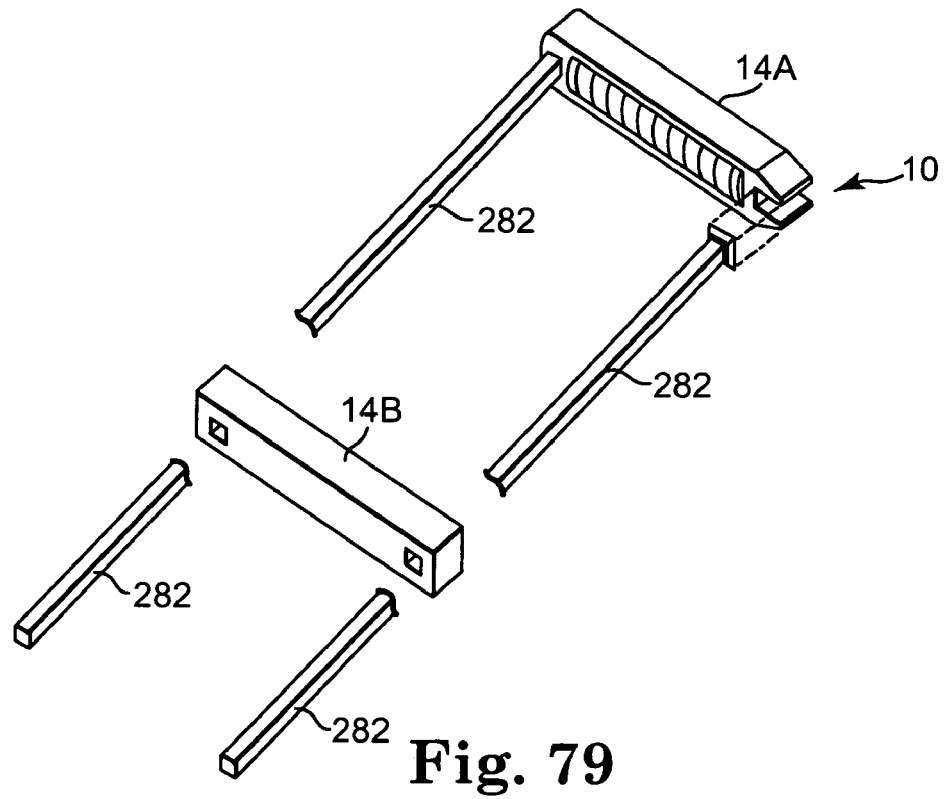
Fig. 79

LOOP ABLATION APPARATUS AND METHOD

RELATED APPLICATIONS

This application claims the benefit of the filing date of U.S. Provisional Patent Application No. 60/576,244 filed on Jun. 2, 2004, which is incorporated herein by reference in its entirety.

This application also claims the benefit of the filing date of U.S. Provisional Patent Application No. 60/581,138 filed on Jun. 18, 2004, which is incorporated herein by reference in its entirety.

BACKGROUND

Various types of electrocautery devices are used for ablating tissue. Typically, such devices include a conductive tip or blade, which serves as one electrode in an electrical circuit that is completed via a grounding electrode coupled to the patient. With sufficiently high levels of electrical energy between the two electrodes, heat is generated which is sufficient to denature proteins within the tissue and cause cell death.

By controlling the energy level, the amount of heat generated and the degree of tissue damage can also be controlled. High levels of voltage can actually cut and remove tissue (i.e., electrosurgery), while lower levels will simply create sufficient heat to cause cell damage, but leave the structure intact (i.e., ablation) and block electrical pathways within the tissue. Irrigation of the electrode(s) with saline or other conductive fluid can decrease the interface impedance, cool the tissue, and allow for a greater lesion depth.

The treatment of chronic atrial fibrillation (AF) requires the creation of numerous linear lesions that pass completely through the thickness of the tissue. Some electrophysiologists have created these lesions using the tip electrode of standard ablation catheters. These catheters were designed to create spot lesions, typically for ablation of specific structures or focal abnormalities. In order to make the linear lesions required to replicate the maze procedure, an electrophysiologist makes a series of focal lesions, and "connects the dots."

Manufacturers have therefore developed catheters that have a linear array of electrodes along a long axis (i.e., the Amazr, MECCA, and Revcelation catheters). The catheter and the electrodes are positioned in contact with the tissue. Energy is provided to the electrodes either individually or sequentially. Additionally, catheters which incorporate an electrode that can be energized and moved along a length of the catheter have been proposed.

Surgeons have also been able to create linear lesions on the heart using applications of the techniques discussed above. For example, Kottkamp et al. have used a handheld device that creates a series of spot or short (<1 cm) linear lesions. Other investigators have used long, linear unipolar probes to create somewhat longer lesions. Still others have used multi-electrode linear catheters, similar to those described above, to create a series of ablations that together form a linear lesion.

A bipolar system (in which the grounding electrode is in close proximity to the conductive tip) can create narrower and deeper lesions. The grounding electrode can be approximately the same dimension as the conductive tip, and both electrodes can create the lesion.

One bipolar ablation device has integrated the electrode into the jaws of a hemostat-like or forceps-like device. The device can clamp and ablate the tissue inbetween the jaws. In conjunction with a transmurality algorithm, the device creates transmural lesions. However, the device was designed to access the heart via a mid-line sternotomy. In order for the therapy to be considered as a stand-alone, access must be made less invasively. Simply placing the jaws onto an endoscopic handle has certain advantages, but there are significant limitations when trying to manipulate both jaws simultaneously through separate tissue spaces.

A microwave device has been developed that can loop around the posterior of the heart to encircle the pulmonary veins. A right thorocotomy is created at about the fourth intercostal space, and the pericardium is freed behind the superior vena cava and the inferior vena cava. A movable antenna slides within an integral sheath and discrete sections are ablated in series.

Loop devices do not all use microwave energy. Some investigators have used the radio frequency Cobra device, from Boston Scientific, to encircle the veins. Epicor has initiated clinical studies of a similar device that uses high frequency ultrasonic (HIFU) energy to generate heat within the tissue. Although easy to position within the patient, a significant limitation of these types of loop devices is the ability to reliably create a transmural lesion. Blood is constantly flowing within the heart chamber, and the blood acts as a heat sink to the energy being deposited within the tissue. Blood flow has the largest cooling effect on the tissue at an area of lowest heating. With epicardial systems, it is almost impossible to heat the endocardial layer sufficiently to create a permanent conduction block.

Other investigators have used a clamping device to compress the tissue between two ablative elements. The ablative elements are connected to rigid members that facilitate this compression. Although this bipolar arrangement is very effective at creating transmural lesions, it tends to be difficult to position within the patient. Manipulation of the rigid elements is problematic and can lead to tissue trauma.

SUMMARY OF THE INVENTION

Embodiments of the invention provide an ablation apparatus for ablating target tissue adjacent pulmonary veins of a patient. The ablation apparatus can include a tube capable of being advanced around the pulmonary veins to form a loop, and the loop including distal ends and proximal ends. The ablation apparatus can include carrier elements carrying bipolar electrodes. The carrier elements can be advanced through the distal ends toward the proximal ends of the loop and toward the target tissue. The proximal ends of the loop can be moved toward one another, and the carrier elements can be rotated so that the loop rolls substantially off of the pulmonary veins onto the target tissue. The bipolar electrodes can then receive energy to ablate the target tissue.

The invention includes a method of ablating target tissue of the left atrium of a patient. The method can include performing a right thoracotomy, providing a tube constructed of a porous and flexible material, and inserting the tube through the right thoracotomy under the superior vena cava into the transverse sinus of the pericardium until the tube loops around the left pulmonary veins. The method can also include visualizing the tube through the oblique sinus and pulling the tube until it extends below the inferior vena cava.

The invention also includes a method, which may include performing a right thoracotomy, providing a guide constructed of a flexible material, and inserting the guide member through the right thoracotomy under the superior vena cava into the transverse sinus of the pericardium until the guide loops around the left pulmonary veins. The method can also include visualizing the guide through the oblique sinus and pulling the guide until it extends below the inferior vena cava. Following insertion and positioning of the guide member, ablative elements, e.g., electrodes, may be slide over the guide member and positioned around the pulmonary veins. Once positioned, these ablative elements may be manipulated and used to ablate the atrial tissue around the pulmonary veins.

Some embodiments of the invention provide an ablation apparatus including an arm capable of being advanced around the pulmonary veins. The arm can include one or more electrodes and one or more tubes. One tube can receive electrodes and the same or another tube can provide a liquid to the target tissue. The one or more electrodes can receive energy to ablate the target tissue.

Some embodiments of the invention provide a loop ablation device for ablating target tissue adjacent pulmonary veins of a patient. The loop ablation device can include a cannula capable of being advanced around the pulmonary veins to form a loop, and the loop including distal ends and proximal ends. The cannula can receive a liquid. The loop ablation device can also include two or more electrode rods carrying two or more bipolar electrodes. The electrode rods can be advanced through the distal ends toward the proximal ends of the loop and toward the target tissue. The bipolar electrodes can receive energy to ablate the target tissue. The bipolar electrodes can be surrounded by the liquid within the cannula while ablating the target tissue. The loop ablation device can further include a rotating grasping mechanism coupled to the electrode rods. The rotating grasping mechanism can rotate the electrode rods within the cannula.

BRIEF DESCRIPTION OF THE DRAWINGS

FIGS. 2A-2E are cross-sectional views of a patient's heart and a schematic illustration of an ablation apparatus according to one embodiment of the invention.

FIG. 6 is a perspective view of an ablation apparatus according to one embodiment of the invention.

FIG. 7 is a side cross-sectional view of a string of pearls electrode arrangement.

FIG. 8 is a side cross-sectional view of a grounding electrode.

FIG. 9 is a perspective view of a pre-positioned conductive loop.

FIG. 10 is a side cross-sectional view of the pre-positioned conductive loop of FIG. 9.

FIGS. 11A-11F are perspective views of an ablation apparatus according to one embodiment of the invention.

FIG. 12 includes side and perspective views of a tube for use with an ablation apparatus according to one embodiment of the invention.

FIGS. 13A-13D are perspective and side cross-sectional views of an ablation apparatus according to one embodiment of the invention.

FIGS. 18A-18B are perspective and side cross-sectional views of an ablation apparatus according to one embodiment of the invention.

FIG. 19 is a schematic view of target tissue clamped by a loop.

FIG. 20 is a side view of an ablation apparatus according to one embodiment of the invention.

FIG. 21 is a side view of an ablation apparatus according to one embodiment of the invention.

FIG. 26 is a side view of an ablation apparatus according to one embodiment of the invention.

FIGS. 27A-27F are perspective, side, and bottom views of ablation apparatuses according to some embodiments of the invention.

FIGS. 30A-30F are side views of ablation apparatuses according to some embodiments of the invention.

FIGS. 42A-42H are side, cross-sectional, and perspective views of ablation apparatuses according to some embodiments of the invention.

FIGS. 61A-61G are side and cross-sectional views of ablation apparatuses according to some embodiments of the invention.

FIGS. 65A-65E are side, perspective, and cross-sectional views of an ablation apparatus according to one embodiment of the invention.

FIGS. 76A-76E are perspective, cross-sectional, and schematic views of ablation apparatuses according to some embodiments of the invention.

FIG. 77 is a perspective view of an ablation apparatus according to one embodiment of the invention.

FIG. 78 is a perspective view of an ablation apparatus according to one embodiment of the invention.

FIG. 79 is a perspective view of an ablation apparatus according to one embodiment of the invention.

DETAILED DESCRIPTION

Figure 1:
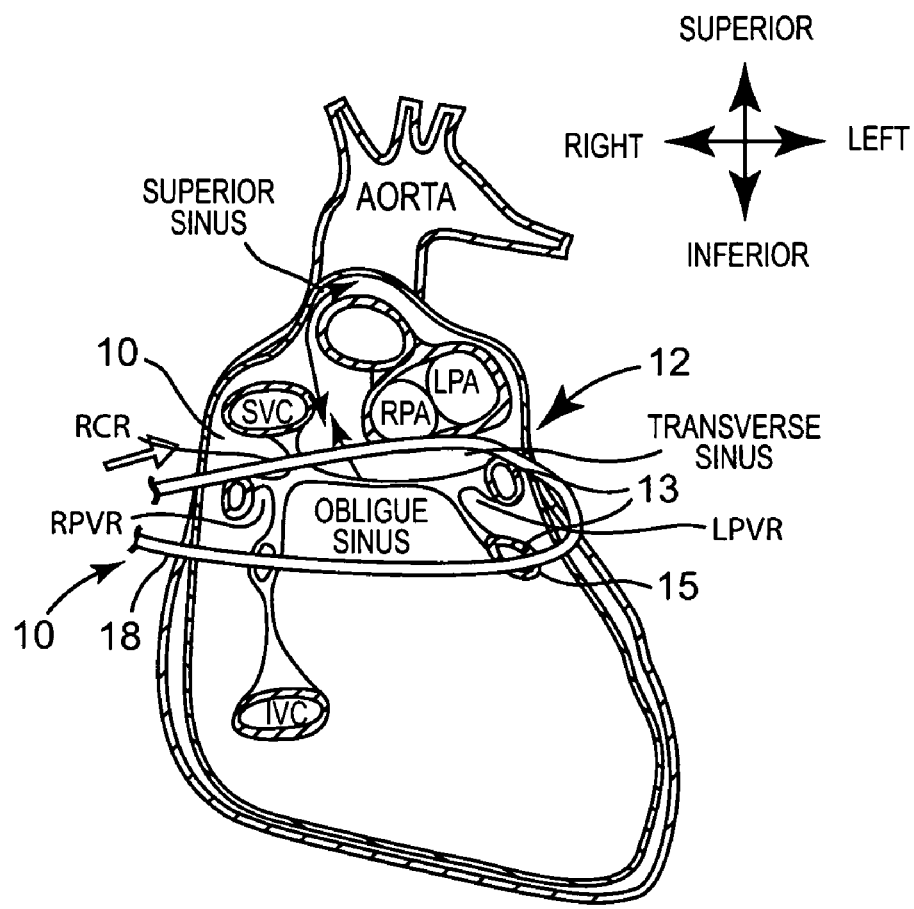
FIG. 1 is a cross-sectional view of a patient's heart and a schematic illustration of an ablation apparatus according to one embodiment of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect.

Some embodiments of the invention include a flexible loop of porous polymer with rigid electrodes to ablate tissue around the pulmonary veins of the heart. Some embodiments of the invention advance a flexible catheter or similar tubular device into the cardiac space and advance the distal end of the tube around the pulmonary arteries to form a loop. The two ends of the loop can then be used to insert a pair of carrier elements. The carrier elements can be advanced into or around the tube to a point where the electrodes are adjacent the tissue to be ablated. In one embodiment, the carrier elements have a cam-shaped section carrying the electrodes. The proximal ends of the tube can be brought together to clamp on the atrial tissue surrounding the pulmonary veins. The carrier elements can then be rotated 45 degrees to 180 degrees to allow the cam-shaped portions of the carrier elements to rotate to roll off the pulmonary veins onto the atrium bringing the electrodes to a position on the heart tissue. The cam shape also allows for ablation without complete occlusion of flow of blood through the pulmonary veins. The carrier elements can carry a conductor to the electrodes for application of radio frequency or any other suitable ablation energy from a power supply connected to the electrodes.

The tubes can be formed from a polymer suitable for insertion into the body and for contact with tissue and blood. The polymer can be a "weeping" polymer capable of allowing a liquid, such as a saline, to be pumped into the tube surrounding the carrier elements and the electrodes. The liquid can flow through the tube and conduct the ablation energy from the electrodes to the tissue of the atrium. Two electrodes in the tube can be configured as a bipolar ablation device for creating a linear lesion on the atrium adjacent to the pulmonary veins.

A variety of configurations of electrodes and carrier elements are available for insertion into the tube. The various configurations for surrounding the pulmonary veins can allow for linear ablation lesions to be formed through the tube walls.

Embodiments of the invention can also include a method and a device for threading the tube around the pulmonary veins. A feed catheter and retrieval catheter can be used. In one embodiment, the two catheters can be equipped with opposite and attracting magnets in the distal ends. As the catheters are brought in proximity to each other on the distal side of the target tissue, the magnets can attract each other, allowing the feed catheter to be retrieved back to the port or incision, and allowing the insertion of the carrier elements to place the electrodes in proximity to the target tissue. The use of cam-shaped electrodes or carrier elements and a liquid solution in the catheter to conduct the energy through the wall aids in creating lesions of a predetermined shape and length, while using a minimally invasive procedure. The retrieving catheter or the feed catheter can be aided in placement with steerable devices, such as memory alloy wired having a predetermined shape, for feeding around the pulmonary veins or other structures to meet with the other catheter. Alternatively, a steering device may be sufficient to feed the catheter around the pulmonary veins or other target tissue, without the need for a retrieving catheter.

In another embodiment, a rigid sleeve in the catheter can be used to feed a memory-shaped alloy guide to specific placements during the insertion procedure. As the sleeve is withdrawn or the memory-shaped alloy guide is expressed from the sleeve, different-shaped portions of the memory-shaped alloy guide can steer or feed through obstructions or obstacles. The guide can define a path around the pulmonary veins. An end of the guide can be retrieved by a tool from the incision or port in order to feed the catheter into position.

In some embodiments, the loop can place the electrodes in proximity to the tissue to be ablated. The clamping of the tissue between the carrier elements and the electrodes to create a bipolar ablation device can be performed by the tube holding the distal ends of the carrier elements in relation to each other. The proximal ends of the carrier elements can be clamped or otherwise fixed in relation to each other to create a clamping effect on the tissue surrounding the pulmonary veins. The electrodes can be connected to a power source and the saline, or other conductive liquid, can be introduced around the carrier elements and through the catheter to weep out around the electrodes and onto the target tissue. The electrodes can be fixed in the tube or can be drawn through the tube toward the tissue to be ablated. Once the tube is in place, the carrier elements with the electrodes can be introduced through both ends of the tube. The carrier elements can be shaped such that they can be rotated together to clamp sections of the left atrium to be ablated in a bipolar fashion, while leaving the remainder of the left atrium unclamped to allow pulmonary vein outflow. By intermittently clamping in successive locations across the left atrium, a full encirclement of the pulmonary veins can be achieved. The pre-positioning of the tube can allow the carrier elements to be placed in the proper location for pulmonary vein isolation, without direct continuous visual monitoring. Embodiments of the invention allow for right-sided only access to ablate both left and right sides of the left atrium near the pulmonary veins.

FIG. 1 illustrates a patient's heart, including the pulmonary veins 13, the oblique sinus, the transverse sinus, the superior sinus, the aorta, the superior vena cava, the right pulmonary artery, and the left pulmonary artery. FIG. 1 also schematically illustrates a tube 18 of an ablation apparatus 10 forming a loop 12 around the pulmonary veins 13 according to various embodiments of the invention.

FIGS. 2A-2E also illustrate a patient's heart, and a tube of an ablation apparatus at various stages of forming a loop around the pulmonary veins according to embodiments of the invention.

Figure 3:
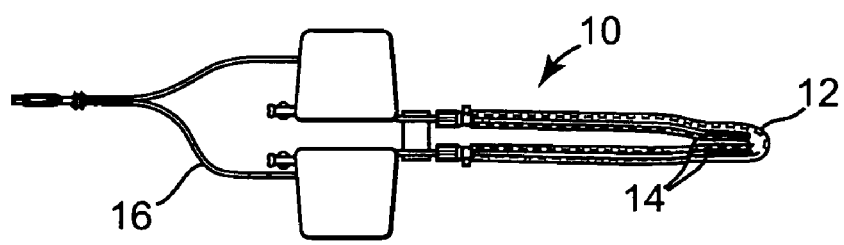
FIG. 3 is a side view of an ablation apparatus according to one embodiment of the invention.

FIG. 3 illustrates an ablation apparatus 10 according to one embodiment of the invention. The ablation apparatus 10 can include a loop 12, one or more electrodes 14, and a conductor 16.

Figure 4:
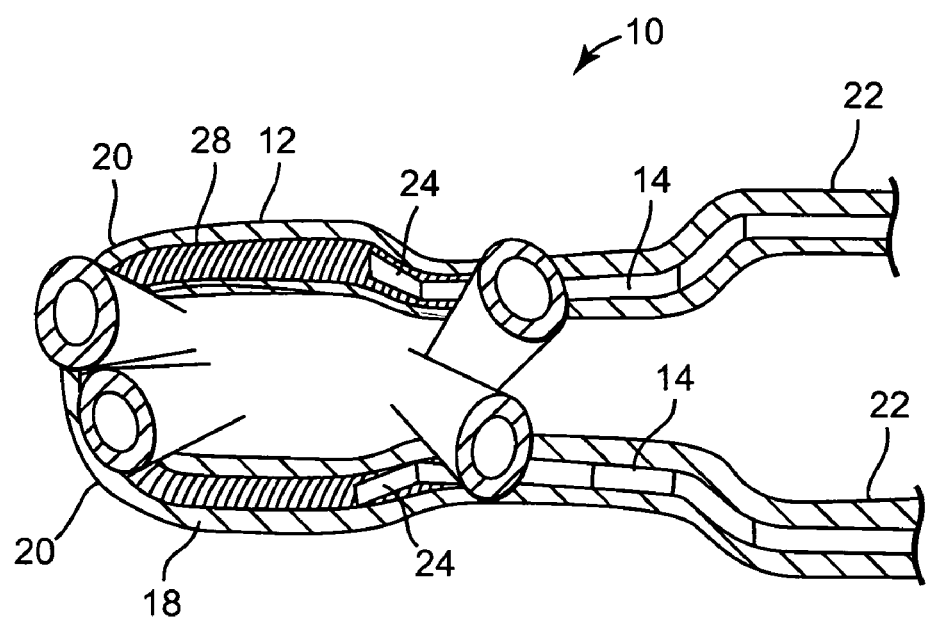
FIG. 4 is a cross-sectional schematic view of an ablation apparatus according to one embodiment of the invention.

FIG. 4 illustrates an ablation apparatus 10 according to another embodiment of the invention. The ablation apparatus 10 can include a loop 12 and electrodes 14. The loop 12 can be formed with a substantially-continuous tube 18. The tube 18 can be constructed of a porous polymer. The loop 12 can include distal ends 20 and proximal ends 22. The electrodes 14 can be coupled to one or more carrier elements 24. The carrier elements 24 can be inserted into the proximal ends 22 of the loop 12. The carrier elements 24 can be advanced from the proximal ends 22 of the loop 12 toward the distal ends 20 of the loop 12. The carrier elements can be advanced through the proximal ends 22 of the loop 12 toward the distal ends 20 of the loop 12 and toward the target tissue adjacent the pulmonary veins. The proximal ends 22 of the loop 12 can be moved toward one another and the carrier elements along with the electrodes 14 can be rotated so that the loop 12 rolls substantially off of the pulmonary veins onto the target tissue.

The electrodes 14 can be mono-electrodes or bipolar electrodes. For bipolar electrodes, two or more electrodes 14 can be advanced into the loop 12. The tube 18 of the loop 12 can also include an interior portion 28. The interior portion 28 can receive a liquid in order to surround the electrodes 14 with the liquid. In some embodiments, the liquid includes saline.

Figure 5:
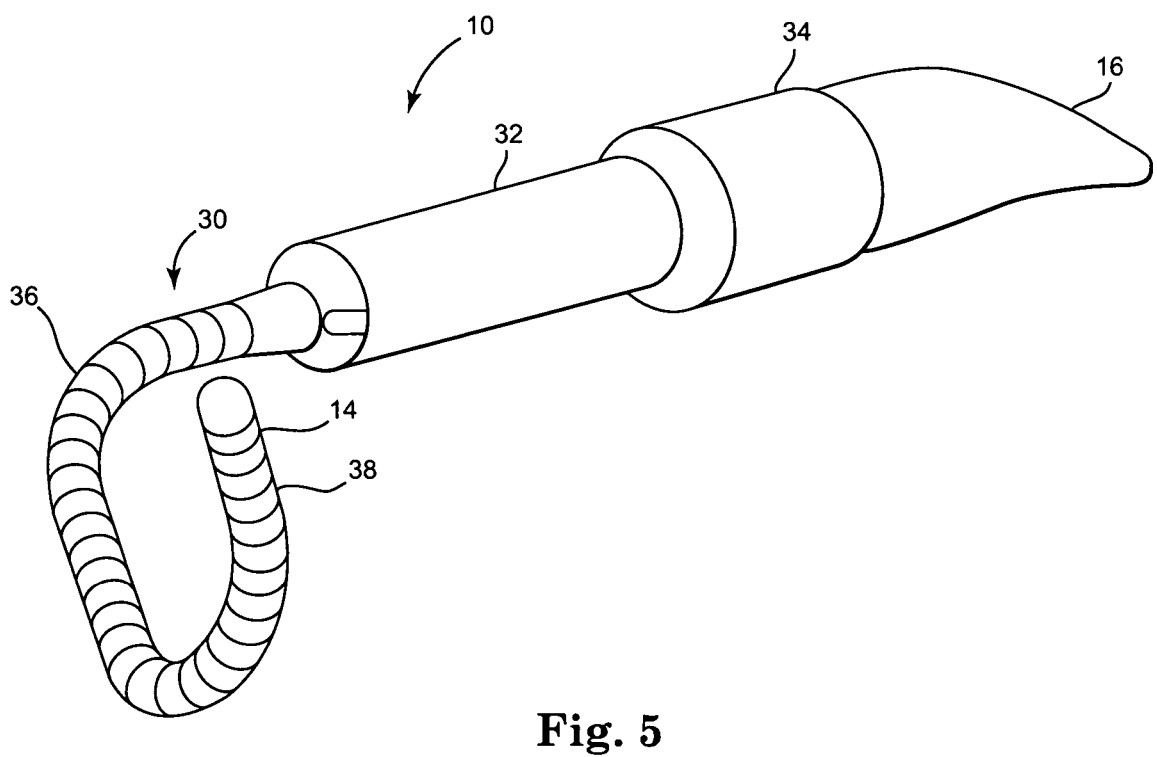
FIG. 5 is a perspective view of an ablation apparatus according to one embodiment of the invention.

FIG. 5 illustrates an ablation apparatus 10 according to another embodiment of the invention. The ablation apparatus 10 can include an arm 30, an insertion tool 32, and a knob 34. The arm 30 can include one or more articulating segments 36. The arm 34 can also include a conduit 38 including one or more electrodes 14. The insertion tool 32 can be coupled to the arm 30. The knob 34 can be coupled to the insertion tool 32. The knob 34 can be rotated in order to lock the articulating segments 36 into an ablating position. The electrodes 14 can receive energy to ablate the target tissue adjacent the articulating segments 36 in the ablating position. The ablation apparatus 10 can also include a conductor 16 coupled to the knob 34.

FIG. 6 illustrates another embodiment of the ablation apparatus 10 similar to the embodiment shown in FIG. 5. The ablation apparatus 10 of FIG. 6 can include an arm 30, an insertion tool 32, a knob 34, a conduit 38, electrodes 14, and a conductor 16. In some embodiments, the conduit 38 can include a string of electrodes 14, as shown in FIG. 7. The string of electrodes 14 can be surrounded by a liquid, such as saline. The saline can fill any voids between the string of electrodes 14. The articulating segments 36 of the arm 30 can be constructed of a weeping polymer which can allow the saline to weep through onto the target tissue. The saline can irrigate the target tissue in order to cool the target tissue after energy has been provided to the electrodes 14. In some embodiments, the ablation apparatus 10 can include a grounding member 40, as shown in FIG. 8. The grounding member can be inserted into target tissue 15 in order to ground the electrodes 14. FIG. 7 illustrates the string of electrodes 14 with the interior portion 28 that can receive saline to fill the void between the electrodes 14. FIG. 8 illustrates the arm 30 including the grounding member 40. FIG. 8 also illustrates the interior portion 28 of the arm 30 which can receive one or more electrodes 14.

FIG. 9 illustrates another embodiment of an ablation apparatus 10. The ablation apparatus 10 can include a pre-positioned conductive loop 42. The conductive loop 42 can include electrode tubing that can be attached to the target tissue 15 along an ablation path. As shown in FIG. 10, the conductive loop 42 can be constructed of a flexible encapsilant 44. Electrodes 14 can be embedded in the flexible encapsilant 44. FIG. 10 also illustrates a power and guide wire 46 that can be advanced through the conductive loop 42. The conductive loop 42 can also include energy transfer contacts 48. The energy transfer contacts 48 can be spaced along the length of the conductive loop 42. The energy transfer contacts 48 can provide an electrical connection between the power and guide wire 46 and the conductive loop 42. In some embodiments, as the power and guide wire 46 is advanced through the conductive loop 42, a positive stop mechanism in the insertion tool can stop the power and guide wire 46 at each energy transfer contact 48. At each stop, power can be transmitted to ablate the target tissue 15.

FIGS. 11A-11F illustrate another embodiment of the ablation apparatus 10. The ablation apparatus 10 can include an arm 30, an insertion tool 32, a knob 34, and a conduit 16. The arm 30 can also include articulating segments 36 with electrodes 14. The arm 30 can further include a lumen 50 that can move along the length of the arm 30. The knob 34 can rotate with respect to the insertion tool 32 in order to lock the articulating segments 36 in a particular position. The insertion tool 32 can also include a handle 52 and a liquid delivery tube 54 coupled to the handle 52. The handle 52 can also include a lock 56. The lock 56 can be rotated and/or translated in order to prevent the lumen 50 from moving along the length of the arm 30. FIG. 11B illustrates the arm 30, the articulating segments 36, and the lumen 50. The articulating segments 36 can move with the lumen 50 along the length of the arm 30. FIG. 11C illustrates another embodiment of an arm 30 including electrodes 14. The arm 30 can rotate about a longitudinal axis. FIG. 11D illustrates another embodiment of an arm 30 including electrodes 14 with the arm 30 in a fixed position. The ablation apparatus 10 of FIG. 11A can include a steerable electrode. The ablation apparatus 10 can include a steerable link 51, as shown in FIG. 11E. The ablation apparatus 10 can also include a telescoping mechanism 53, as shown in FIG. 11F. The telescoping mechanism 53 can allow the arm 30 to extend and/or retract with respect to the insertion tool 32. The telescoping mechanism 53 can include the conductor 16 and the liquid delivery tube 54 in order to provide energy and liquid to the arm 30. Similarly, FIG. 11E illustrates that the steereable link 51 can include the conductor 16 and the liquid delivery tube 54 in order to provide energy and liquid to the arm 30 as the arm 30 is positioned using the steerable link 51. In some embodiments, the insertion tool 32 can be constructed of rigid SS tubing. In some embodiments, the lumen 50 can house a cable for the conductor 16. In some embodiments, the lumen 50 can include a light tube in order to illuminate the target tissue 15 as the arm 30 is positioned.

FIG. 12 illustrates an electrode 14 including an interior portion 28, a saline channel 58, and a saline orifice 60. The electrode 14 of FIG. 12 can be used in conjunction with any suitable ablation apparatus 10. Saline can be provided through the interior portion 28 of the electrode 14 and can flow through the saline channel 58 and the saline orifice 60 onto the target tissue 15.

FIG. 13A illustrates an ablation apparatus 10 according to another embodiment of the invention. The ablation apparatus 10 can include an external electrode 14, a conductor 16, a tube 18, and a nose 72. The tube 18 can be constructed of a porous polymer. The tube 18 can surround steering wires 62 and/or the conductor 16. The electrode 14 can be constructed of a flexible metallic material in order to be crimped onto the porous polymer of the tube 18. The nose 72 can receive the ends of steering wires 62 and can be coupled to an end of the tube 18. The external electrode 14 can also include saline orifices 60 in order to provide saline to the target tissue 15. In some embodiments, the nose 72 can also include a magnet 64 that can be used in conjunction with a retrieval catheter. As shown in FIGS. 13B and 13C, the retrieval catheter can include a tether 68 coupled to a magnet 64. The magnet 64 of the retrieval catheter can be positioned adjacent to a magnet 66 in the nose 72 of the ablation apparatus 10 in order to position the external electrodes 14 in relation to the target tissue 15. FIG. 13D illustrates one embodiment of a magnet 64 including an aperture 65 which can receive a metallic ball 70 coupled to the tether 68 of the retrieval catheter. The magnet 64 of FIG. 13D can be coupled in any suitable manner to the electrode 14 and/or the tube 18. The ball 70 can, in some embodiments, be a magnetic electrode. In some embodiments, the tether 68 of the retrieval catheter can be positioned through the target tissue 15 on an interior wall of the target tissue 15. The magnet 64 of the electrode 14 and the magnetic electrode in the ball 70 can keep the electrode aligned with the target tissue 15 with a magnetic field.

Figure 14A:
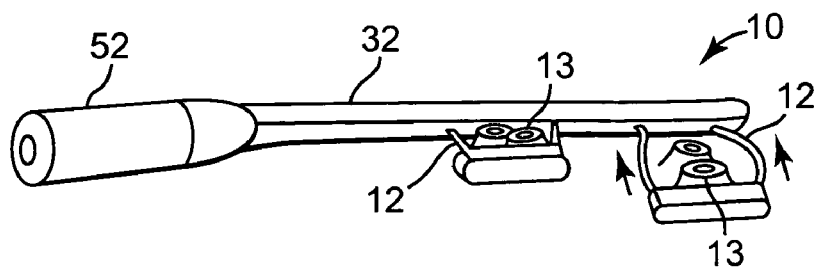
FIGS. 14A-14E are perspective and side cross-sectional views of ablation apparatuses according to some embodiments of the invention.
Figure 14B:
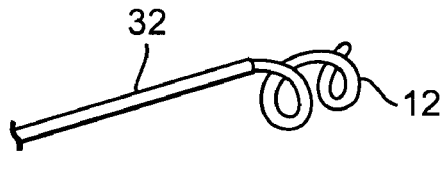
Figure 14C:
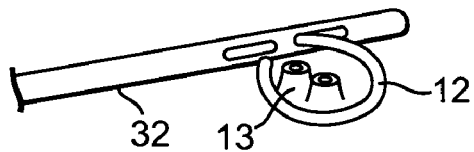
Figure 14D:
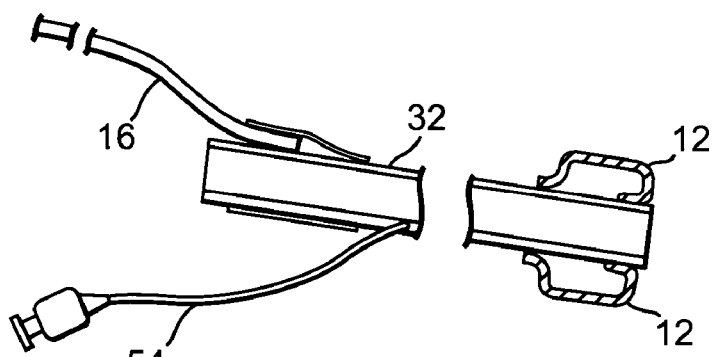
Figure 14E:
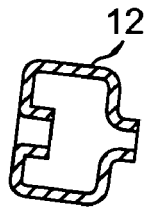

FIG. 14A illustrates one embodiment of an ablation apparatus 10, including one or more loops 12 that can be positioned around the pulmonary veins 13. The loops 12 shown in FIG. 14A can operate according to a snare mechanism in order to pull the pulmonary veins 13 toward the insertion tool 32. The ablation apparatus 10 can also include an insertion tool 32 and a handle 52. FIG. 14B illustrates an embodiment of the ablation apparatus 10 including an insertion tool 32 coupled to a double loop 12. The loop 12 can make multiple circular loops around the pulmonary veins 13. FIG. 14C illustrates an embodiment of the ablation apparatus 10, including a single loop 12 that can be positioned around the pulmonary veins 13. The loop 12 can be attached to an insertion tool 32. FIG. 14D illustrates the ablation apparatus 10 including an insertion tool 32 that can receive a conductor 16 and a liquid delivery tube 54. The insertion tool 32 can include one or more loops 12 coupled to a distal end of the ablation apparatus 10. FIG. 14E illustrates a cross-sectional view of one embodiment of a loop 12. The cross-sectional view shown in FIG. 14E can be a cross section of a balloon apparatus that can be used as a loop 12.

Figure 15B:
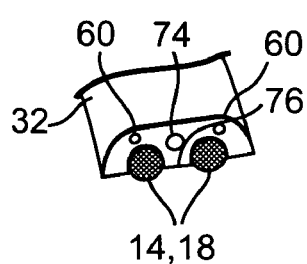
FIGS. 15A-15F are perspective views of ablation apparatuses according to some embodiments of the invention.
Figure 15A:
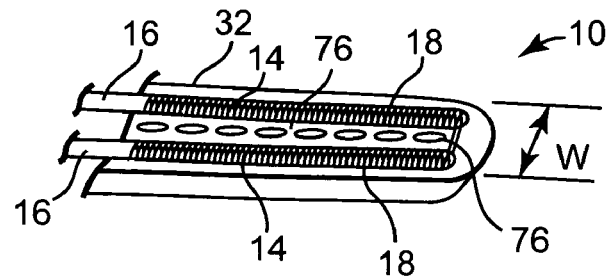
Figure 15D:
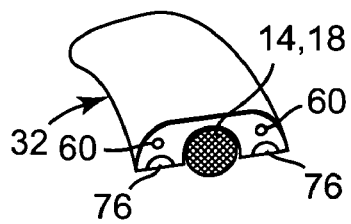
Figure 15C:
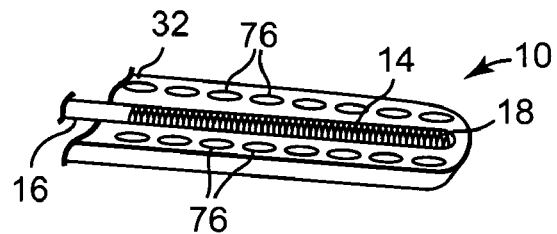
Figure 15F:
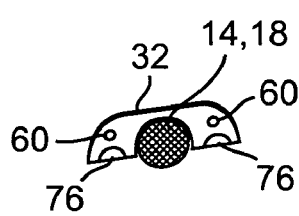
Figure 15E:
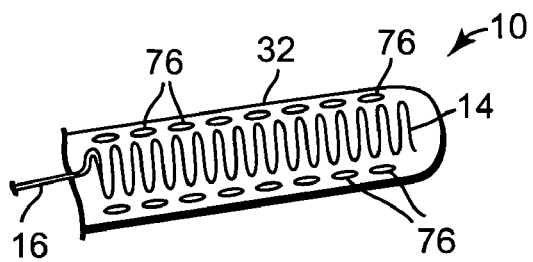

FIGS. 15A-15F illustrate another embodiment of the ablation apparatus 10. The ablation apparatus 10 can include a substantially flat surface that can contact the target tissue 15. As shown in FIG. 15A, the ablation apparatus 10 can include coil electrodes 14, one or more tubes 18, one or more conductors 16, and vacuum pods 76. FIG. 15B is a perspective end view of the ablation apparatus 10 illustrating the electrodes 14 which can be placed within the tubes 18. FIG. 15B also illustrates vacuum channels 74 which can be connected to the vacuum pods 76. FIG. 15B further illustrates that the ablation apparatus 10 can include one or more saline orifices 60 in order to provide saline or liquid to the electrodes 14. FIGS. 15A-15F also illustrate that the insertion tool 32 can incorporate the electrodes 14 and the tubes 18. The insertion tool 32 can include any combination of the tubes 18 and devices or components used to position the electrodes 14 adjacent the target tissue 15. FIG. 15C illustrates the ablation apparatus 10 including two parallel sets of vacuum pods 76 positioned on either side of the coil electrodes 14. FIG. 15D is another perspective end view of the ablation apparatus 10 including two parallel sets of vacuum pods 76 and two parallel saline orifices 60. Similarly, FIG. 15F illustrates two parallel sets of vacuum pods 76 and two parallel sets of saline orifices 60. FIG. 15E illustrates an ablation apparatus 10 with coil electrodes 14 that can occupy a larger surface area of the ablation apparatus 10 in order to contact a larger surface area of the target tissue 15. The coil electrodes 14 shown in FIGS. 15A-15E can include a substantially continuous piece of conductive material that can overlap and collapse onto itself in order to provide a substantially continuous conductor along the length of the tube 18 and/or the insertion tool 32. The use of coil electrodes 14 can also allow the tube 18 and/or the insertion tool 32 to be flexible enough to be positioned around the pulmonary veins 13. As shown in FIG. 15A, the ablation apparatus 10 can include a width w that can be approximately 8 mm or less. In some embodiments, the coil electrodes 14 can be etched onto one or more integrated circuits positioned within the tube 18 and/or the insertion tool 32.

Figure 16:
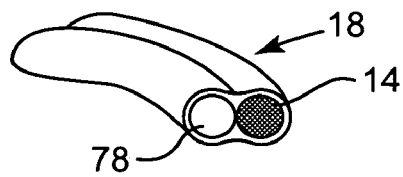
FIG. 16 is a partial perspective view of a tube for use with an ablation apparatus according to one embodiment of the invention.

FIG. 16 illustrates one embodiment of a tube 18 having multiple channels. One of the channels can include electrodes 14 and a second channel 78 can provide a space between the electrodes 14 and the pulmonary veins 13. The tube 18 with multiple channels can also be used to provide saline to the target tissue 15.

Figure 17A:
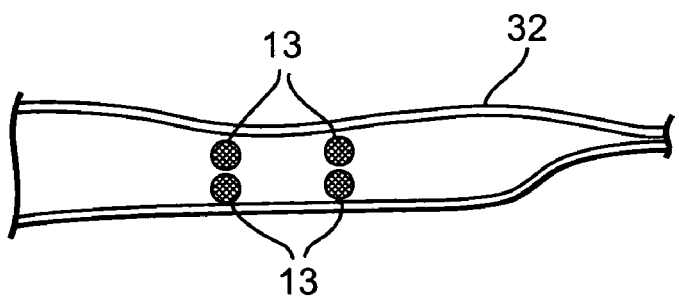
FIGS. 17A-17C are schematic views of an ablation apparatus according to one embodiment of the invention.
Figure 17B:
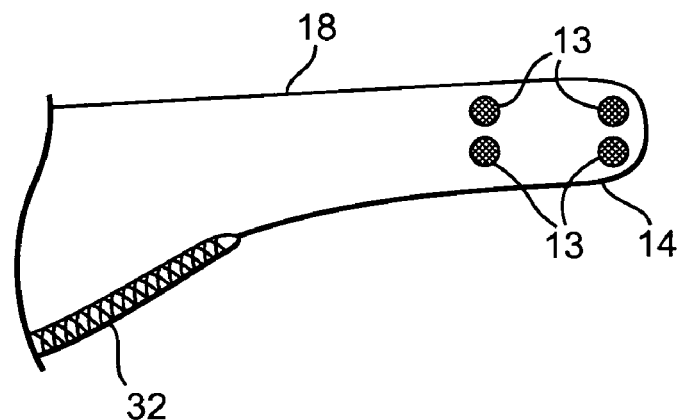
Figure 17C:
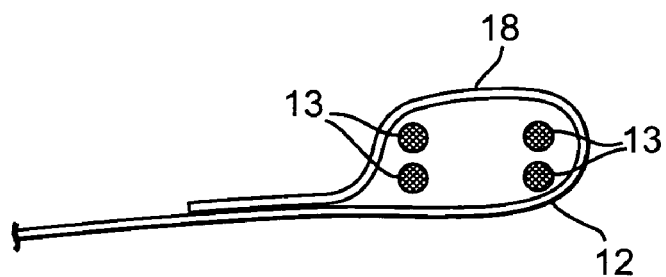

FIGS. 17A-17C illustrate an embodiment of the invention that can include the use of rubber catheters as insertion tools 32 which can be passed around the pulmonary veins 13. A tube 18 including electrodes 14 can then be pulled through the rubber catheters of the insertion tool 32 in order to be wrapped around the pulmonary veins 13. As shown in FIG. 17C, the tube 18 can create a loop 12 substantially surrounding the pulmonary veins 13. In some embodiments, the tube 18 can include a catheter. The catheter can use microwave energy to ablate the target tissue 15. In one embodiment, the catheter can be approximately 18 mm in width with a semi-circular cross-sectional profile.

FIGS. 18A and 18B illustrate another embodiment of the ablation apparatus 10, including electrodes 14 contained within a tube 18. The tube 18 can be coupled to an insertion tool 32, and the insertion tool 32 can include a stiffener 80. The insertion tool 32 including the stiffener 80 can have a diameter of approximately 8 mm, in one embodiment. The stiffener 80 can include a rectangular cross section which can substantially prevent or resist rotation of the insertion tool 32 with respect to the pulmonary veins 13 and/or the target tissue 15.

FIG. 19 is a schematic illustration of target tissue 15 being clamped by a loop 12 including a tube 18. The tube 18 can include bipolar electrodes 14. The target tissue 15 can include two ablation surfaces adjacent the portions of the tube 18.

FIG. 20 illustrates an insertion tool 32 to which electrodes 14, an insulator 82, and a stiffener 80 can be coupled. The insertion tool 32 can be positioned around the pulmonary veins 13, and then the stiffener 80 can be slid onto the insertion tool 32 adjacent the electrodes 14 and the insulator 82. In some embodiments, the electrodes 14 can be coupled to the stiffener 80. In some embodiments, the stiffener 80 can be shaped according to the contours of the left atrium. In one embodiment, the stiffener 80 can be constructed of expanded polytetrofluroroethylene (ePTFE). The insertion tool 32 can also include a tube 18 in order to provide energy and saline to the electrodes 14 and the target tissue 15.

FIG. 21 illustrates an embodiment of the tube 18 and/or the insertion tool 32, including a connecting cable 84 that can be used to connect two segments of the tube 18 or the insertion tool 32. The connecting cable 84 can allow the electrodes 14 to be positioned around the pulmonary veins 13 by providing a flexible portion that can position more rigid segments of the tube 18 above and below the pulmonary veins 13. The connecting cable 84 can be a non-extensible member and can include a suitable cover.

Figure 22A:
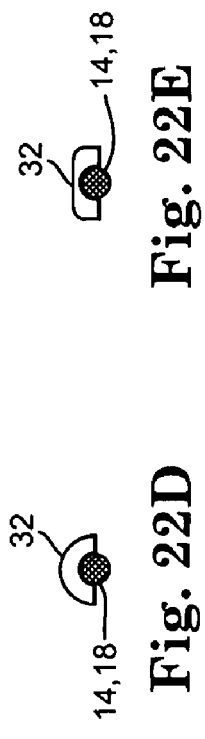
FIGS. 22A-22E are perspective and side cross-sectional views of ablation apparatuses according to some embodiments of the invention.
Figure 22B:
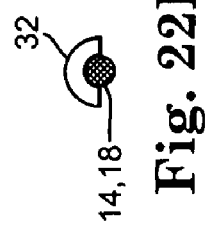
Figure 22C:
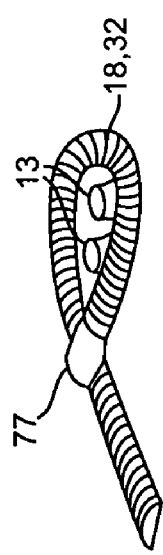
Figure 22D:
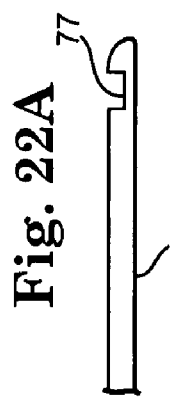
Figure 22E:
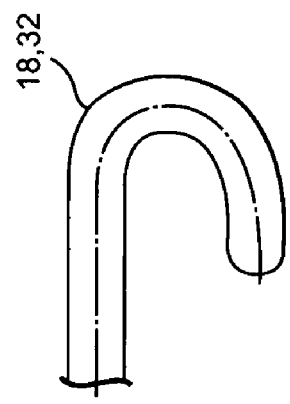

FIGS. 22A-22E illustrate one embodiment of the ablation apparatus 10 that can include a recess 77 which can allow the tube 18 and/or the insertion tool 32 to wrap around onto itself and be positioned within the recess 77. As shown in FIGS. 22D and 22E, the electrodes 14 and/or the tube 18 can be coupled to the insertion tool 32 and can have a semi-circular cross-sectioned profile or a rectangular cross-sectioned profile. As shown in FIG. 22A, the tube 18 and/or the insertion tool can wrap around onto itself and be positioned within the recess 77 in order to surround the pulmonary veins 13.

Figure 23:
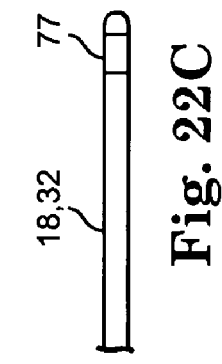
FIG. 23 is a bottom view of an ablation apparatus according to one embodiment of the invention.

FIG. 23 illustrates an embodiment of the ablation apparatus 10, including a single coil electrode 14 and a single row of vacuum pods 76. The ablation apparatus 10 shown in FIG. 23 can include a width w of approximately 8 mm, in one embodiment.

Figure 24:
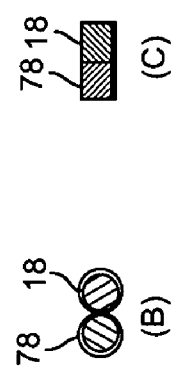
FIG. 24 is a side view of an ablation apparatus according to one embodiment of the invention.

FIG. 24 illustrates an embodiment of the tube 18 and/or the insertion tool 32 having a minimum radius R. The minimum radius R can be a radius that is sufficient to surround the pulmonary veins 13. If the tube 18 is constructed with a single channel, the minimum radius R can be smaller than if the tube 18 is constructed with multiple channels that are not independent of one another.

Figure 25:
FIGS. 25A-25D are cross-sectional views of tubes of ablation apparatuses according to some embodiments of the invention.

FIGS. 25A-25D illustrate multiple-channel tubes 18, including a spacer channel 78 that can provide spacing between the electrodes 14 and the pulmonary veins 13. FIG. 25A illustrates two circular channels with a male projection and a female recess used to couple the channels to one another. FIG. 25B illustrates two circular channels, which can be coupled to one another by ultrasonic welding or any other suitable method. FIG. 25C illustrates multiple channels having rectangular cross-sectional profiles. FIG. 25D illustrates multiple channels having triangular cross-sectional profiles.

In some embodiments, the insertion tool 32 can be placed in a secure position with respect to the pulmonary veins 13 before the electrodes 14 are inserted into the tube 18. In some embodiments, a double loop 12 can be used to surround both sets of pulmonary veins 13. When a double loop 12 is used, the length of the electrodes 14 can be shorter. However, the double loops 12 must bend more tightly around the two sets of pulmonary veins 13. The double loops 12 must also overlap more often and may be subjected to more abrupt contour changes. In some embodiments, a single loop 12 can be used and can include a longer electrode 14. The single loop 12 can overlap itself only once and can include a larger bend radius R.

FIG. 26 illustrates an embodiment of the tube 18 and/or the insertion tool 32, including two segments connected by a connecting cable 84. The connecting cable 84 can be used to limit deflection when the atria are clamped. The connecting cable 84 can be co-extruded with the material of the tube 18 and/or the insertion tool 32. The tube 18 and/or the insertion tool 32 can be constructed of a flexible material, such as a porous polymer.

FIGS. 27A-27F illustrate an embodiment of the ablation apparatus 10, including coil electrodes 14 and a stiffener 80 coupled to the tube 18 and/or the insertion tool 32. The insertion tool 32 can also include saline channels 58. As shown in FIG. 27A, the stiffener 80 can have a circular cross-sectional profile. As shown in FIG. 27B, the stiffener 80 can have a rectangular cross-sectional profile. In FIG. 27B, the saline channels 58 are positioned between the stiffener 80 and the coil electrode 14. FIGS. 27C and 27D illustrate the coil electrodes 14 positioned along a flat surface of the insertion tool. The insertion tool 32 can have a width w of approximately 6 mm to 8 mm. The coil electrode 14 can include a flat overlapping coil that gives a coil-to-coil electrical pathway for the ablation apparatus 10. FIGS. 27E and 27F illustrate the attachment of the connecting cable 84 between two segments of the tube 18 and/or the insertion tool 32. As shown in FIG. 27E, the connecting cable 84 can be positioned on one side of the stiffener 80 with the saline channels 58 positioned on the other side of the stiffener 80. FIG. 27F illustrates the stiffener 80 positioned on one side of a row including a saline channel 58, the connecting cable 84, and a conductor 16. The stiffener 80 can be constructed of a material that is stiff enough to prevent any of the channels within the insertion tool 32 from collapsing as they pass over sharp bends.

Figure 28A:
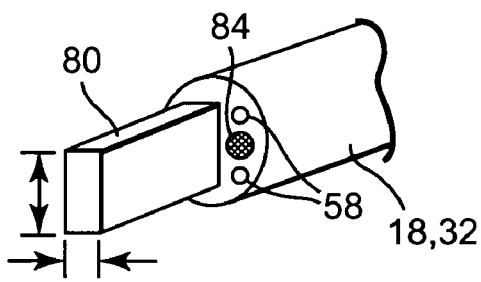
FIGS. 28A-28D are cross-sectional, perspective, and schematic views of ablation apparatuses according to some embodiments of the invention.
Figure 28C:
Figure 28B:
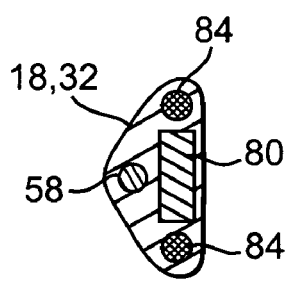
Figure 28D:
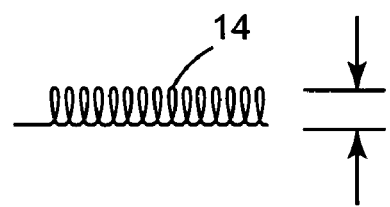

FIGS. 28A-28B illustrate an embodiment of the ablation apparatus 10, including a tube 18 and/or an insertion tool 32 with a triangular or circular cross section with one saline channel 58, a stiffener 80, and two connecting cables 84. FIGS. 28C and 28D illustrate a coil electrode 14 suitable for use with the ablation apparatus 10 of FIGS. 28A and 28B. The connecting cable 84 can be used to connect two segments of the tube 18 and/or the insertion tool 32. The coil electrodes 14 can be used as bipolar electrodes that can wrap around the pulmonary veins about the connecting cables 84.

Figure 29A:
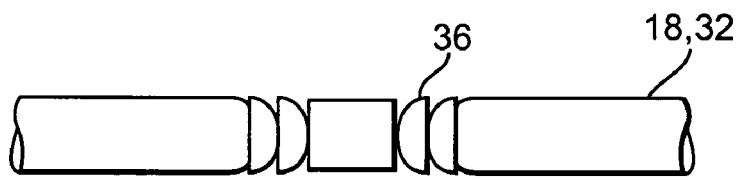
FIGS. 29A-29B are side views of ablation apparatuses according to some embodiments of the invention.
Figure 29B:
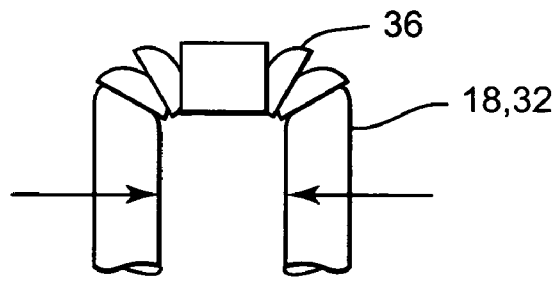

FIGS. 29A-29B illustrate an embodiment of the tube 18 and/or the insertion tool 32, including articulating segments 36. FIG. 29B illustrates the articulating segments 36 in a bent position in order to wrap around the pulmonary veins 13.

FIGS. 30A through 30F illustrate embodiments of the ablation apparatus 10, including one or more connecting cables 84, hinges 88, or spherical joints 92. FIG. 30A illustrates the tube 18 and/or the insertion tool 32 coupled to an adapter 86, a stiffener 80, and a connecting cable 84. FIG. 30B illustrates the adapter 86 coupled to the tube 18, and/or the insertion tool 32 with the adapter 86 having an overlapping sheath configuration. FIG. 30C illustrates the connecting cable 84 extending through two segments of the tube 18 and/or the insertion tool 32. The connecting cable 84 can be coupled to the two segments with one or more adapters 86. FIG. 30D illustrates a hinge 88, including a link 90 coupled between two segments of the tube 18 and/or insertion tool 32. The electrodes 14 can be coupled to suitable portions of the tube 18. The hinge 88 can be connected to one or more adapters 86. FIG. 30E illustrates a spherical joint 92 coupled between adapters 86 which are coupled to two segments of the tube 18 and/or the insertion apparatus 32. FIG. 30F illustrates a connecting screw 94 coupled to two portions of an adapter 86. The screw can be used to move the connecting cable 84 with respect to the adapter 86.

Figure 31:
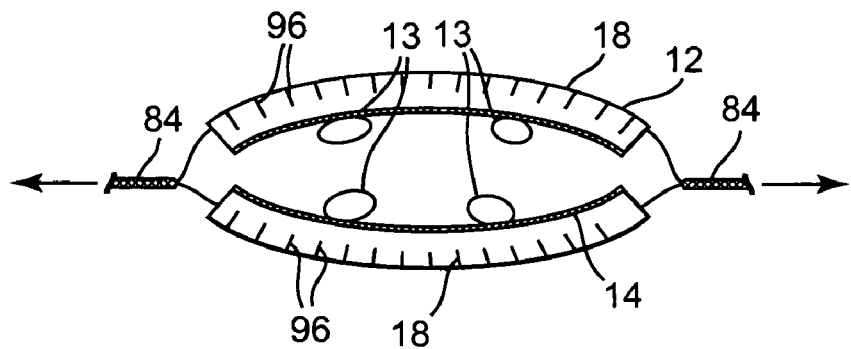
FIG. 31 is a side view of an ablation apparatus according to one embodiment of the invention.

FIG. 31 illustrates an embodiment of the tube 18, including slits 96 positioned along a portion of its length. The slits 96 can increase the flexibility of a portion of the tube 18. Electrodes 14 can be coupled to an interior portion of the tube 18 adjacent the pulmonary veins 13. The tube 18 can form a loop 12 surrounding the pulmonary veins 13 and ends of the tube 18 can be coupled to one or more connecting cables 84.

Figure 32A:
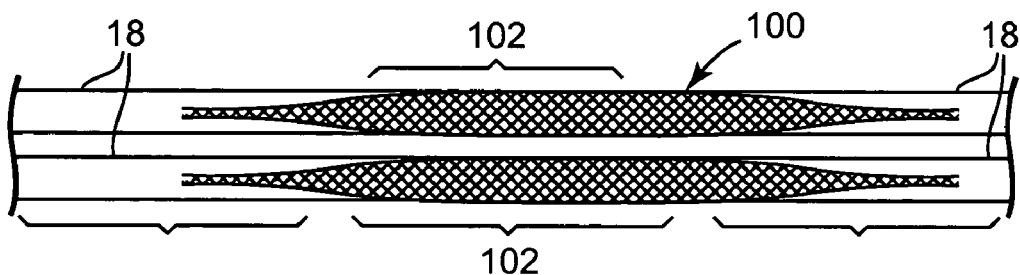
FIGS. 32A-32B are side views of an ablation apparatus according to one embodiment of the invention.
Figure 32B:
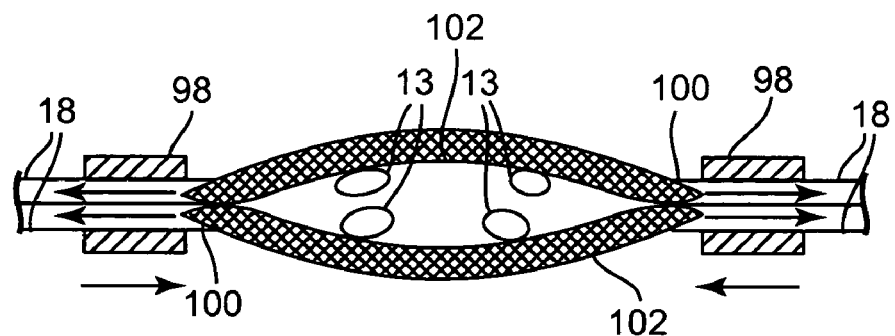

FIGS. 32A and 32B illustrate an embodiment of the ablation apparatus 10, including one or more tapered portions 100 and a clamping area 102 positioned along the length of the tube 18. As shown in FIG. 32B, the clamping area 102 can be positioned adjacent to the pulmonary veins 13. One or more clamps 98 can be coupled near the tapered portions 100 of the tubes 18 in order to clamp the tubes 18 to form a clamping area 102 around the pulmonary veins 13. In some embodiments, the tubes 18 can include semi-circular cross-sectional profiles so that their substantially flat surfaces can contact one another.

Figure 33A:
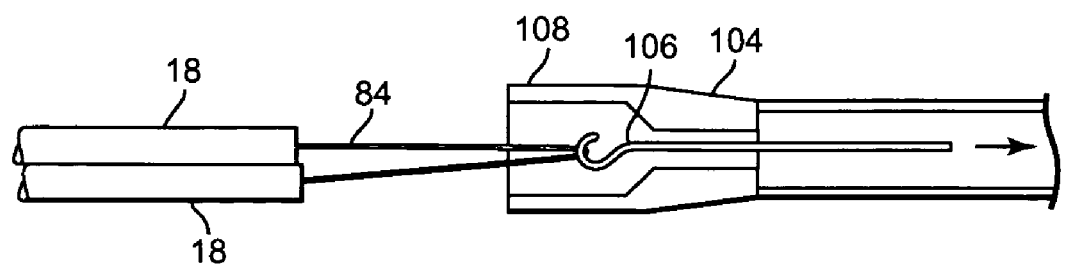
FIGS. 33A-33B are side views of an ablation apparatus according to one embodiment of the invention.
Figure 33B:
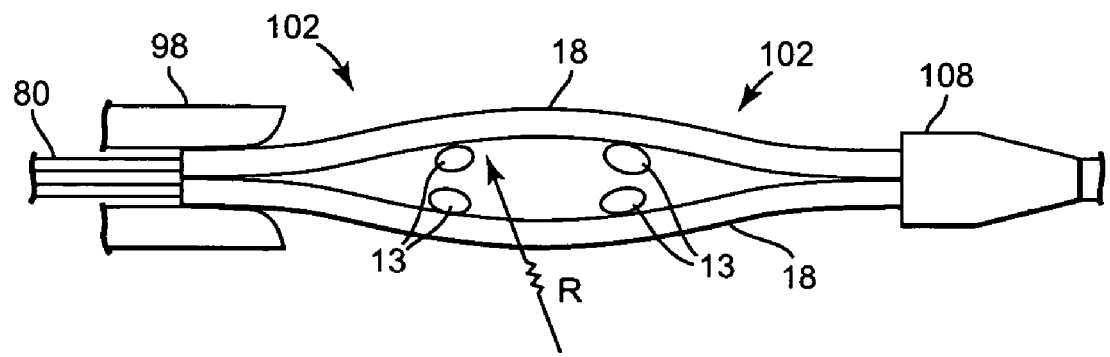

FIGS. 33A and 33B illustrate a retrieval device 104 for use with the ablation apparatus 10. The retrieval device 104 can include a hook 106 and a sheath 108. The hook 106 can be used to grasp the connecting cable 84 in order to pull the tubes 18 toward the sheath 108. As shown in FIG. 33B, the sheath 108 can surround a portion of the tubes 18. The tubes 18 can be positioned according to a clamping area 102 around the pulmonary veins 13. A clamp 98 can be coupled to the tubes 18. The tubes 18 can also include one or more stiffeners 80. The clamping area 102 can include a minimum radius R which can be controlled by the stiffness of the stiffeners 80.

Figure 34A:
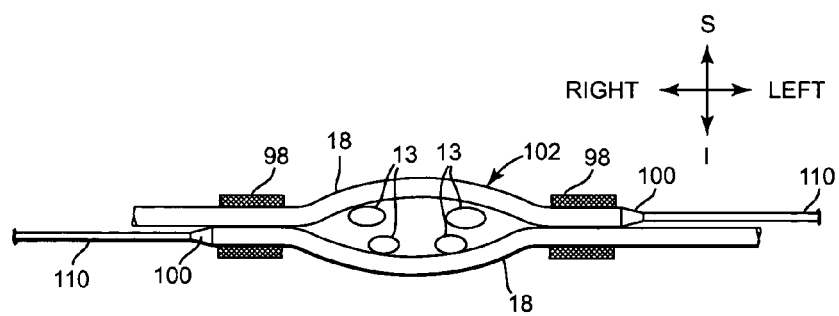
FIGS. 34A-34B are side views of an ablation apparatus according to one embodiment of the invention.
Figure 34B:
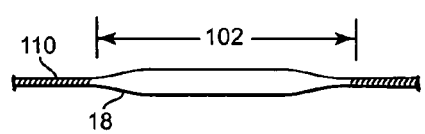

FIGS. 34A and 34B illustrate an embodiment of the tube 18, including a taper 100 coupled to a guide wire 110. The guide wires 110 of the tubes 18 can be used to feed the tubes 18 around the pulmonary veins 13. Once a clamping area 102 of the tubes 18 is positioned around the pulmonary veins 13, the tubes 18 can be clamped together by one or more clamps 98. The guide wires 110 and the tubes 18 can fit within a catheter serving as the insertion tool 32. The clamping area 102 of the tube 18 can also include a stiffener 80.

Figure 35B:
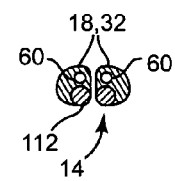
FIGS. 35A-35B are perspective and cross-sectional views of tubes for use with an ablation apparatus according to one embodiment of the invention.
Figure 35A:
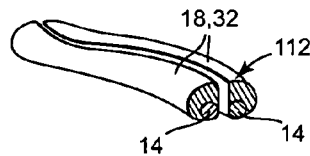

FIGS. 35A and 35B illustrate an embodiment of the tube 18 and/or the insertion tool 32, including electrodes 14 that are positioned in an off-centered manner. The tubes 18 and/or the insertion tools 32 can include substantially flat surfaces 112 for alignment with one another. The tubes 18 and/or the insertion tools 32 can also include saline orifices 60 positioned off-center with respect to the electrodes 14. The electrodes 14 can be offset with respect to the tube 18 in order to provide insulating protection for the pulmonary veins.

Figure 36:
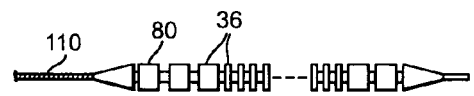
FIG. 36 is a side view of an ablation apparatus according to one embodiment of the invention.

FIG. 36 illustrates a stiffener 80 coupled to a guide wire 110. The stiffener 80 can include articulating segments 36 having varying lengths and/or diameters in order to modify the stiffness of the stiffener 80.

Figure 37:
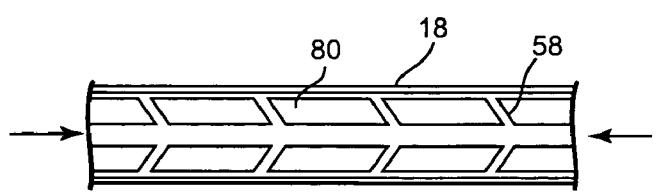
FIG. 37 is a side view of an ablation apparatus according to one embodiment of the invention.

FIG. 37 illustrates an embodiment of the tube 18, including a stiffener 80 with several segments. Saline channels 58 can be positioned in a diagonal manner between the segments of the stiffener 80.

Figure 38:
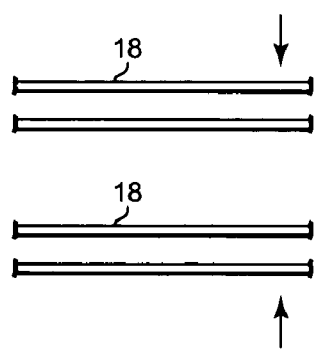
FIG. 38 is a side view of an ablation apparatus according to one embodiment of the invention.

FIG. 38 illustrates two tubes 18 which can be positioned around the pulmonary veins 13 and can move parallel toward one another in order to maintain their parallel configuration.

Figure 39A:
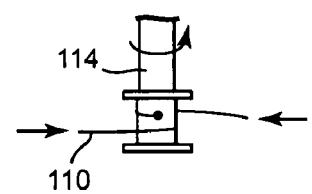
FIGS. 39A-39B are side and top schematic views of an ablation apparatus according to one embodiment of the invention.
Figure 39B:
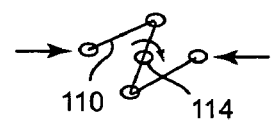

FIGS. 39A and 39B illustrate a spool 114 around which a guide wire 110 can be wrapped.

Figure 40A:
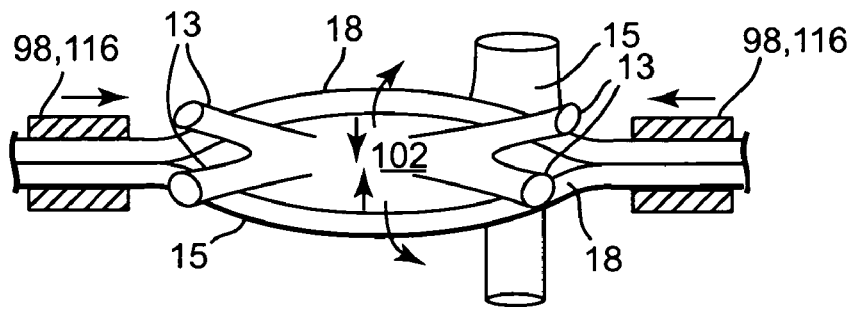
FIGS. 40A-40G are perspective, schematic, and cross-sectional views of ablation apparatuses according to some embodiments of the invention.
Figure 40B:
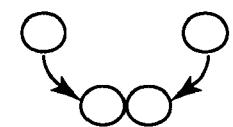
Figure 40E:
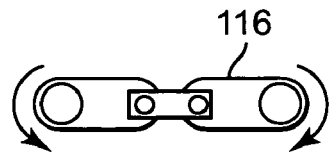
Figure 40C:
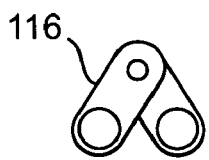
Figure 40G:
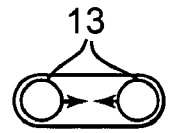
Figure 40D:
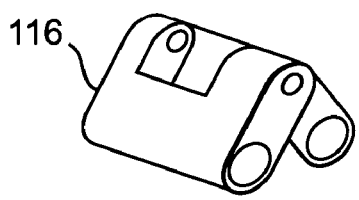
Figure 40F:
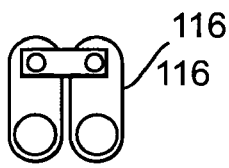

FIGS. 40A-40G illustrate an embodiment of the ablation apparatus 10, including one or more clamps 98 which can include clamping hinges 116. The tubes 18 can be positioned adjacent the pulmonary veins 13 and the clamping hinges 116 can be secured in order to create a clamping area 102 around the pulmonary veins 13. In some embodiments, the clamping hinges 116 can be used to rotate the tubes 18 in order to roll off of the pulmonary veins 13 and onto the target tissue 15. FIG. 40B illustrates the pulmonary veins 13 after a clamping action has been performed. FIG. 40C illustrates a clamping hinge 116 including two links. FIG. 40D is a perspective view of the clamp hinge 116 of FIG. 40C. FIG. 40F illustrates the clamp hinge 116 of FIG. 40E in a clamped position. FIG. 40G illustrates an example of the clamping action that can be performed on the pulmonary veins 13. In some embodiments, clamping the atria can be performed by using the clamping hinge 116 in order to allow a slow blood flow to reduce convective heat loss. However, it is not necessary in all embodiments of the invention to clamp the atria.

Figure 41:
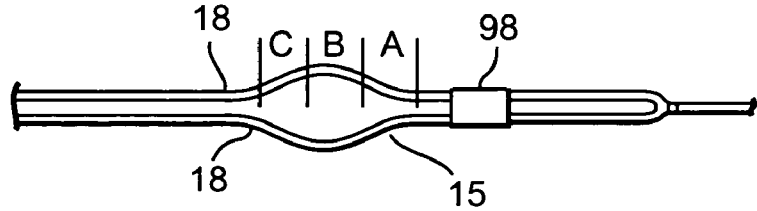
FIG. 41 is a side view of an ablation apparatus according to one embodiment of the invention.

FIG. 41 illustrates an embodiment of the ablation apparatus 10 including multiple segments A, B, C that can be activated independently and separately for ablation of the target tissue 15. For example, independent segments A, B and C can each be activated separately. This step-wise method can eliminate occluding all four of the pulmonary veins simultaneously.

FIGS. 42A-42H illustrate an embodiment of the ablation apparatus 10, including a tube 18 forming a loop 12. Stiffening rods or members 80 can be inserted into the tube 18 as shown in FIG. 42A. The tube 18 can be constructed of a porous polymer, in some embodiments. As shown in FIG. 42A, the tube 18 can include a distal hinge area A. The distal hinge area A can be replaced with a non-extensible connecting cable 84. As shown in FIG. 42B, the tube 18 can be coupled to one or more adapters 86 and the adapters 86 can be coupled to the connecting cable 84. The tube 18 can also receive the stiffeners 80. An area between the adapters 86 and the stiffeners 80 can include a weakened portion 118. The weakened portion 118 can flex over the stiffener 80 in order to reduce clamping at a distal end of the tube 18 and the loop 12. FIG. 42C illustrates two segments of the tube 18 aligned parallel to one another and connected by the connecting cable 84. FIG. 42D illustrates two segments of the tube 18 connected by a single connecting cable 84. FIG. 42E illustrates two segments of the tube 18 connected by two connecting cables 84. FIGS. 42F and 42G illustrate alternative embodiments of the adapter 86. In FIG. 42F, the adapter 86 can include a C-shaped member that can be received within the interior of the tube 18. The adapter 86 shown in FIG. 42G can include a C-shaped member that can extend over an exterior surface of the tube 18. FIG. 42H illustrates one suitable cross-sectional profile for the tube 18. The cross-sectional profile can include a semi-circular shape. Each tube 18 can be coupled to the connecting cable 84. The semi-circular cross-sectional profile can help to maintain orientation between the two segments of the tube 18.

Figure 43A:
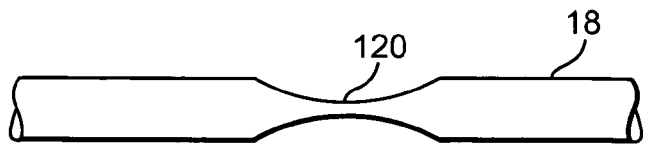
FIGS. 43A-43D are side and cross-sectional views of an ablation apparatus according to one embodiment of the invention.
Figure 43D:
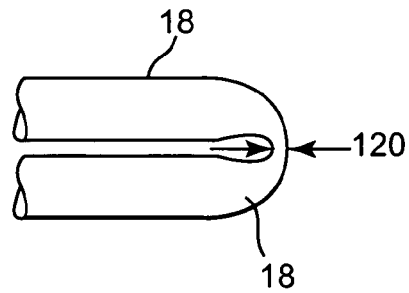
Figure 43B:
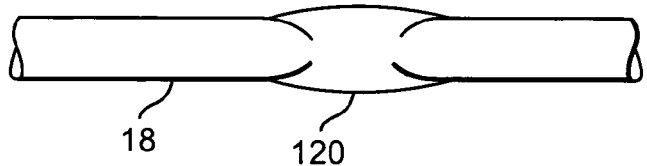
Figure 43C:
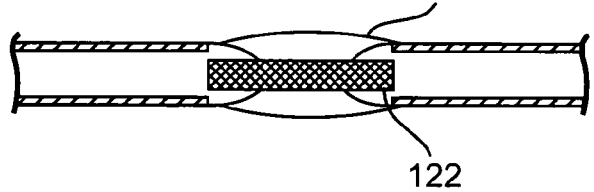

FIGS. 43A-43D illustrate an embodiment of the tube 18 including a compressed portion 120. The compressed portion 120 can, in some embodiments, be formed with ultrasonic welding techniques. As shown in FIG. 43C, a substantially flat braided material 122 can be embedded in the compressed portion 120 in order to reduce the stretch of the compressed portion 120 during bending. FIG. 43D illustrates two segments of the tube 18 folded over so that they are substantially parallel to one another with the compressed portion 120 positioned between the two segments of the tube 18.

Figure 44A:
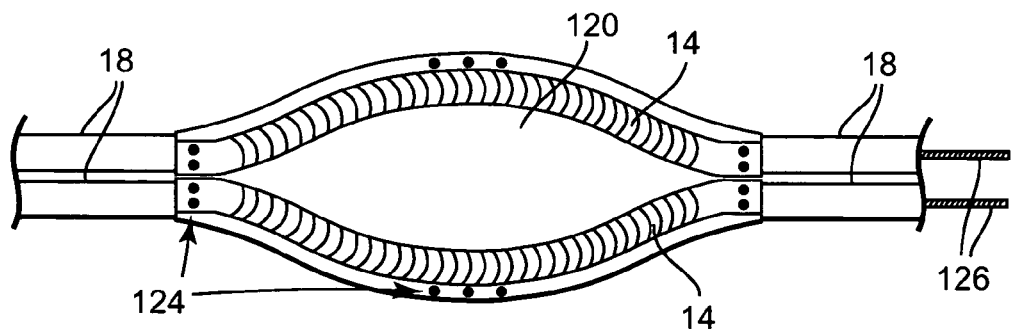
FIGS. 44A-44B are side cross-sectional views of an ablation apparatus according to one embodiment of the invention.
Figure 44B:
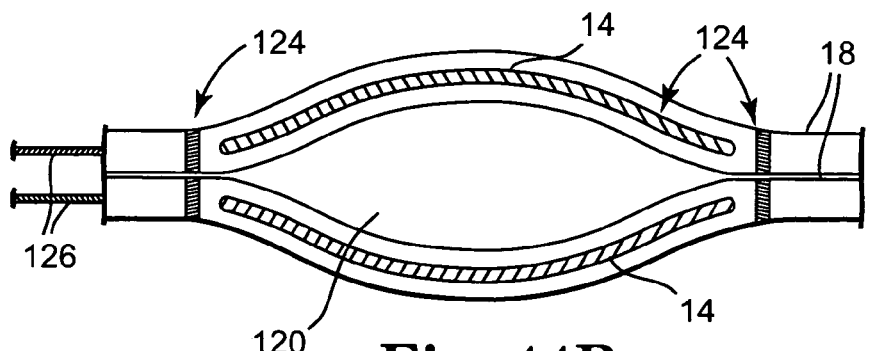

FIGS. 44A-44B illustrate an embodiment of the ablation apparatus 10 including light markers 124. The light markers 124 can be positioned at ends of a clamping area 120 and/or at a mid-point position of the clamping area 120. In some embodiments, energy can be provided to the light markers 124 via fiber optic cables 126. The fiber optic cables 126 can be positioned within the tubes 18. The light markers 124 can aid in positioning and visualizing the ablation apparatus 10 during a closed-chest procedure or within any other closed anatomical space. The light markers 124 can include, for example, light rods, fiber optic bundles, or light-emitting diodes. The light markers 124 can, in some embodiments, be integrated into the ablation apparatus 10 itself. The light bundles 124 can be color-coded or can emit light patterns in order to be used to identify specific points that are critical to the placement or to the use of the ablation apparatus 10. The light markers 124 can be rings or lines of light-emitting materials, such as light emitting diodes. The light markers 124 can be used to locate and confirm placement of the clamping area 120. FIG. 44A illustrates light markers 124 that include points of light. FIG. 44B illustrates light markers 124 that include rings or lines of light.

Some embodiments of the invention can include an ablation apparatus 10 that is intended to allow the threading of an insertion tool 32, such as an ablation catheter, around the pulmonary veins 13 to perform epicardial left atrial ablation. Placement of the ablation apparatus 10 can be achieved through a right thoracotomy after dissection of the inferior vena cava and superior vena cava from the pericardium. The ablation catheter can include a magnet, such as a rare earth magnet constructed of neodymium or samarium-cobalt. The magnet can be placed on the tip of the ablation catheter. The ablation catheter can be advanced through the transverse sinus to the distal side of the left pulmonary veins 13. A retrieval catheter with a mating magnet can be advanced through the oblique sinus to mate with the ablation catheter. A steerable end on the retrieval catheter and/or the ablation catheter can aid in the mating of the two magnet ends. The retrieval catheter can then be used to pull the ablation catheter through the oblique sinus. A final loop 12 can be closed by attaching the magnetic distal end on the ablation catheter to a magnetic slide on the proximal end and pulling the loop 12 tighter in order to cause sufficient contact between the ablation catheter and the left atrial epicardial surface. Embodiments of the ablation apparatus 10 can be used to facilitate placement of a loop-type ablation catheter around the left atrium through the transverse and oblique sinuses through a single right thoracotomy without additional visual visualization.

Figure 45A:
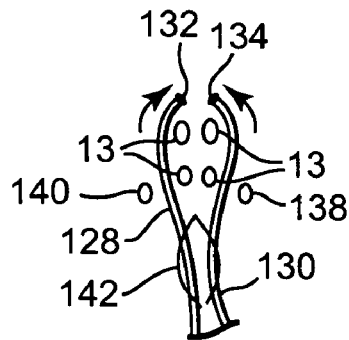
FIGS. 45A-45C are schematic views of an ablation apparatus according to one embodiment of the invention.
Figure 45B:
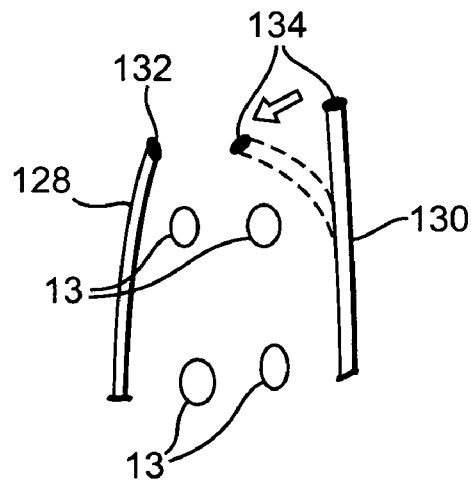
Figure 45C:
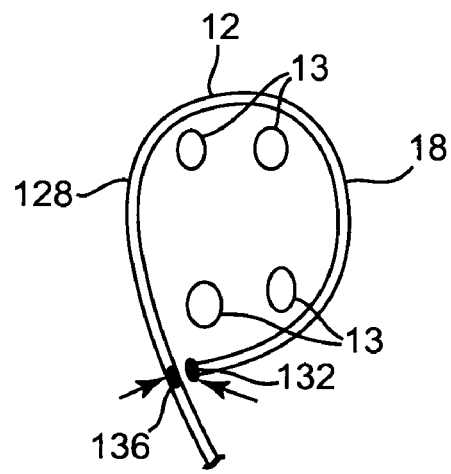

FIGS. 45A-45C illustrate an embodiment of an ablation apparatus 10, including an ablation catheter 128 and a retrieval catheter 130. A first magnet 132 can be coupled to a distal tip of the ablation catheter 128, and a second magnet 134 can be coupled to a distal tip of the retrieval catheter 130. As shown in FIG. 45A, the ablation catheter 128 and the retrieval catheter 130 can be inserted through a single right thoracotomy. The ablation catheter 128 can be inserted between the superior vena cava 140 and the pulmonary veins 13. The retrieval catheter 130 can be inserted between the pulmonary veins 13 and the inferior vena cava 138. As shown in FIG. 45B, the first magnet 132 of the ablation catheter 128 can be attracted to the second magnet 134 of the retrieval catheter 132 in order to pull the ablation catheter 128 around the pulmonary veins 13 forming a loop 12, as shown in FIG. 45C. The ablation catheter 128 can include a third magnet 136 which can attract the first magnet 132 once the retrieval catheter 130 has positioned the distal end of the ablation catheter 128 completely around the pulmonary veins forming a complete loop 12. In this manner, the ablation catheter 128 can be threaded around the pulmonary veins 13 through a single right thoracotomy or any other suitable type of thoracotomy. The magnets 132, 134, and 136 can be constructed of a rare earth metal.

The magnet 132 can be placed on the distal tip of the ablation catheter 128 and the device can be advanced through the thoracotomy or another suitable port, either superiorly or inferiorly of the pulmonary veins 13. The retrieval catheter 130 can include an opposite attracting magnet 134 that can be advanced through the thoracotomy or a suitable port and positioned opposite the ablation catheter 128 so that the distal tips are ajoined and the pulmonary veins 13 are encircled. The retrieval catheter 130 can then be withdrawn pulling the ablation catheter 128 with it, thus allowing the ablation catheter 128 to fully encircle the pulmonary veins 13. The retrieval catheter 130 can also be constructed to include a deflecting tip to allow for easier mating to the first magnet 132 coupled to the ablation catheter 128. Once both catheters 128, 130 are positioned, the deflecting tip of the retrieval catheter 130 can deflect around the distal pulmonary veins 13 toward the ablation catheter tip. If the magnets are powerful enough, the magnets do not necessarily need to touch one another to become attracted to one another. Alternatively, the ablation catheter 128 can be designed to deflect, rather than the tip of the retrieval catheter 130. In other embodiments, both the tips of the ablation catheter 128 and the retrieval catheter 130 can be constructed to deflect. In order to complete the loop 12, the ablation catheter 128 can include a second proximal magnet 136 positioned in such a way that the distal magnet 132 when joined causes the ablation catheter 128 to form a closed loop 12 around the pulmonary veins 13. This proximal magnet 136 can also be designed so that its position can be altered to adjust the resulting size of the loop 12 for optimal pulmonary vein encirclement.

In one embodiment of the invention, two substantially equal sized electrodes 14 can be incorporated into a single flexible loop 12. After positioning the loop 12 around the desired area of the pulmonary veins 13, rigid members can be inserted into a lumen at both the proximal and distal ends of the loop 12. The proximal ends of the rigid members can then be brought together to join the two electrodes 14. Some embodiments of the invention can be used to create long linear lesions, but can also be flexible for adequate positioning. Some embodiments of the invention can include a bipolar device for creating long linear lesions by placing independent electrodes 14 on each side of the target tissue 15 and applying energy. Some embodiments of the invention can also include a method for inserting flexible electrodes 14 around the posterior left atrium, making the electrode 14 rigid, then folding the ablation apparatus 10 upon itself to create a bipolar pair. The posterior left atrium is the source of initiating most atrial arrhythmias. Isolating this area in a minimaling invasive manner is the goal of atrial arrhythmia surgery. Some embodiments of the invention can provide a simple method for inserting an ablation apparatus 10 around the posterior left atrium and reliably creating electrical isolation and a cure of atrial fibrillation.

Figure 46:
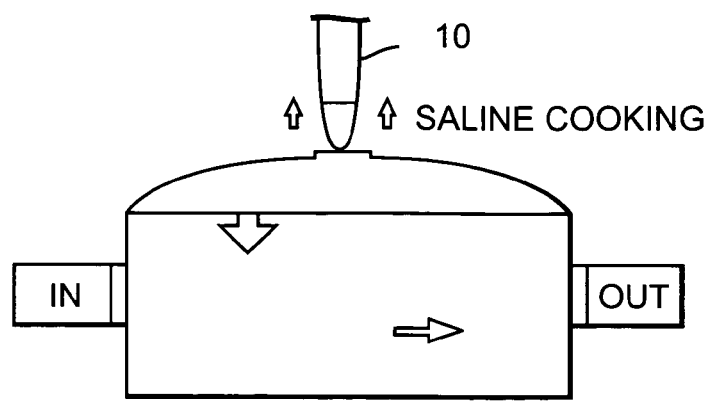
FIG. 46 is a schematic illustration of epicardial ablation bioheat transfer.

FIG. 46 is a schematic representation of epicardial ablation bioheat transfer. Significant endocardial cooling due to convection transfer to flowing blood can occur with embodiments of the ablation apparatus 10.

Some embodiments of the invention can perform bipolar ablation, which can result in generally narrower lesions and less atrial debulking than monopolar ablation approaches. Bipolar ablation, for example, using radio frequency energy, has a greater penetration into the target tissue 15 than monopolar ablation and has a greater likelihood of achieving transmurality. Bipolar ablation allows for better monitoring of changes in tissue impedance to serve as a feedback mechanism for transmurality. Embodiments of the invention can result in less trauma to the patient and less chance of accidentally damaging the heart and surrounding structures. Embodiments of the invention can minimize the size of the incision required to insert the ablation apparatus 10 through the chest wall of the patient. Embodiments of the invention can allow the surgeon to create long contiguous linear lesions in the heart for the purpose of treating atrial fibrillation. The surgeon can create linear lesions in the heart from the epicardial surface of the beating heart. Some embodiments of the invention that do not include catheters can reduce or eliminate the use of blood contacting biomaterials. By creating a loop 12 around the pulmonary veins 13, there is less probability of capturing inadvertent structures in the distal end of the ablation apparatus 10.

Some embodiments of the ablation apparatus 10 can be primarily designed to produce linear radial frequency lesions in the atria using a hemostat device. However, the ablation apparatus 10 can also be used with other energy sources, such as microwave energy, cryogenic energy, thermal energy, ultrasound energy, laser energy, radiation energy or any other suitable type of energy. Also, the ablation apparatus 10 can be used for creating lesions in other tissues, such as the lungs, or during liver resections. Additionally, embodiments of the ablation apparatus 10 can be implemented with various alignment techniques, such as parallel clamping and magnetically-aligning electrodes 14. Embodiments of the invention can include a bipolar ablation apparatus 10 which can be especially useful for ablating on a beating heart, but can also be used on a stopped heart (i.e., on cardiopulmonary bypass). A major challenge to encircling the pulmonary veins 13 from the epicardial surface is to deliver enough energy to the target tissue 15 in order to overcome endocardial heat transfer to the flowing blood. Bipolar devices are capable of bringing the walls in close proximity to each other, thereby eliminating the cooling blood, concentrating the current density between the electrodes 14, and yielding much greater transmurality efficacy. However, bipolar devices must be rigid in order to bring the walls together. Embodiments of the invention provide a method for combining the ease of placing a loop-type tool with the ablation efficacy of a traditional bipolar-type tool. In one embodiment, two equal sized electrodes 14 can be incorporated into a single flexible loop. After positioning the loop 12 around the pulmonary veins 13, rigid members can be inserted into a lumen at both the proximal and distal ends of the loop 12. The proximal ends of the rigid members can then be brought together to approximate the two electrodes 14.

Figures 47A, 47B:
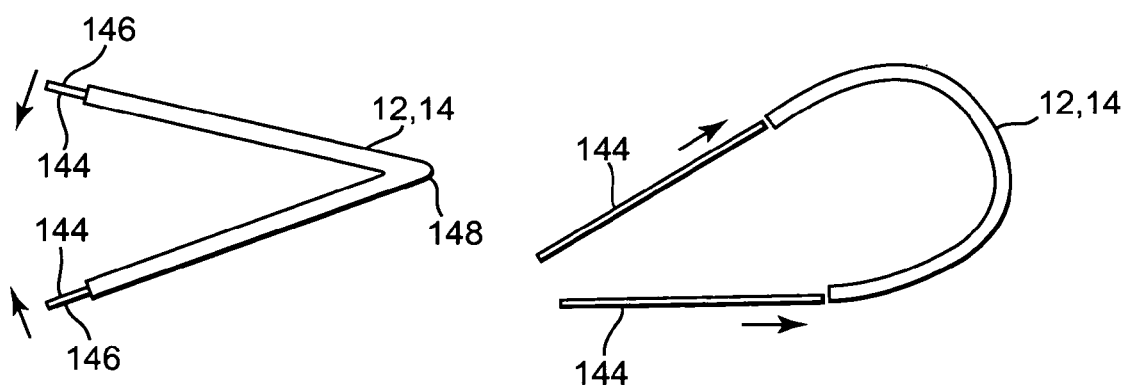
FIGS. 47A-47B are schematic illustrations of ablation apparatuses according to some embodiments of the invention.

FIGS. 47A and 47B schematically illustrate the flexible loop 12 including electrodes 14 positioned around the pulmonary veins 13 and made rigid by insertion of rigid members 144. After insertion of the rigid members 144, the proximal ends 146 of the rigid members 144 can be brought together to create a bipolar configuration in preparation for ablation. To ensure that the loop 12 is divided equally in half, there can be a septum 148 within a lumen at the midpoint. The septum 148 can substantially prevent insertion of the rigid members 144 beyond the midpoint of the loop 12. In some embodiments, the septum 148 can be magnetic to aid in the attachment of the rigid members 144. In some embodiments, the septum 148 and the rigid members 144 can include quick connectors to aid in alignment. In one embodiment, the septum 148 can include a hinge joint to aid in folding the electrode loop 12 upon itself. However, the hinged joint does not necessarily need to be included within the flexible loop 12. Rather, the hinged joint may be a component of one or more of the rigid members 144. In some embodiments, only a distal half of the loop 12 is flexible while a proximal half of the loop 12 is rigid. In some embodiments, only one rigid member 144 is necessary for the distal half of the loop 12. The electrode loop 12 can include two electrodes 14 to create a bipolar pair. However, to accommodate physical limitations, a plurality of bipolar pairs can be included with more than one electrode 14 per half of the loop 12. The rigid members 144 can be curved according to specific anatomical requirements. The rigid members 144 and/or the lumen of the electrode loop 12 can be constructed of or coated with a low friction material (e.g., ePTFE) to aid in insertion. The electrode loop 12 can be steerable, for example, by using catheter pull wires, to facilitate placement. The electrode loop 12 can be shapeable, using a stylet, to facilitate placement. The electrode loop 12 can include a spine or backbone to ensure deflection in only one plane. An insertion tool 32 can include a flexible and/or steerable endoscope. The flexible and/or steerable endoscope can be used to facilitate placement of the loop 12. The endoscope can be positioned first, and the electrode loop 12 can be placed over or within the endoscope.

FIGS. 2A-2E illustrate a path along which the endoscope can be moved through the heart. The endoscope can be positioned first and the distal end of the electrode loop 12 can be attached to the distal end of the steerable endoscope. By withdrawing the steerable endoscope, the electrode loop 12 can also be withdrawn and positioned appropriately with respect to the target tissue. In some embodiments, the proximal half of the electrode loop 12 can be rigid and only the distal half of the electrode loop 12 is flexible. After positioning the electrode loop 12 around the posterior left atrium, a single rigid member can be inserted into the distal end and a bipolar device can be created. After a right thorocotomy, a flexible steereable endoscope can be inserted into the transverse sinus and looped around the posterior left atrium and returned via the oblique sinus. A working channel within the endoscope can be used to insert surgical instruments to facilitate dissection. After dissecting the pericardial reflection under the inferior vena cava, an electrode loop 12 can be inserted into the lumen of the endoscope. When the electrode loop is fully inserted, the endoscope can be withdrawn and the loop 12 can be used to ablate the posterior left atrium.

FIGS. 2A-2E also illustrate the placement of the endoscope and the electrode loop 12 around the pulmonary veins with respect to the transverse sinus and the oblique sinus. In some embodiments, the ablation apparatus 10 can be inserted through a right thorocotomy to simultaneously ablate all the pulmonary veins. However, access can be obtained from another incision such as a sub-xyphoid incision. A sub-xyphoid incision has the benefit of providing access to the left atrial appendage for removal and/or isolation. In some embodiments, the ablation apparatus 10 can be used to simultaneously isolate the entire posterior left atrium. However, the pulmonary veins can be isolated singularly, in pairs, or in any combination. In some embodiments, the ablation apparatus can create long linear lesions and the ablation apparatus 10 can be flexible for positioning, but can be rigid for the ablation process. The ablation apparatus 10 can include a bipolar device for creating long linear lesions by placing independent electrodes 14 on each side of the target tissue 15 and applying energy.

Embodiments of the invention can also include a method for inserting flexible electrodes 14 around the posterior left atrium, making the electrodes 14 rigid, then folding the ablation apparatus 10 upon itself to create a bipolar pair.

Embodiments of the invention can provide a hybrid or semi-rigid ablation apparatus 10. The hybrid ablation apparatus 10 can be placed in position on the left atrium near the junctions of the left and right pulmonary veins 13 in a generally non-rigid state and then be made rigid with the addition of stiffeners 80. These stiffeners 80 can be used to actuate or cooperate with the clamping action of an electrode carrier element of the ablation apparatus 10. The clamping feature of the ablation apparatus 10 can resemble a "bear trap" and can be created by a preformed section on the stiffener 80 or as a permanent feature on the ablation apparatus 10. A permanent clamping feature can include a short preformed rigid section. The permanent clamping feature can also include stiffeners that are essentially straight sections and engage to drive the clamp into the closed position during ablation. The stiffeners 80 can be replaced with flexible shafts, for example, coil, that are capable of carrying the torque load required to position the ablation apparatus 10.

The ablation apparatus 10 can include a catheter that is made rigid after placement adjacent the target tissue 15. The catheter can be used in a minimally-invasive cardiac surgery technique. In some embodiments, the catheter can be deployed through a single-sided surgical approach. The catheter can provide an instantaneous on/off feature to restrict or restore blood flow. The catheter may provide a means for implementing a 2×2 strategy with appropriately designed stiffeners 80. An interlocking segment concept can provide a means for adapting to patient-specific anatomical contours. A bear trap clamp can be used with the atrial tissue by rotating arch-shaped portions of the ablation apparatus 10 anteriorly to a closed position. The bear trap concept can be adaptable to a rigid handle device. Embodiments of the invention also provide a method for providing a flexible-to-rigid system that can integrate a series of interlocking segments that are designed to take a predetermined shape when under a compressive load. This mechanism is analogous to a flex-arm design. In general, a hybrid ablation apparatus 10 can combine various elements of a rigid clamp and a loop-type ablation apparatus device.

Figure 48A:
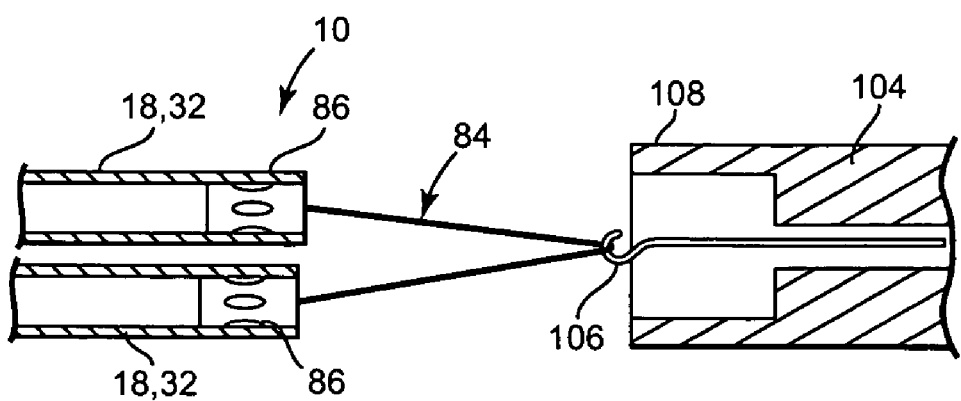
FIGS. 48A-48C are side, perspective, and cross-sectional views of an ablation apparatus according to one embodiment of the invention.
Figure 48B:
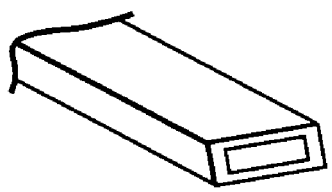
Figure 48C:
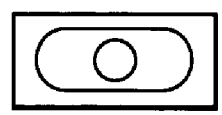

FIGS. 48A-48C illustrate one embodiment of an ablation apparatus 10 and a retrieval device 104. The ablation apparatus 10 can include segments of a tube 18 and/or an insertion tool 32. Adapters 86 can be coupled to a connecting cable 84. FIGS. 48B and 48C illustrate suitable cross-sectional profiles of the tubes 18 and/or the insertion tool 32. The retrieval device 104 can include a hook 106 and a sheath 108. The hook 106 can be used to grasp the connecting cable 84 in order to pull the tubes/insertion tool 18, 32 within the sheath 108.

Figure 49A:
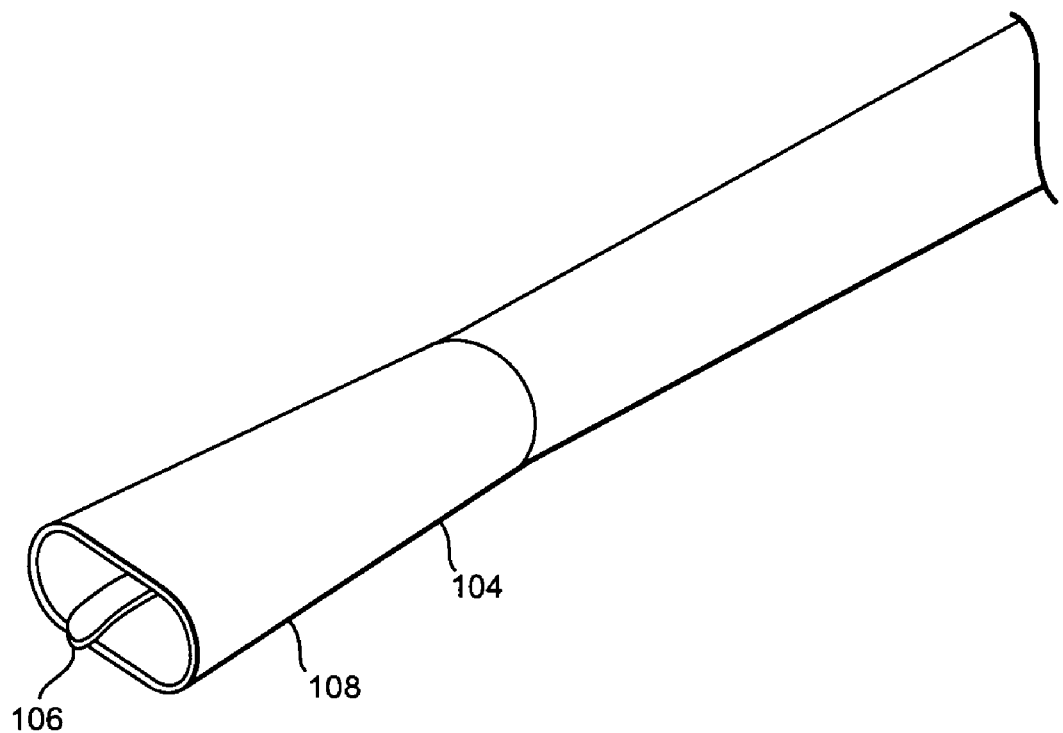
FIGS. 49A-49B are perspective views of an ablation apparatus according to one embodiment of the invention.
Figure 49B:
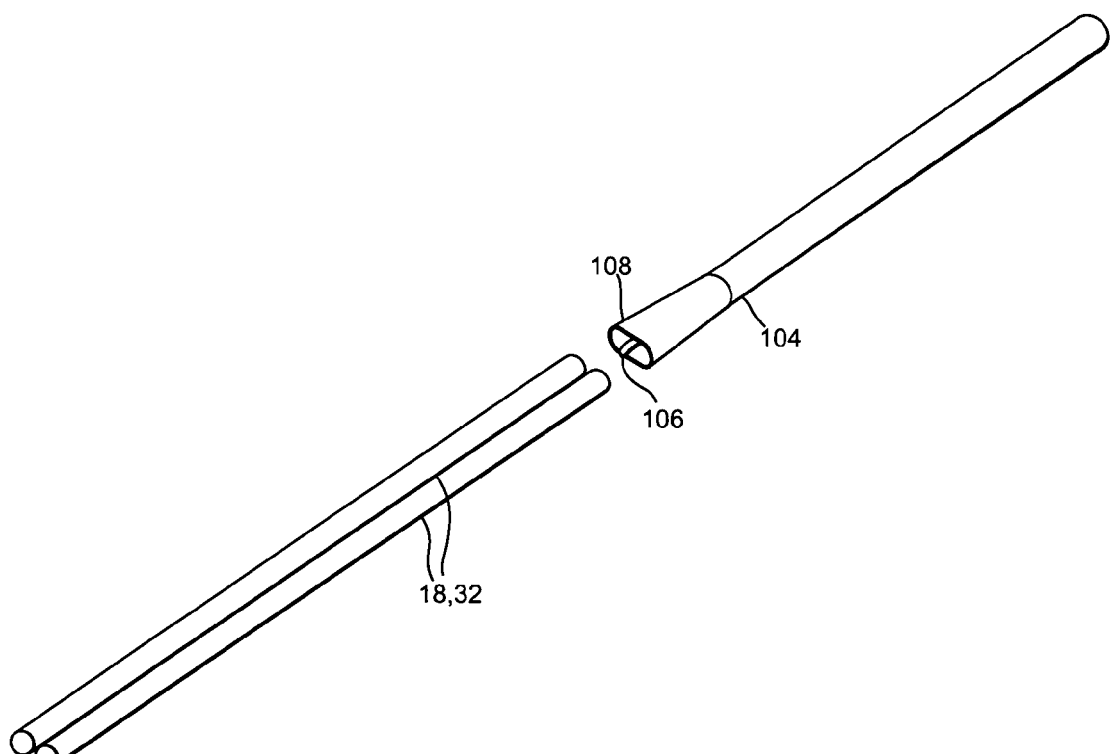

FIGS. 49A and 49B are perspective views of the retrieval device 104. The retrieval device 104 can include the hook 106 housed within the sheath 108. FIG. 48B also illustrates an embodiment of the tubes 18 and/or the insertion tool 32.

Figure 50A:
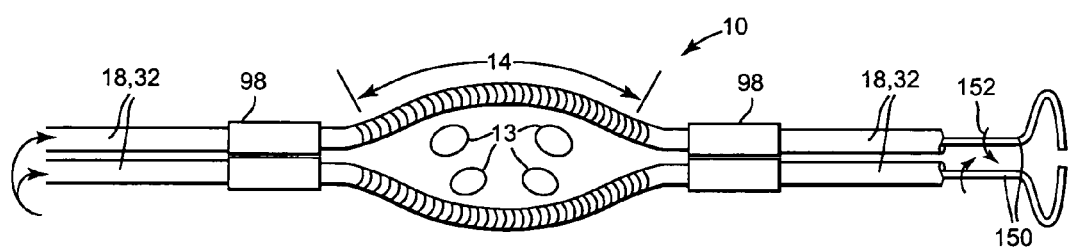
FIGS. 50A-50D are side, cross-sectional, and perspective views of an ablation apparatus according to one embodiment of the invention.
Figure 50C:
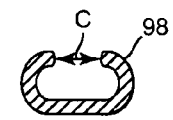
Figure 50B:
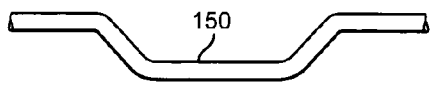
Figure 50D:
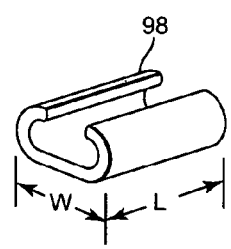

FIGS. 50A-50D illustrate an embodiment of an ablation apparatus 10 including rods 150 that can be used to tighten electrodes 14 with respect to the pulmonary veins 13. The ablation apparatus 10 can include tubes 18 and/or an insertion tool 32, along with clamps 98. Saline can be provided to the electrodes 14 via the tubes 18. FIG. 50B illustrates an embodiment of a rod 150 that can be inserted into the tubes 18. FIG. 50C illustrates an embodiment of a clamp 98 suitable for surrounding the tubes 18 and/or the insertion tool 32. The clamp 98 can have an oval configuration with a clearance C designed to receive the rods 150. FIG. 50D is a perspective view of the clamp 98. The width W of the clamp, in some embodiments, can be 0.6 cm and the length L of the clamp 98, in some embodiments, can be 0.75 cm. The clamps 98 can be moved with respect to the tubes 18 toward the pulmonary veins 13. The rods 150 can then be rotated as shown by the arrows 152 in FIG. 50A in order to tighten the electrodes 14 with respect to the pulmonary veins 13. In some embodiments, the clamps 98 can be positioned around the rods 150 after the rods 150 are already in place. In some embodiments, the clamps 98 can be fixed in place and/or can be prevented from twisting.

Figure 51:
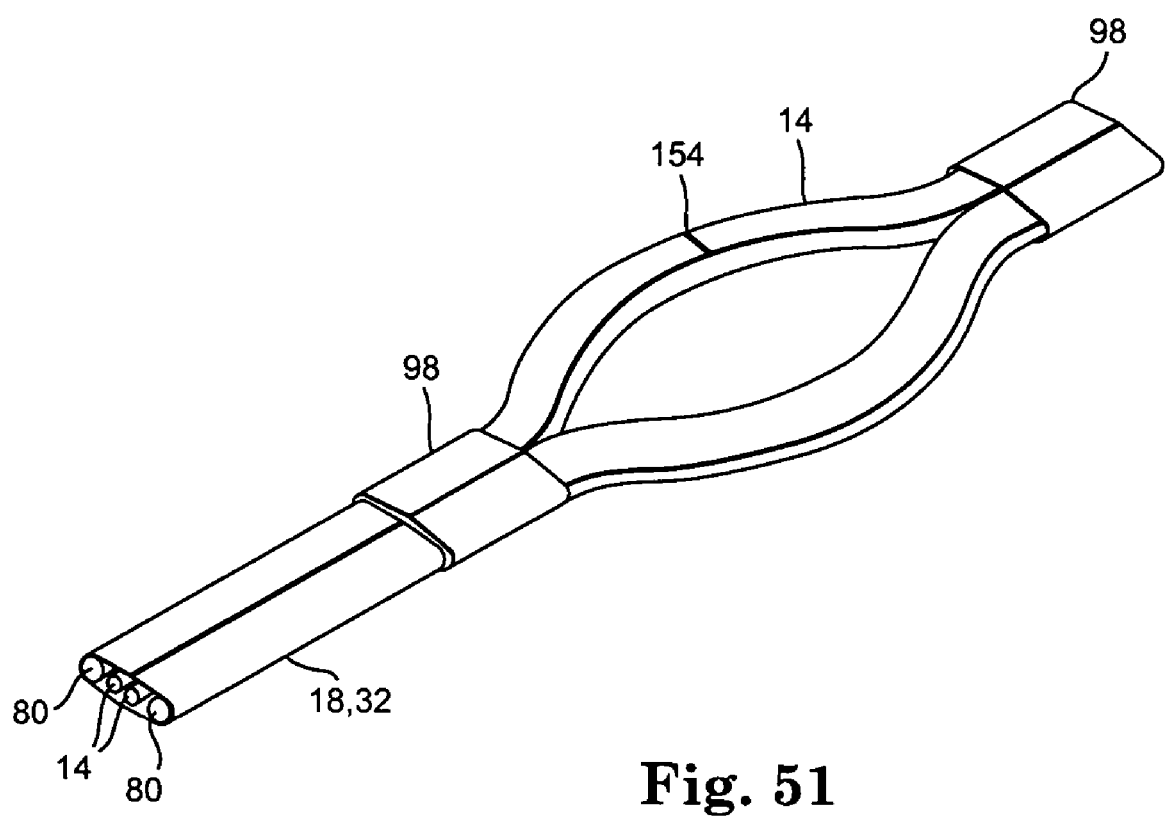
FIG. 51 is a perspective view of an ablation apparatus according to one embodiment of the invention.
Figure 52:
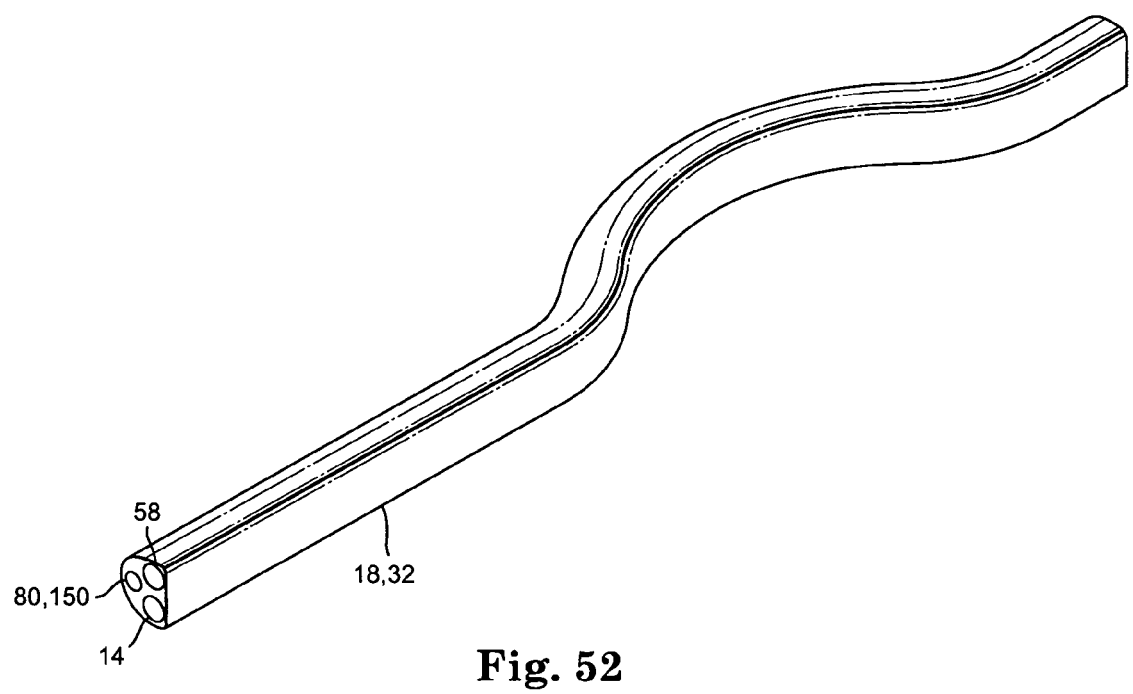
FIG. 52 is perspective view of a tube or insertion tool for use with an ablation apparatus according to one embodiment of the invention.

FIG. 51 is a perspective view of an ablation apparatus 10 including electrodes 14 that can be exposed to the target tissue 15 through an exposure slot 154. The ablation apparatus of FIG. 51 can also include clamps 98, tubes 18, and stiffeners 80. The tube 18 can include multiple channels in order to provide channels for the electrodes 14 that are separate from the channels for the stiffeners 80. FIG. 52 illustrates a single tube 18 and/or insertion tool 32, including a channel for electrodes 14, a channel 58 for saline, and a channel for a rod 150.

Figure 53A:
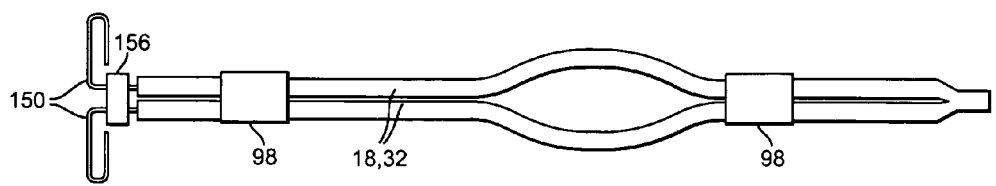
FIGS. 53A-53H are side, cross-sectional, and perspective views of an ablation apparatus according to one embodiment of the invention.
Figure 53C:
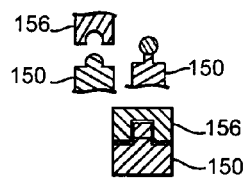
Figure 53B:
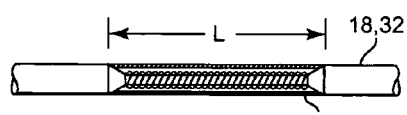
Figure 53G:
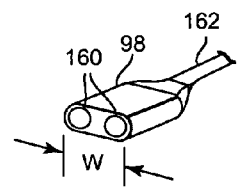
Figure 53D:
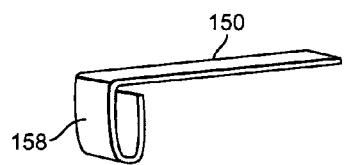
Figure 53F:
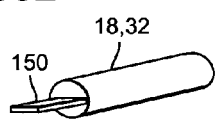
Figure 53E:
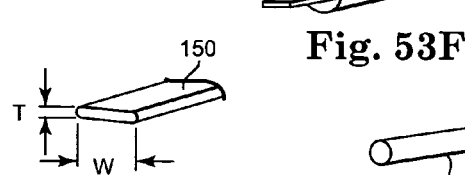
Figure 53H:
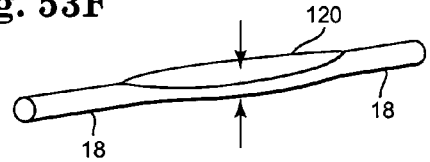

FIGS. 53A-53H illustrate an embodiment of an ablation apparatus 10 including stiffening rods 150 and a capture 156. The capture 156 can be used to lock the stiffening rods 150 in a closed position. As shown in FIG. 53B, tubes 18 and/or an insertion device 32 can include a length L for electrodes 14. The electrodes 14 can have a smaller diameter and can be wrapped in a coil configuration. The length L of the electrodes 14 can be approximately 8 mm to 10 mm. FIG. 53C illustrates embodiments of the capture 156 and the stiffening rods 150 including male protrusions and female recesses in order to couple the capture 156 to the stiffening rods 150. For example, the stiffening rods 150 can include a male protrusion with a circular shape or a rectangular shape and the capture 156 can include a correspondingly-shaped recess. FIG. 53D is a perspective view of the stiffening rods 150. The stiffening rods 150 can include a C-shaped handle 158. FIG. 53E is a perspective view of the cross-sectional profile of the stiffening rods 150 including a thickness T and a width W. The thickness T can be approximately 0.06 cm to approximately 0.09 cm, and the width W can be approximately 0.12 cm. FIG. 53F illustrates the tube 18 and/or the insertion tool 32 having a stiffening rod 150 disposed within an interior portion. FIG. 53G illustrates an embodiment of a clamp 98 for use with the ablation apparatus 10 of FIG. 53A. The clamp 98 can include recesses 160 for receiving multiple tubes 18. The clamp 98 can include a width W of approximately 10-12 mm. The clamp 98 can also combine the two tubes 18 into a single output lumen 162. FIG. 53H illustrates an embodiment of the tube 18 including a compressed portion 120 within which the electrodes can be positioned.

Figure 54A:
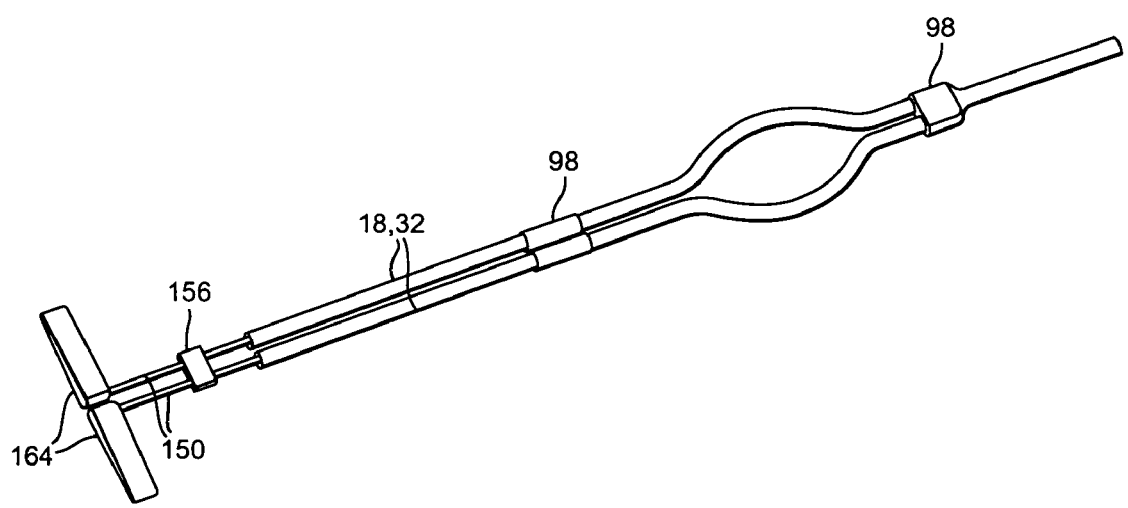
FIGS. 54A-54B are perspective views of an ablation apparatus according to one embodiment of the invention.
Figure 54B:
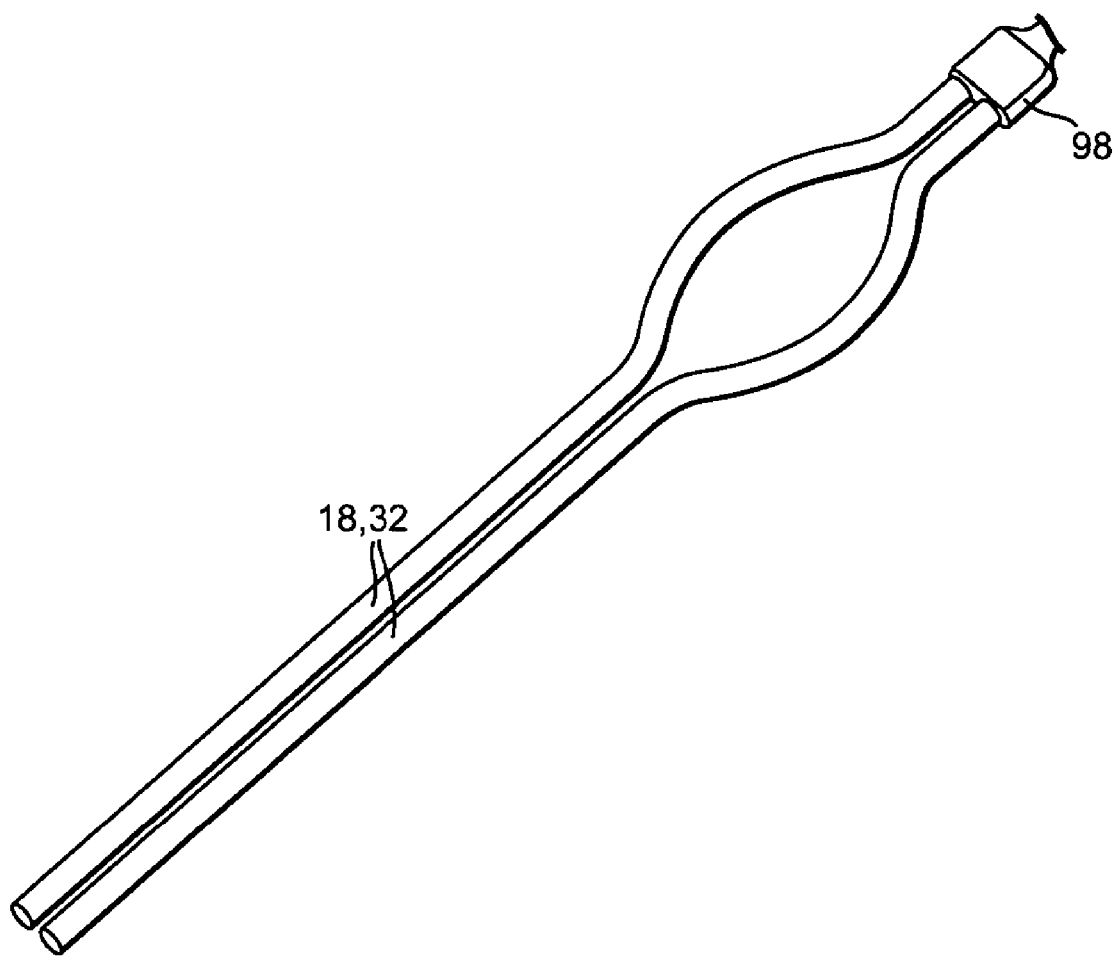

Similar to the embodiment shown in FIGS. 53A-53H, FIGS. 54A-54B illustrate an embodiment of the ablation apparatus 10, including a capture 156 positioned around stiffening rods 150. The stiffening rods 150 shown in FIG. 54A can include rectangular handles 164. The ablation apparatus 10 is shown in FIG. 54B without the stiffening rods 150 and the capture 156.

Figure 55A:
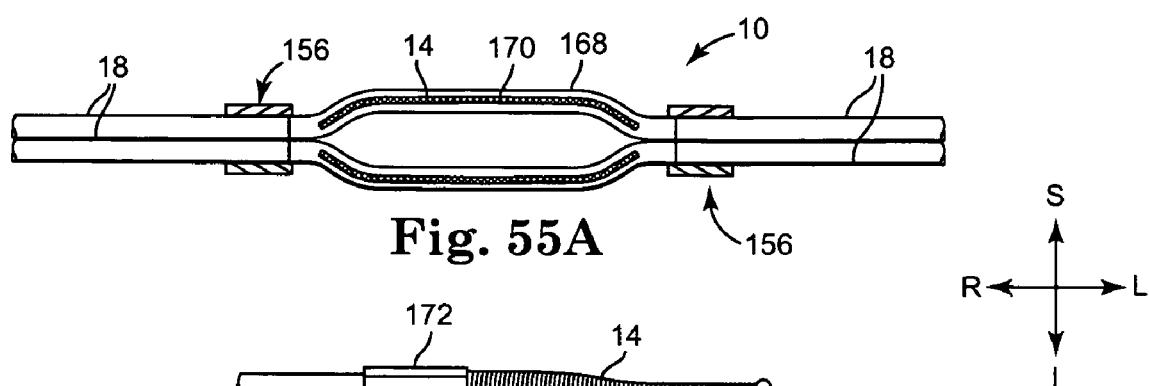
FIGS. 55A-55C are side and side cross-sectional views of an ablation apparatus according to one embodiment of the invention.
Figure 55B:
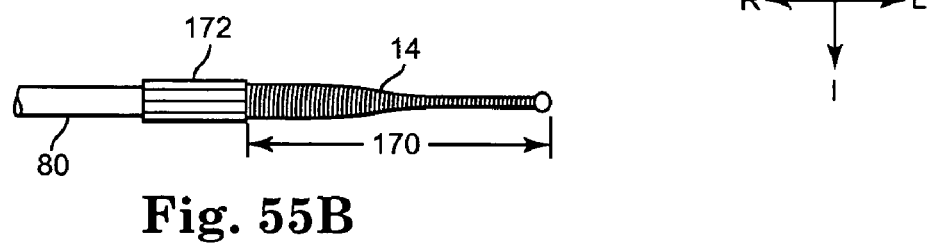
Figure 55C:
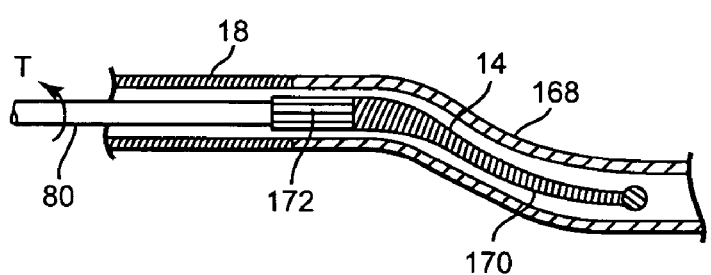

FIGS. 55A-55C illustrate an embodiment of the ablation apparatus 10 including a semi-rigid section 168, a flexible guide wire 170, and a hexagonal or square portion 172. As shown in FIG. 55B, a stiffener 80 can be coupled to the hexagonal or square portion 172 which can be coupled to the flexible guide wire 170. The electrodes 14 can include coils that can be wrapped around the flexible guide wire 170. The flexible guide wire 170 can have a larger diameter that decreases to a smaller diameter. FIG. 55C illustrates the flexible guide wire 170 and the hexagonal or square portion 172 inserted within the tube 18. The semi-rigid section 168 of the tube 18 can substantially surround the flexible guide wire 170 and the electrodes 14. The stiffeners 80 coupled to the hexagonal or square portion 172 can be rotated according to a torque T. The hexagonal or square portion 172 can drive the semi-rigid section 168. The hexagonal or square portion 172 can engage with the semi-rigid section 168 in order to drive the semi-rigid section 168 to clamp the atria. The flexible guide wire 170 can help maneuver the stiffener 80 through the flexible tubes 18 into the semi-rigid section 168. The ablation apparatus 10 shown in FIG. 55A can also include one or more captures 156. The ablation apparatus 10 can also receive saline through the tubes 18.

Figure 56A:
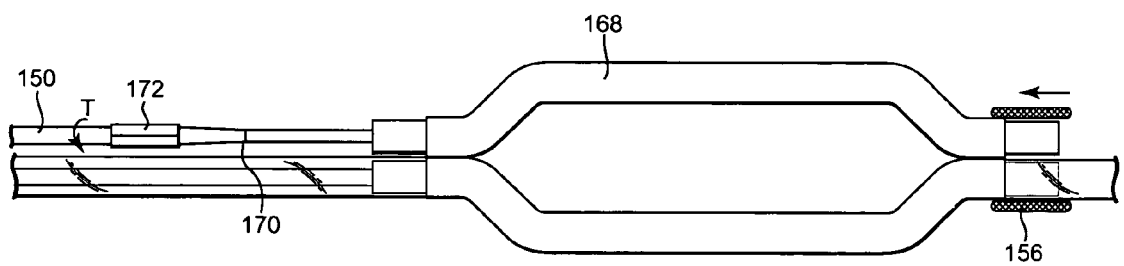
FIGS. 56A-56E are side, solid-view perspective, and frame perspective views of an ablation apparatus according to one embodiment of the invention.
Figure 56B:
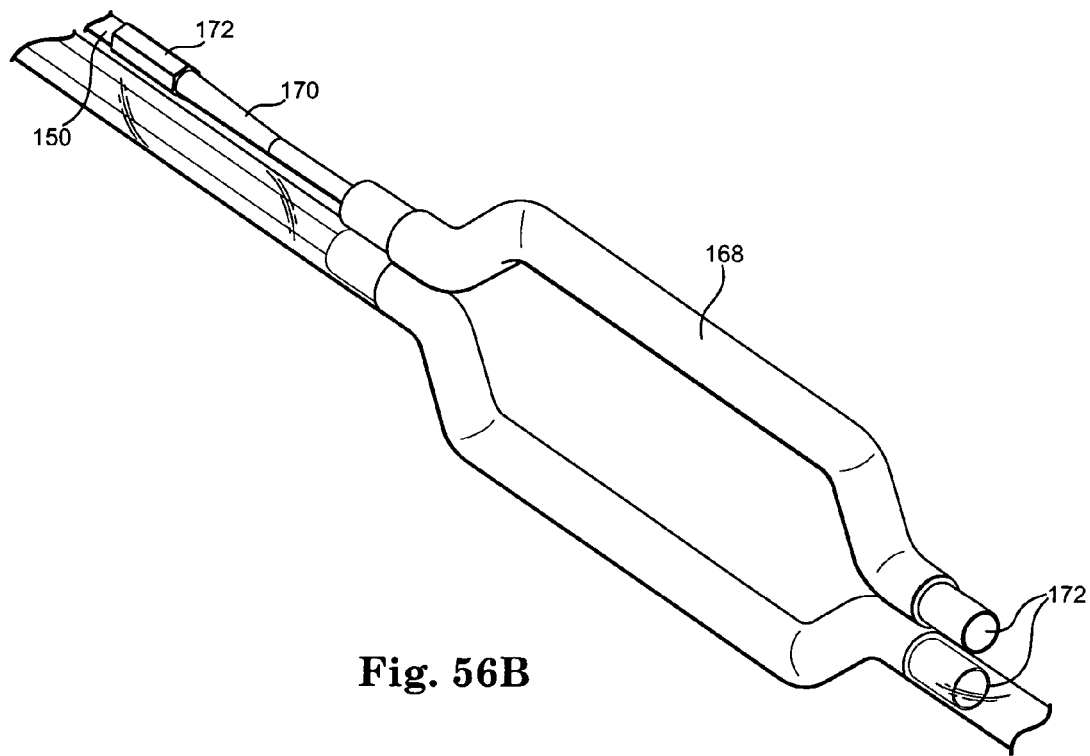
Figure 56C:
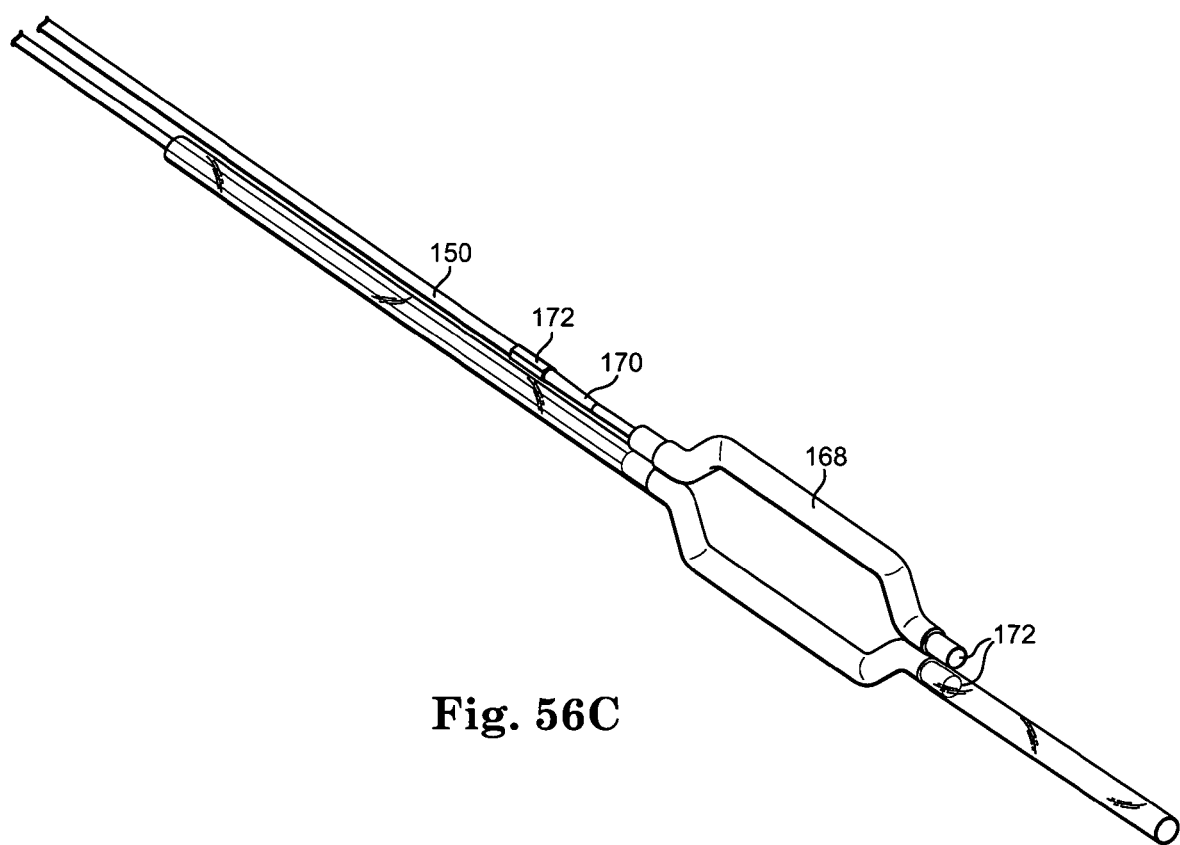
Figure 56D:
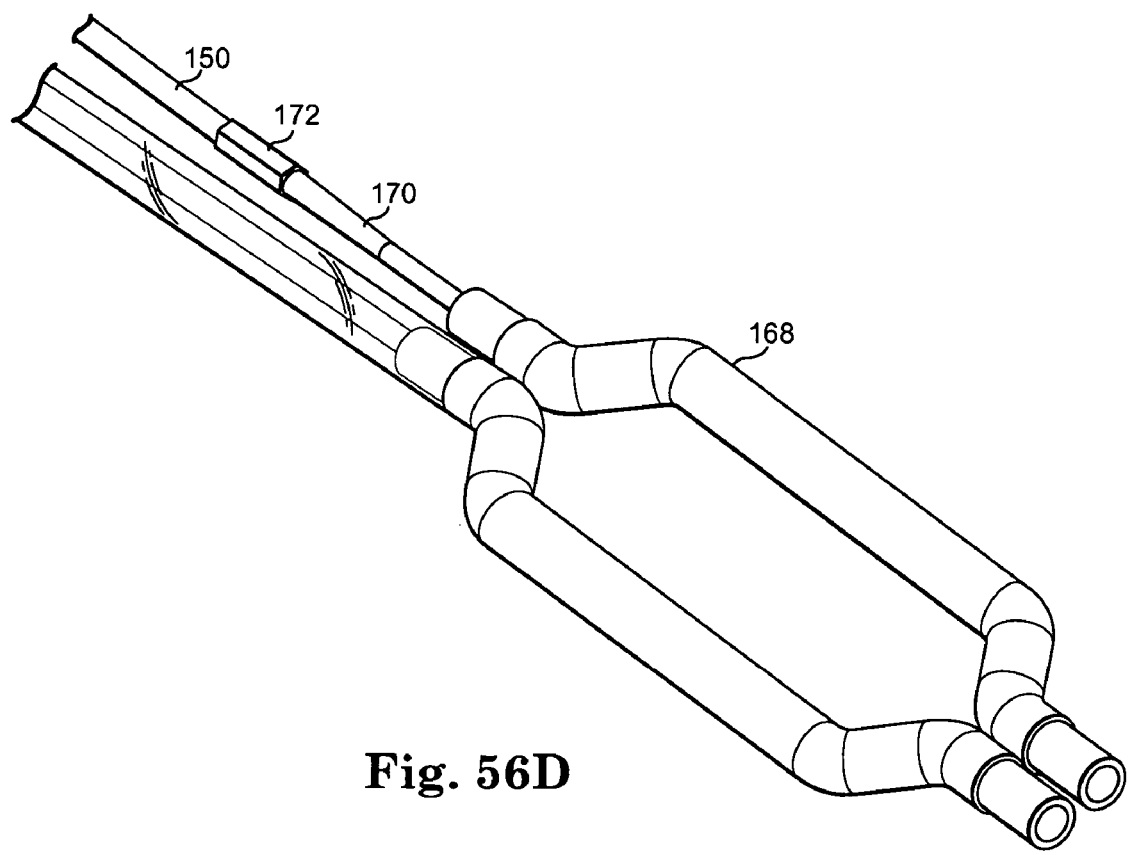
Figure 56E:
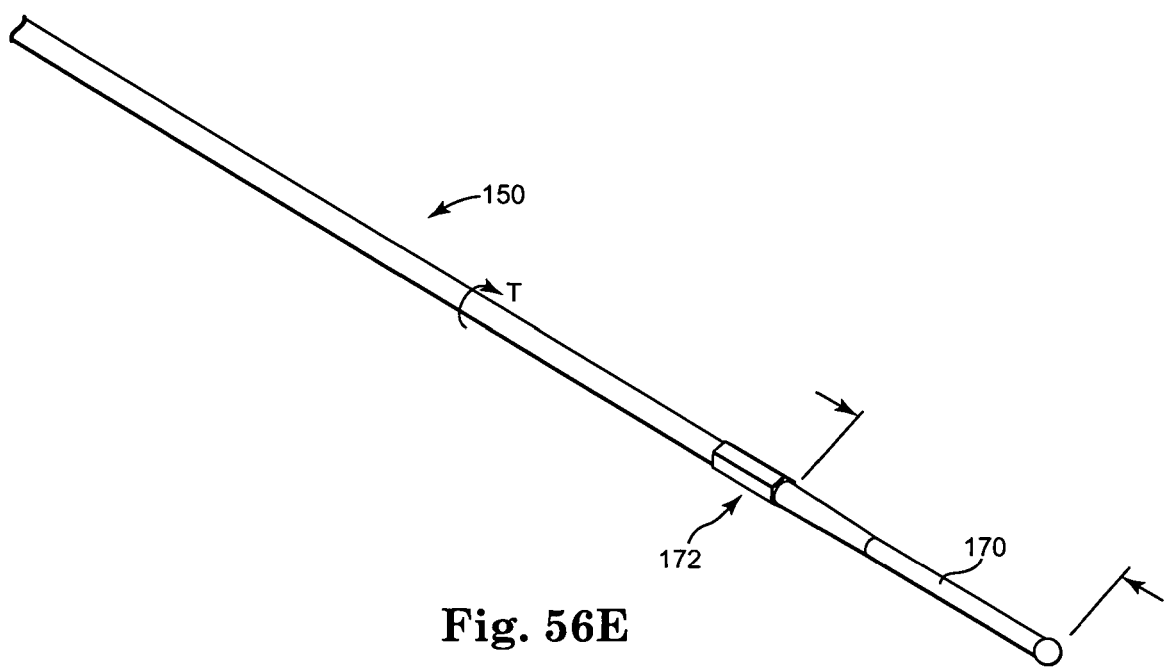

FIGS. 56A-56E are side and perspective views of the ablation apparatus 10, including the semi-rigid section 168, the flexible guide wire 170, and the hexagonal or square portion 172. As shown in FIG. 56A, the ablation apparatus 10 can also include the capture 156. The rods 150 can be coupled to the hexagonal or square portion 172 and can be rotated according to the torque T. The hexagonal or square portion 172 can engage with the semi-rigid portion 168 in order to drive the semi-rigid portion 168 closed via the torque T through the rod 150. The semi-rigid section 168 can also be referred to as a clamp frame. The capture 156 can slide onto the semi-rigid portion or the clamp frame 168 in order to clamp the segments of the clamp frame 168 together during the clamping of the atria. One capture 156 can be used at each end of the clamp frame 168. FIG. 56D illustrates a frame assembly for the clamp frame 168. FIG. 56E illustrates the stiffening rod 150 including the hexagonal or square portion 172 and the flexible guide wire 170. The flexible guide wire 170 can assist with maneuvering the stiffening rod 150 through the flexible tube 18 connected to the clamp frame 168, as shown in FIGS. 56A through 56D. The stiffening rode 150 can drive the clamp frame 168 closed with the applied torque T. The stiffening rod 150 can be constructed of a flexible shaft that can transmit adequate torque over approximately 300 mm.

Figure 57A:
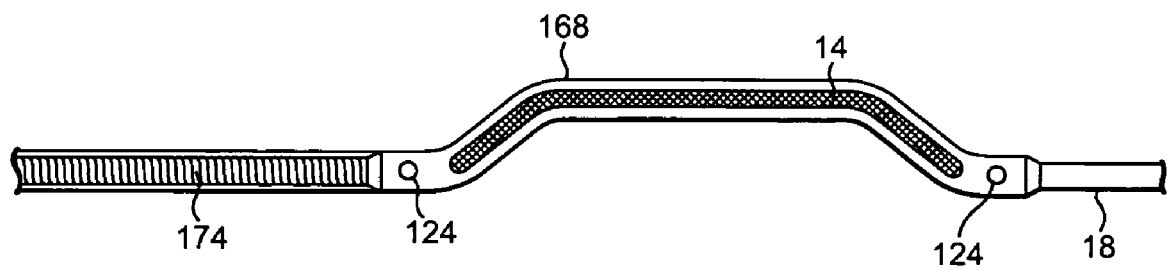
FIGS. 57A-57B are side views of an ablation apparatus according to one embodiment of the invention.
Figure 57B:
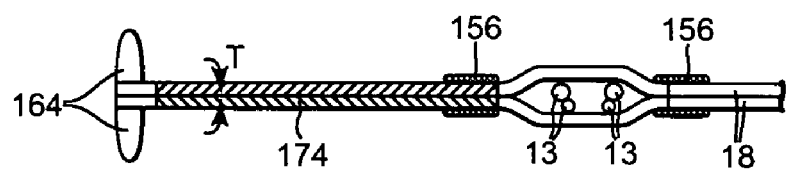

FIGS. 57A and 57B illustrate an embodiment of the ablation apparatus 10, including light markers 124 and a flexible shaft 174. The flexible shaft 174 can be coupled to or independent of the stiffening rods 150. The flexible shaft 174 can be a power transmissive shaft. The flexible shaft 174 can be fixed to or detachable from the clamp frame 168. The ablation apparatus 10 can also captures 156, as shown in FIG. 57B. The light markers 124 can include fiber optic light outputs for indicating the position of the clamp frame 168 and the electrodes 14. Tubes 18 can be coupled to the clamp frame 168, and can receive saline and an energy input. The flexible shaft 174 can be rotated using rectangular handles 164 in order to provide a torque T.

Figure 58A:
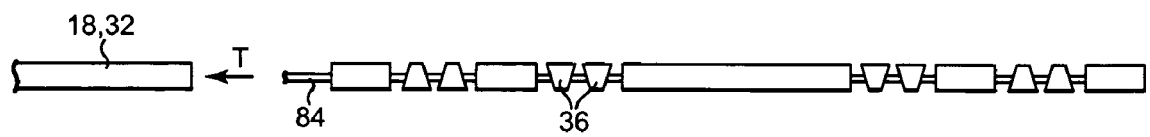
FIGS. 58A-58E are side and cross-sectional views of an ablation apparatus according to one embodiment of the invention.
Figure 58B:
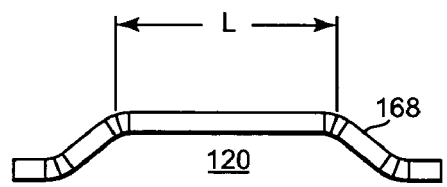
Figure 58C:
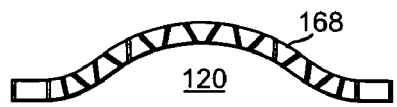
Figure 58D:
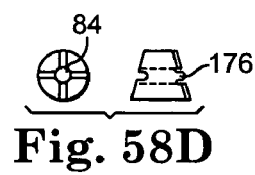
Figure 58E:
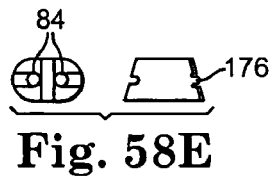

FIGS. 58A-58E illustrate another embodiment of the ablation apparatus 10, including several articulating segments 36. The articulating segments 36 can be coupled to a connecting cable 84. FIGS. 58B and 58C illustrate the clamp frame 168 configured using a plurality of articulating segments 36. FIG. 58D illustrates one embodiment of a cross-sectional profile for each articulating segment 36. FIG. 58E illustrates another embodiment of a cross-sectional profile for each articulating segment 36, including two connecting cables 84. FIGS. 58D and 58E also illustrate tabs 176 that can be used to interlock adjacent articulating segments 36. As shown in FIGS. 58A and 58B, each articulating segment 36 can have a particular shape, such as rectangular shape, an elongated rectangular shape, and a polygon shape. FIG. 58A illustrates a tube 18 and/or an insertion tool 32 that can receive the articulating segment 36 and the connecting cable 84. The tube 18 and/or the insertion tool 32 can be constructed of a relatively rigid material to handle compression that results from tension in the connecting cable 84. FIG. 58B illustrates that the clamp frame 168 can include a length L that defines a clamping area 120. The length L, in some embodiments, can be approximately 6 cm to 8 cm. As shown in FIG. 58A, tension T placed on the cable 84 can pull the articulating segments 36 together in order to create a shape for the clamp frame 168, as shown in FIGS. 58B and 58C.

Figure 59A:
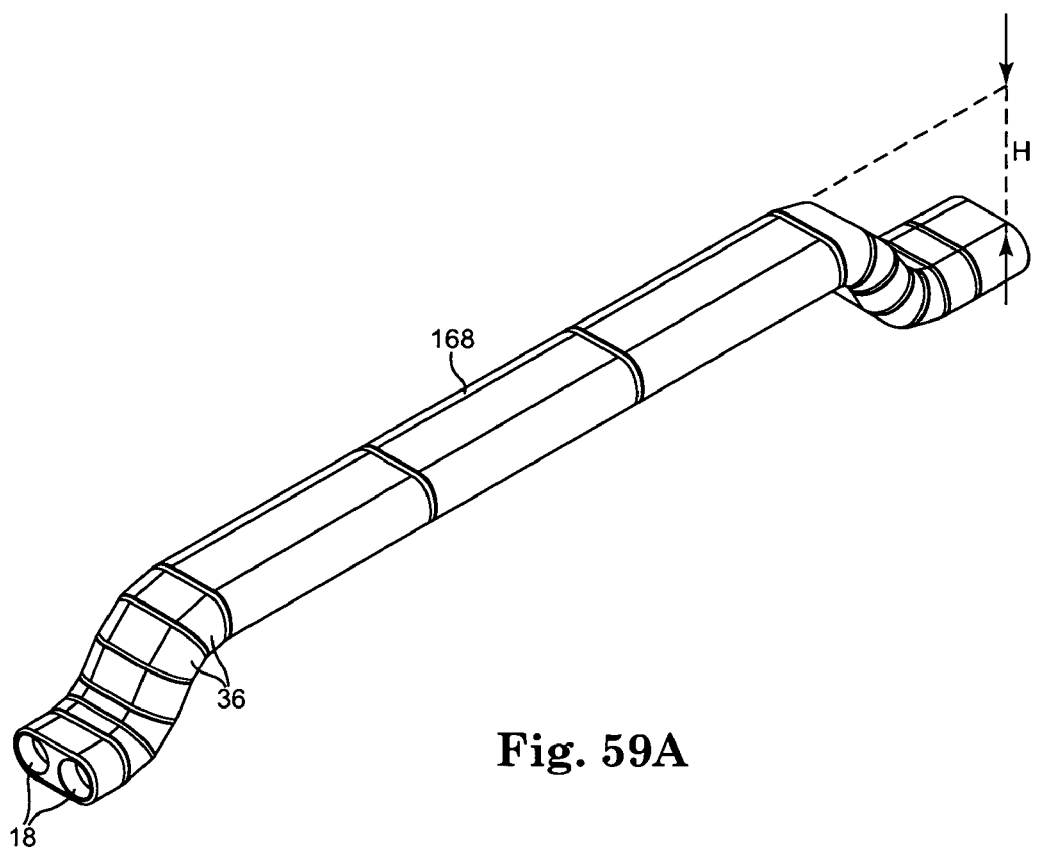
FIGS. 59A-59B are frame perspective and solid-perspective views of an ablation apparatus according to one embodiment of the invention.
Figure 59B:
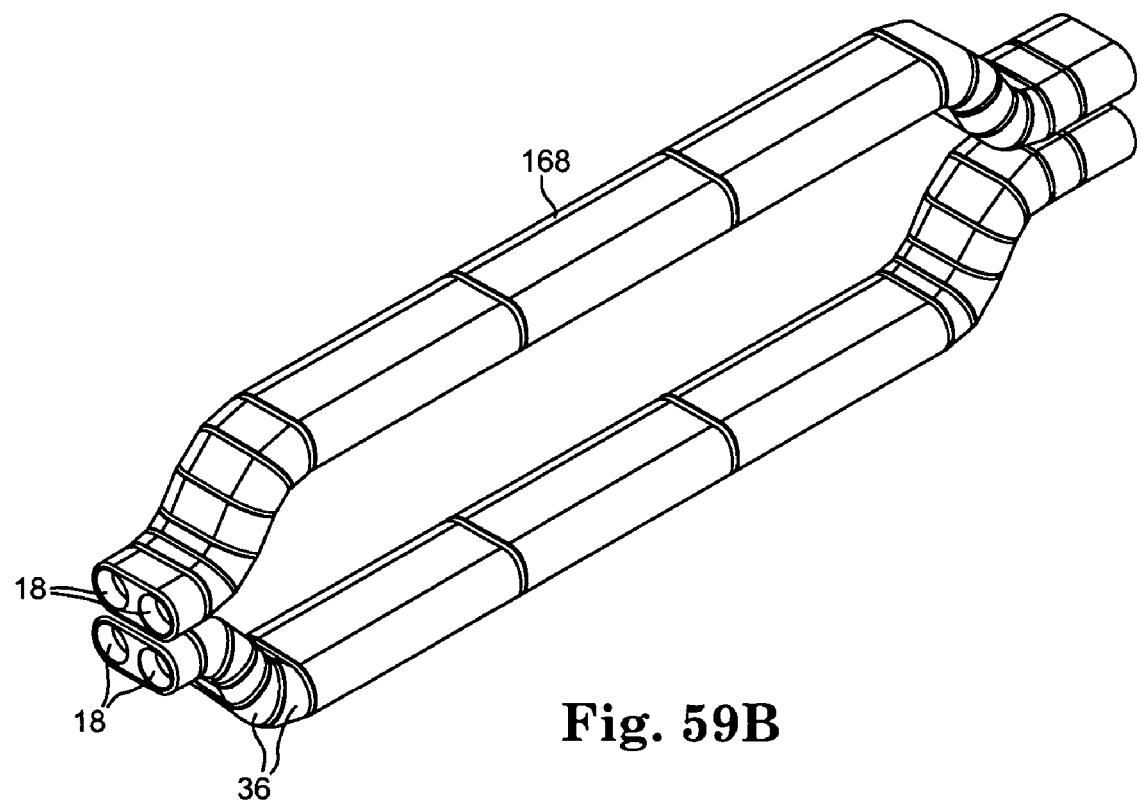

FIGS. 59A and 59B illustrate an embodiment of the clamp frame 168, including articulating segments 36. The clamp frame 168 can also include two tube portions 18. One tube 18 can be used as a saline channel 58, while the other tube 18 can be used to receive electrodes 14. The clamp frame 168 can include a height H of approximately 11 mm.

Figure 60A:
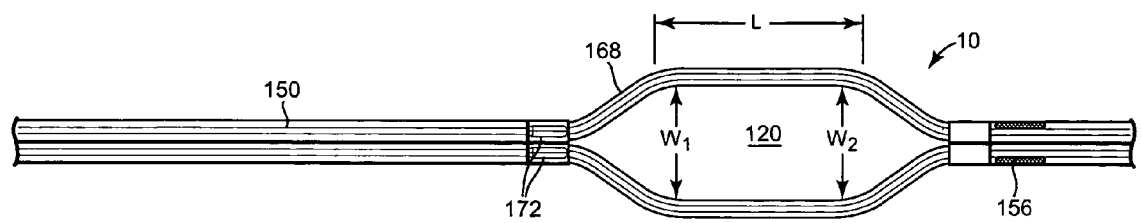
FIGS. 60A-60B are side views of an ablation apparatus according to one embodiment of the invention.
Figure 60B:
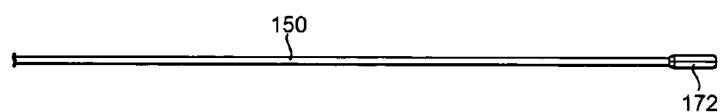

FIGS. 60A and 60B illustrate an embodiment of the ablation apparatus 10 including a clamp frame 168, a stiffening rod 150, and a hexagonal or square portion 172. The clamp frame 168 can include a length L, which in some embodiments, can be approximately 5 cm. The clamp frame 168 can also define a clamping area 120, including a first width $W_1$ and a second width $W_2$. The first width $W_1$ can be approximately 2.5 cm, and the second width $W_2$ can be approximately 2.3 cm. The ablation apparatus 10 of FIG. 60A can also include a capture 156. FIG. 60B illustrates the stiffening rod 150 including the hexagonal or square portion 172, which can be inserted into a tube 18 as shown in FIG. 60A. The stiffening rod 150, in some embodiments, can be approximately 0.093 cm in diameter. The stiffening rod 150 can be inserted into a proximal end of the tube 18, while the capture 156 can be positioned at a distal end of the ablation apparatus 10. The hexagonal or square portion 172 can mate with a corresponding recess within the clamp frame 168.

FIGS. 61A through 61G illustrate an ablation apparatus 10 that can include a distal area 178 designed according to one or more of the embodiments shown in FIGS. 61B-61D. For example, FIG. 61B illustrates a clamp frame 168 including two segments joined by a connecting cable 84. FIG. 61C illustrates a clamp frame 168 including two segments connected by one or more magnets 180. FIG. 61D illustrates a capture clamp 182 which can be coupled to two segments of the clamp frame 168. The ablation apparatus 10 of FIG. 61A can also include tubes 18, stiffening rods 150, hexagonal- or square-shaped portions 172, and flexible guide wires 170. The flexible guide wires 170 can be positioned into the tubes 18. The ablation apparatus 10 can also include a capture 156 coupled to the tubes 18. In some embodiments, the stiffening rods 150 are constructed of a flexible drive shaft material. The distal area 178 can be designed to provide access to the patient from the right side, and can include rigid section leads. The distal area 178 can also be designed for access to the patient's left side, and can include flexible section leads. The embodiments of the clamp frame 168 shown in FIGS. 61B-61D can be provided to capture proximal ends of the flexible tubes 18. FIG. 61B includes a connecting cable 84 that can be positioned through the tubes and the clamp frame 168, and can be drawn into tension from the proximal end of the tubes 18. In the embodiment shown in FIG. 61B, the flexible tubes 18 are constructed of a non-compressible material. As shown in FIG. 61E, the clamp frame sections 168 can pivot with respect to one another. The magnets 180 shown in FIG. 61C can aid in positioning and/or aligning the clamp frame 168 sections. FIGS. 61F and 61G illustrate cross-sectional profiles for the sections of the clamp frame 168, such as a circular configuration coupled to a half moon configuration or two semicircular configurations. The embodiment of the capture clamp 182 shown in FIG. 61D can, in some embodiments, be removed from the left side of the patient.

Figure 62:
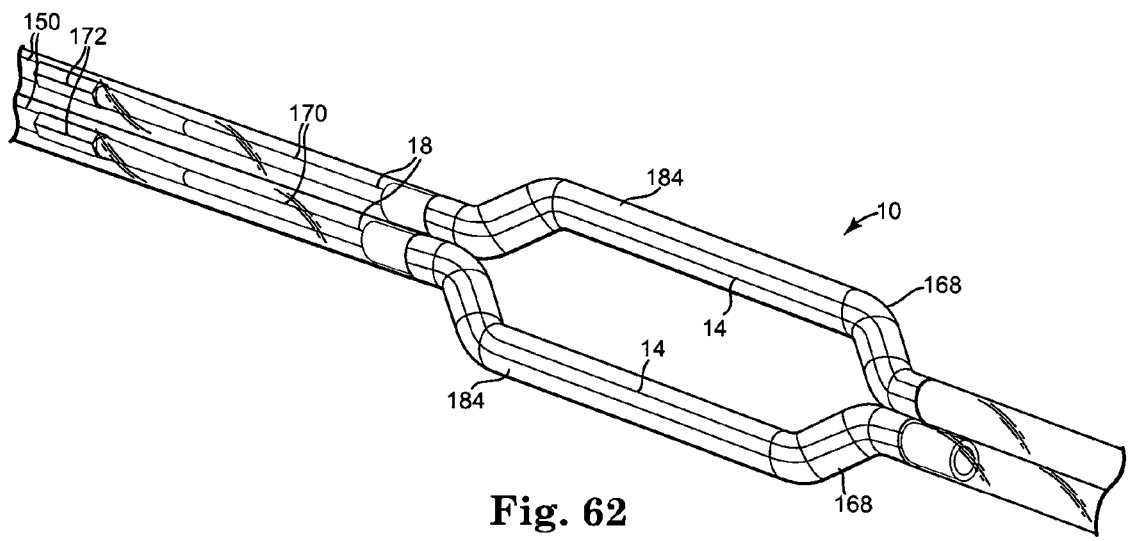
FIG. 62 is a perspective view of an ablation apparatus according to one embodiment of the invention.

FIG. 62 illustrates an embodiment of the ablation apparatus 10 including grooves 184 within which electrodes 14 can be received. The grooves 184 can be located along the length of the clamp frame 168. Stiffening rods 150 including hexagonal-shaped or square-shaped portions 172 and flexible guide wires 170 can be inserted into tubes 18 coupled to the clamp frame 168.

Figure 63A:
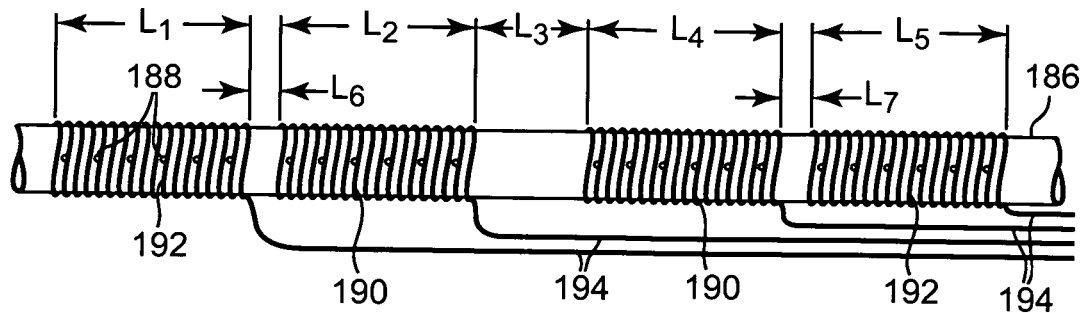
FIGS. 63A-63C are side and cross-sectional views of an ablation apparatus according to one embodiment of the invention.
Figure 63B:
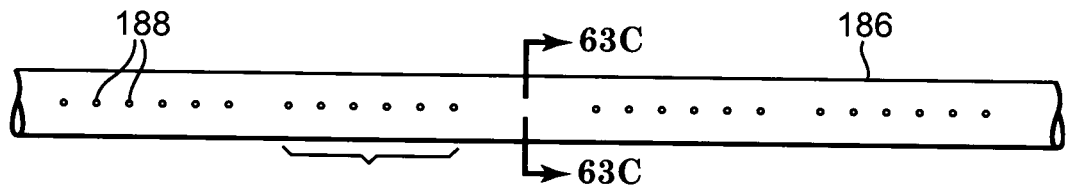
Figure 63C:
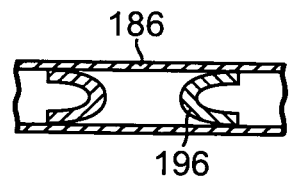

FIGS. 63A-63C illustrate an embodiment of an ablation apparatus 10 including a catheter 186. The catheter 186 can include a series of holes 188. Distal coils 190 can be wrapped around the catheter 186, along with proximal coils 192. The series of holes 188 can be placed along the length of the catheter 186, so that approximately six holes are positioned beneath each coil 190, 192. The coils 190, 192 can be secured to the catheter 186 by any suitable means, such as an ultraviolet curing adhesive. The catheter 186 can be constructed of a latex material, in some embodiments. One or more leads 194 can be connected between the coils 190, 192 and a conductor. Each one of the holes 188 can be approximately 0.03 cm in diameter. Each set of coils can be positioned along the length of the catheter 186 according to several lengths $L1_1$, $L_2$, $L_4$, and $L_5$, each of which can be approximately 4 cm long. A space $L_3$ can exist between the distal set of coils 190, and the space $L_3$ can be approximately 2 cm. Spaces can also exist between the distal coils 190 and the proximal coils 192, and those spaces $L_6$ and $L1_7$ can be approximately 2 mm. FIG. 63C is a cross-sectional view of the catheter 186 along the line 63C-63C of FIG. 63B. The cross section can include two C-shaped tips which, in some embodiments, can be removed from the catheter 186.

Figure 64A:
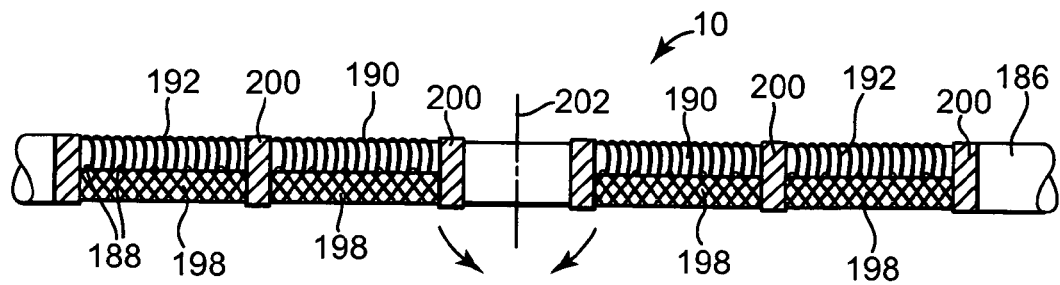
FIGS. 64A-64D are side and cross-sectional views of an ablation apparatus according to one embodiment of the invention.
Figure 64B:
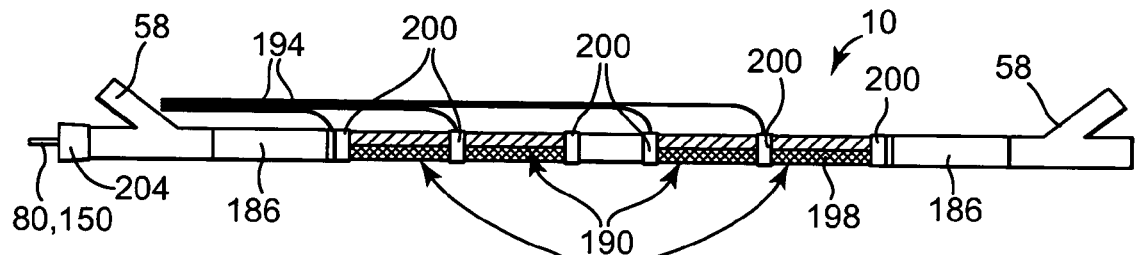
Figure 64C:
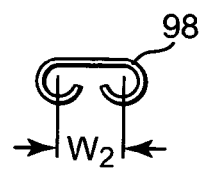
Figure 64D:
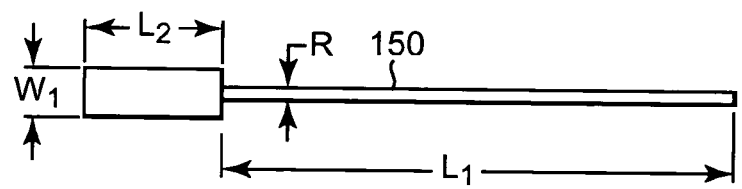

FIGS. 64A-64D illustrate an embodiment of the ablation apparatus 10 similar to the embodiment shown in FIGS. 63A-63B. In addition, the embodiment shown in FIGS. 64A-64D can include ablation faces 198 and shrink tube sections 200. As shown in FIG. 64A, the ablation apparatus 10 can include several shrink tube sections 200, each one of the shrink tube sections 200 positioned on either side of a coil 190, 192. The coils 190, 192 and the ablation faces 198 can be positioned between any two of the shrink tube sections 200. The catheter 186 can be folded along line 202. As shown in FIG. 64B, the ablation apparatus 10 can also include one or more saline channels 58, one or more septums 204, and one or more stiffeners 80. The ablation faces 198 can, in some embodiments, be constructed of ePTFE. The coils 190, 192 and/or the ablation faces 198 can be coupled to the catheter 186 with ultraviolet curing adhesive (e.g., before silicone is applied). In some embodiments, silicone can be used as a covering over the coils 190, 192 and to secure the ablation faces 198. FIG. 64B illustrates several conductors 194 connected to the coils 190, 192. The conductors 194 can be mated with banana plugs, in some embodiments. The catheter 186 can be clamped in its folded position using a clamp 98 as shown in FIG. 64C. The clamp 98 can include a width $W_2$ equal to approximately 12 mm, in some embodiments. The clamp can be constructed of wire having a 0.06 mm radius, in some embodiments. FIG. 64D illustrates an embodiment of the stiffener 80, including a width $W_1$, a handle length $L_2$, a radius R and an insertion length $L_1$. The width $W_1$ can be equal to approximately 0.38 mm, the length $L_1$ can be equal to approximately 11 cm, the length $L_2$ can be approximately 1.25 mm, and the radius R can be approximately 0.093 mm. In some embodiments, two stiffening rods 150 can be used in conjunction with the catheter 186.

FIGS. 65A-65E illustrate an embodiment of the ablation apparatus including a clamp system 206. The clamp system 206 can include a core 208, jaws 210, and supports 212. The supports 212 can connect the core 208 to the jaws 210. The clamp system 206 can be introduced into the patient's body using an insertion tool 32, such as an ablation catheter or a guide catheter, that can be placed through the sinuses before the clamp system 206 is introduced into the body. One or more portions of the clamp system 206 can be coupled to the tubes 18. The tubes 18 can move or the core 208 can be retracted to actuate the jaws 210. FIGS. 65B and 65C illustrate electrodes 14 coupled to the jaws 210. The electrodes 14 can extend along a length L of the jaws 210. The jaws 210 can thus provide a structure for mounting the electrodes 14. The insertion tool 32 can function as a guide for the placement of the electrodes 14 via the jaws 210. FIG. 65E is a partial perspective view of a tube 18 suitable for use with the ablation apparatus 10 of FIG. 65A. The tube 18 can include a first channel and a second partially-open channel. The second partially-open channel can engage a portion of the clamp system 206.

Figure 66A:
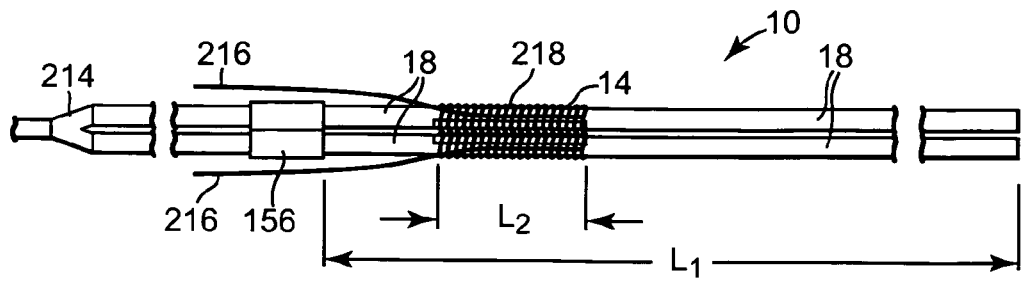
FIGS. 66A-66G are side and perspective views of an ablation apparatus according to one embodiment of the invention.
Figure 66B:
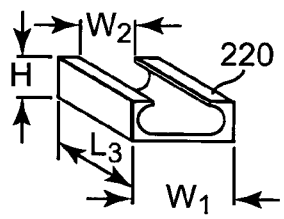
Figure 66C:
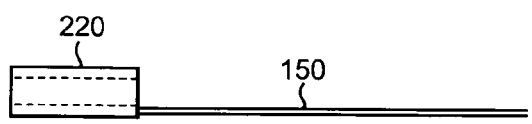
Figure 66D:
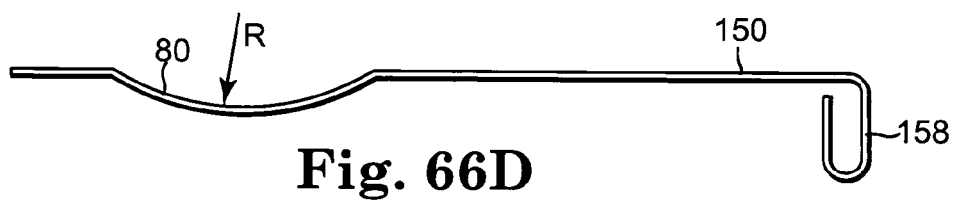
Figure 66F:
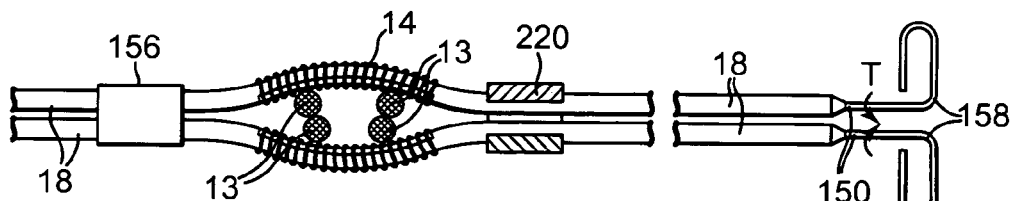
Figure 66E:
Figure 66G:
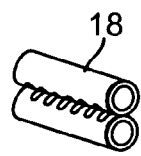

FIGS. 66A-66F illustrate an embodiment of the ablation apparatus 10 including a Y-shaped connector 214, one or more leads 216, and a silicone cover 218. The silicone cover 218 can wrap around electrodes 14. The ablation apparatus 10 can also include a fixed capture 156 and a moveable capture 220. FIG. 66F illustrates the moveable capture 220 placed toward the pulmonary veins 13 and the electrodes 14. FIG. 66B illustrates the moveable capture 220 including a width $W_1$ of approximately 0.8 cm, a slot width $W_2$ of approximately 0.19 cm, a length $L1_3$ of approximately 1 cm, and a height H of approximately 0.5 cm. FIG. 66E is a side view of the moveable capture 220 coupled to a rod 150. FIG. 66A illustrates an electrode length $L_2$ of approximately 3 cm to 4 cm, and a tube length $L_1$ of approximately 30 cm to approximately 35 cm. In some embodiments, the length $L_2$ can be approximately 8 cm to approximately 10 cm. The tubes 18 shown in FIG. 66A can, in some embodiments, be constructed of polyvinyl chloride, and can have an inner diameter of 125 mm and an outer diameter of 0.25 cm. FIG. 66G illustrates an embodiment of the tubes 18 including two channels. As shown in FIG. 66G, the tubes 18 can have an inner diameter of 0.25 cm and an outer diameter of 0.312 cm. FIG. 66D illustrates an embodiment of a stiffening rod 150 including a C-shaped handle 158 and a stiffener 80 with a minimum radius R. FIG. 66E illustrates a suitable cross-sectional profile for the tubes 18, including a conductor 16, an electrode 14, a stiffener 80, and a saline channel 58. In some embodiments, the tubes 18 can be constructed of urethane or Pebax. In some embodiments, the tubes 18 can be soldered together. In some embodiments, the stiffening rod 150 as shown in FIG. 66C can include a diameter of approximately 0.093 cm. In some embodiments, saline can be provided to the electrodes 14 via the Y-shaped connector 214. FIG. 66F illustrates the stiffening rods 150 upon which a torque T can be applied in order to rotate the stiffening rods 150 to clamp the electrodes 14 with respect to the atria. The minimum radius R shown in FIG. 66D can allow blood flow until the stiffening rods 150 are fully positioned and the electrodes 14 are ready to ablate the target tissue 15. Rotating the rods can clamp the atria and stop or reduce blood flow through the pulmonary veins 13.

In some embodiments, the clamping area 102 of the ablation apparatus 10 can include multiple zones that can be clamped sequentially to allow for a single set of pulmonary veins 13 to be opened during ablation. In some embodiments, the clamping area 102 can be tailored to a specific segment of the population, such as having different sized clamping areas 102 for males and females.

Figure 67A:
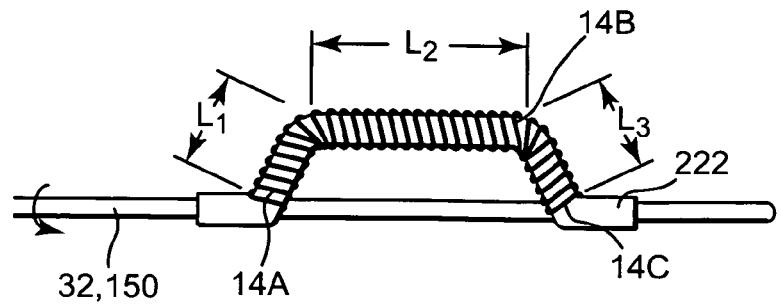
FIGS. 67A-67G are side and schematic views of an ablation apparatus according to one embodiment of the invention.
Figure 67B:
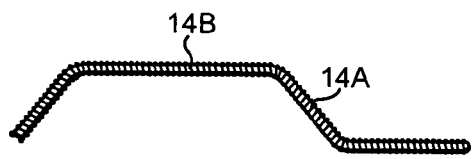
Figure 67C:
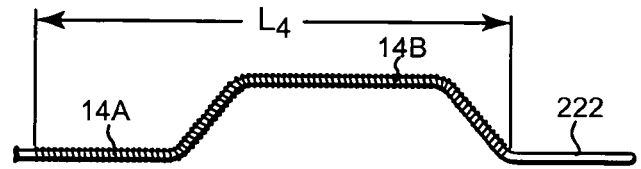
Figure 67D:
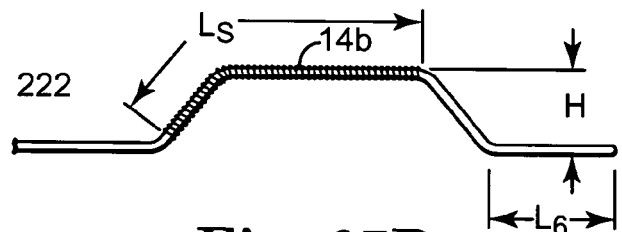
Figure 67E:
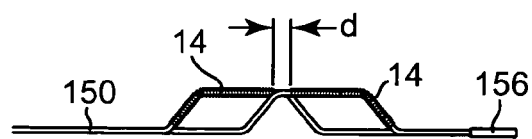
Figure 67F:
Figure 67G:
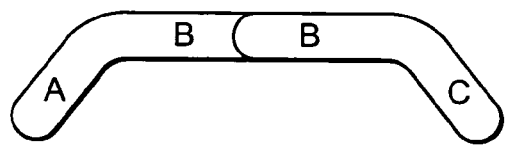

FIGS. 67A-67G illustrate an embodiment of the ablation apparatus 10 including a moveable core 222 with active and inactive sets of electrodes 14. As shown in FIG. 67A, the moveable core 222 can be slideably coupled to an insertion tool 32 or a stiffening rod 150. The moveable core 222 can have coil electrodes 14 wrapped around its surfaces. The electrodes 14 can be positioned along the length of the moveable core 222 according to multiple lengths $L_1$, $L_2$, and $L_3$. In some embodiments, lengths $L_2$ and lengths $L_3$ can be activated in order to ablate target tissue 15 near the left pulmonary veins 13. In some embodiments, the lengths $L_1$ and $L_2$ can be used activated in order to ablate target tissue 15 near the right pulmonary veins 13. The several lengths of electrodes 14 can be activated independently of one another according to the particular target tissue 15. The moveable core 222 can move along the length of the insertion tool 32 or the stiffening rods 150. FIGS. 67B and 67C illustrate an embodiment of the moveable core 222 including inactive electrodes 14A and active electrodes 14B. As shown in FIG. 67C, a total length $L_4$ for the active and inactive electrodes 14A, 14B can be approximately 60 mm to approximately 80 mm. FIG. 67D illustrates a length of active electrode 14B. The moveable core 222 can include a length $L_5$ around which the electrode 14B can be wrapped, a height H, and a length $L_6$. FIG. 67E illustrates multiple insertion tools 32 or stiffening rods 150 with electrodes 14 wrapped around them. The stiffening rods 150 can also be coupled to one another with a capture 156. The stiffening rods 150 can be spaced apart from one another but can create an overlapping distance d. In this manner, dual rods 150 can be used for each leg of a loop 12. A bend configuration can be used for the moveable core 222 in order to allow each stiffening rod 150 to be moved independently. Only one stiffening rod 150 should clamp on the atrium at any given time, in one embodiment of the invention. FIG. 67F illustrates a cross-sectional profile of the insertion tool 32 or the stiffening rod 150. In some embodiments, the moveable core 222 requires that the insertion tool 32 or the stiffening rods 150 do not stretch or compress significantly during movement of the moveable core 222. In some embodiments, the moveable core 222 can require precise indexing, for example, six sigma indexing, for the distal and proximate positions of the moveable core 222 along the insertion tool 32 or the stiffening rod 150. FIG. 67G illustrates one embodiment of overlapping active and inactive electrodes 14A and 14B with three separate segments, A, B, and C. The segment AB can be used for a second ablation, while the segment BC can be used for a first ablation.

In some embodiments, rather than using stiffening rods 150, a flexible power transmission shaft can be used. This flexible shaft can be fixed or detachable to a clamp frame 168. Rotating two flexible shafts in opposite directions can close the clamp frame 168 on the atria. In some embodiments, small light markers 124 can aid in confirming the placement of the electrodes 14 in the closed chest.

Figure 68A:
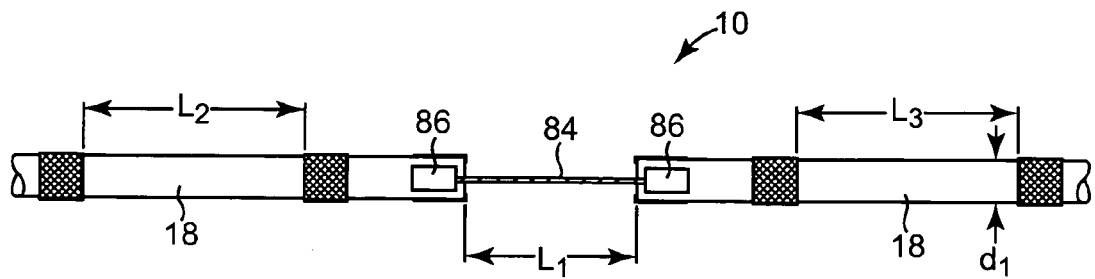
FIGS. 68A-68G are side and cross-sectional views of an ablation apparatus according to one embodiment of the invention.
Figure 68B:
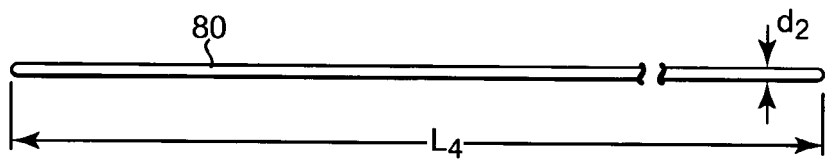
Figure 68C:
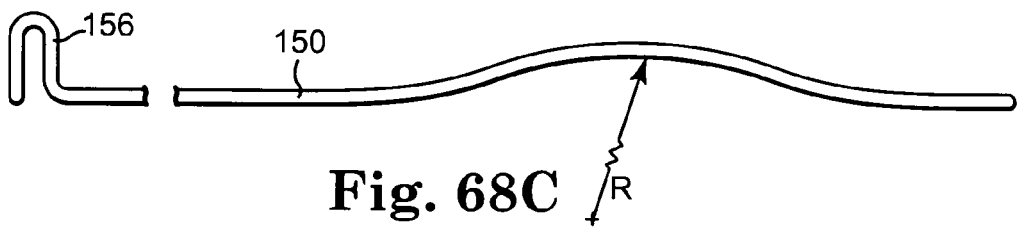
Figure 68E:
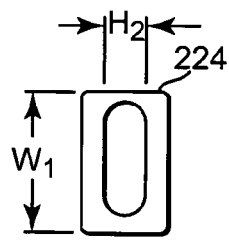
Figure 68D:
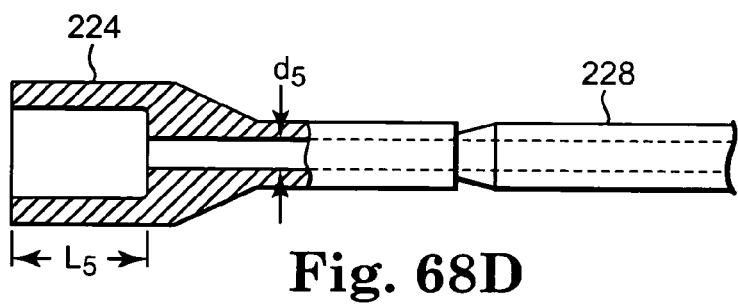
Figure 68F:
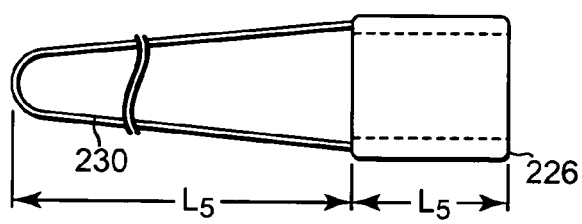
Figure 68G:
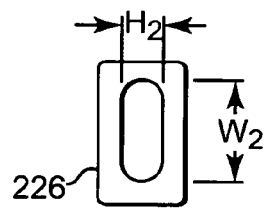

FIGS. 68A-68G illustrate an embodiment of the ablation apparatus 10 including adapters 86 constructed of a copper cylinder crimped onto a connecting cable 84. The connecting cable 84, in some embodiments, can have a length $L_1$ of approximately 1.5 cm to 10.5 cm. Tubes 18 of the ablation apparatus 10 can include one of two sizes, such as 21 cm or 31 cm. The tubes 18 can include clamping lengths $L_2$ and $L_3$ of approximately 8 cm. The tubes 18 can include a diameter of approximately 0.25 cm. FIG. 68B illustrates an embodiment of a stiffener 80 for use within the tubes 18 of FIG. 68A. The stiffener 80 can include a length $L_4$ of approximately 10 cm beyond the length of the tubes 18. The stiffener 80 can include a diameter of approximately 0.093 cm. FIG. 68C illustrates an embodiment of a stiffening rod 150 for use with the tubes 18 of FIG. 68A. The stiffening rod 150 can include a C-shaped handle 156, which can provide orientation and means to hold the stiffening rod 150 in the clamping position. The stiffening rod 150 can include a minimum radius R. In some embodiments, the tubes 18 can have an outer diameter of approximately 0.25 cm and an inner diameter of approximately 0.125 cm. FIGS. 68D and 68E illustrate an embodiment of a distal end capture 224 and a pen handle 228. The distal capture 224 can include a height $H_1$ of approximately 0.265 cm, a width $W_1$ of approximately 0.56 cm, and a length $Ll_5$ of approximately 0.5 cm, and a diameter $D_3$ of approximately 0.20 cm. The pen handle 228 can be coupled to the distal end capture 224. FIGS. 68F and 68G illustrate an embodiment of a proximal end capture 226, including a height $H_2$ of approximately 0.265 cm, a width $W_2$ of approximately 0.56 cm, a first length $L_6$ of approximately 0.8 cm, and a second length $L_7$ of approximately 7 cm. The length $L_7$ can include a proximal loop 230 coupled to the proximal end capture 226. In some embodiments, the distal end capture 224 can be constructed of Delin®.

Figure 69A:
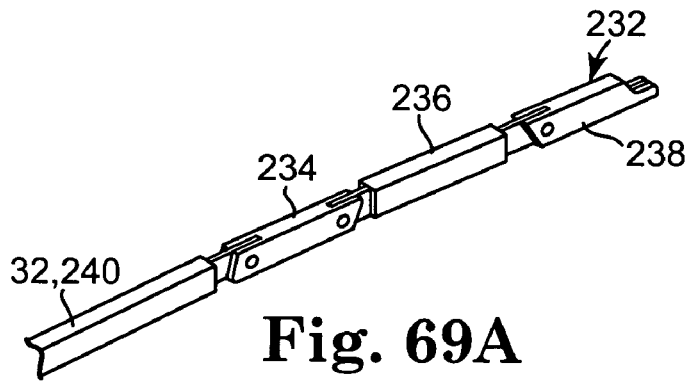
FIGS. 69A-69C are perspective and side views of an ablation apparatus according to one embodiment of the invention.
Figure 69B:
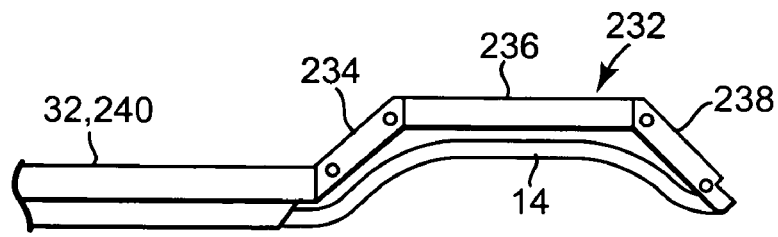
Figure 69C:
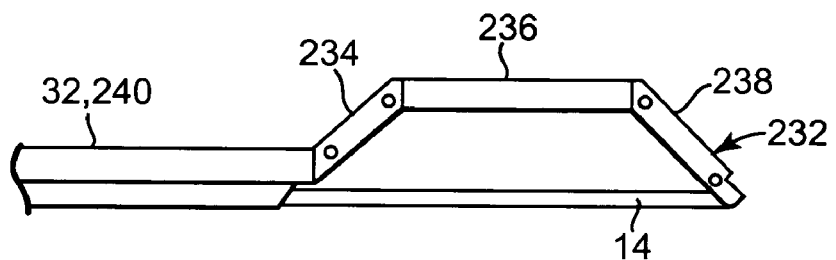

FIGS. 69A-69C illustrate an embodiment of an ablation apparatus including a link assembly 232. As shown in FIG. 69A, the link assembly 232 can include a first segment 234, a second segment 236, and a third segment 238. The link assembly 232 can be coupled to a suitable handle 240 and/or an insertion tool 32. The first, second, and third links, 234, 236, and 238 can be coupled to one another with links and pins, or any other suitable arrangement. The link assembly 232 can also include a wire, for example a Nitinol wire, as a backbone along its length. FIG. 69B illustrates the link assembly 232 in its deployed and inactivated position in which the electrode 14 is substantially loose. FIG. 69C illustrates the link assembly 232 in its deployed and activated position in which the electrode 14 is substantially tensioned in order to clamp the pulmonary veins.

Figure 70:
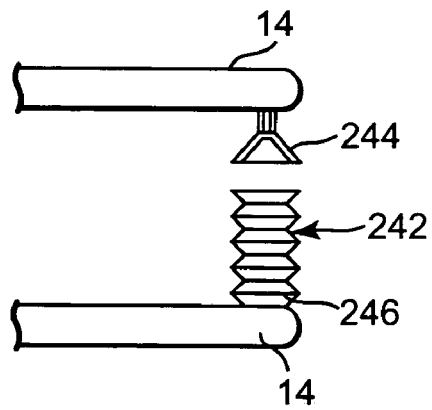
FIG. 70 is a side view of an ablation apparatus according to one embodiment of the invention.

FIG. 70 illustrates an embodiment of an electrode 14 including a vacuum distal clamping assist device 242. The vacuum distal clamping assist device 242 can include a cone-shaped member 244 and an accordion-shaped member 246.

Figures 71A, 71B:
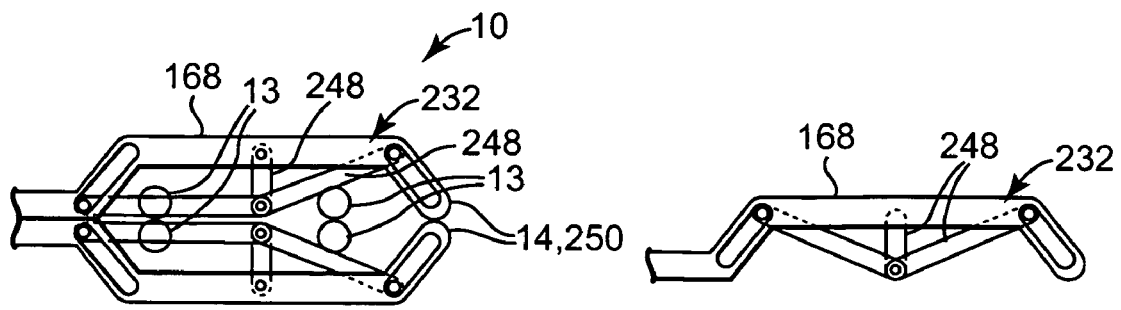
FIGS. 71A-71B are side views of an ablation apparatus according to one embodiment of the invention.

FIGS. 71A and 71B illustrate an embodiment of the ablation apparatus including a link assembly 232. The link assembly 232 can include a clamp frame 168 and several links 248. The link assembly 232 can also include notches 250 that can receive electrodes 14.

Figure 72A:
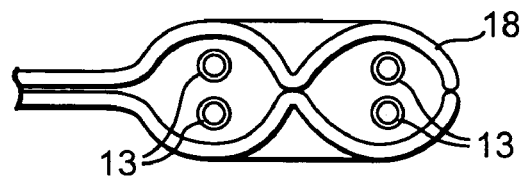
FIGS. 72A-72B are side and perspective views of an ablation apparatus according to one embodiment of the invention.
Figure 72B:
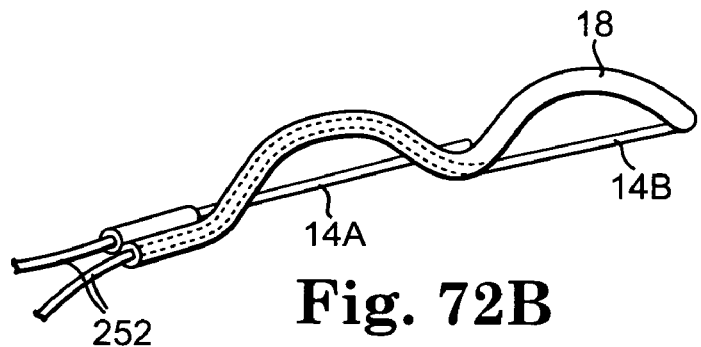

FIGS. 72A and 72B illustrate an embodiment of the ablation apparatus 10 including tubes 18 that can include a semi-rigid or rigid pre-bent geometry. As shown in FIG. 72B, the ablation apparatus 10 can include a proximal electrode 14A and an internal stiffening cable. The ablation apparatus 10 can also include a distal electrode 14B, also with an internal stiffening cable. The internal stiffening cables 252 can be pulled in order to create tension to make the electrodes 14A and 14B rigid.

Figure 73:
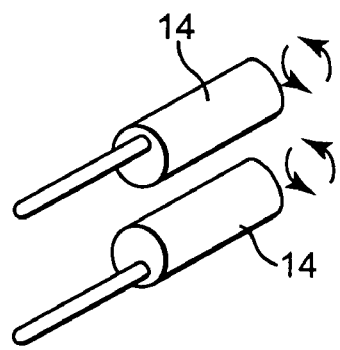
FIG. 73 is a perspective view of a cam electrode for use with an ablation apparatus according to one embodiment of the invention.

FIG. 73 illustrates an embodiment of electrodes having a cam shape. The cam shape can include an oval cross-sectional profile with a rod attached to the oval at an off center position. The cam electrodes 14 can be rotated approximately 180 degrees, in some embodiments, in order to put pressure on the pulmonary veins 13 or to relieve pressure off of the pulmonary veins 13.

Figure 74A:
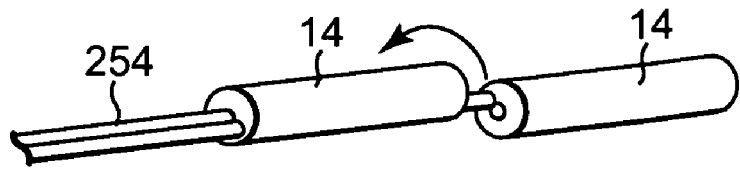
FIGS. 74A-74C are perspective views of a cam electrode for use with an ablation apparatus according to one embodiment of the invention.
Figure 74B:
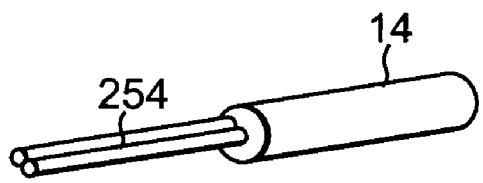
Figure 74C:
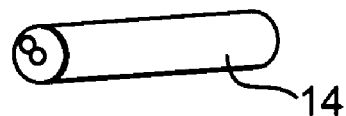

FIGS. 74A and 74B illustrate another embodiment of a cam-shaped electrode 14. The cam-shaped electrode 14 can be coupled to a placement rod 254, which can include a keyed cross-sectional profile. The keyed cross-sectional profile of the placement rod can mate with a keyed recess within one or more electrodes 14 in order to rotate the cam electrodes 14.

Figure 75:
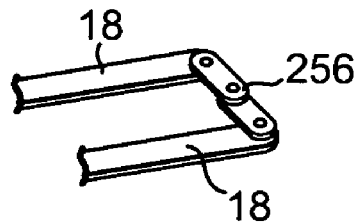
FIG. 75 is a perspective view of a distal hinge for use with an ablation apparatus according to one embodiment of the invention.

FIG. 75 illustrates an embodiment of a distal hinge 256 that can be coupled to tubes 18. The distal hinge can include two lengths.

FIGS. 76A-76E illustrate an embodiment of an ablation apparatus 10 including a distal electrode 14A, a proximal electrode 14B, a loop 260, a delivery tether 262, one or more paddles 264, a ball 266, and a socket 268. The loop 260 can be positioned around one or more sets of pulmonary veins 13. The distal electrode 14A can be coupled to the loop via a lumen 50. The distal electrode 14A can be moved along the loop 260 into position with respect to the pulmonary veins 13. The proximal electrode 14B can also be moved toward the pulmonary veins 13 after being disengaged from an insertion tool 32 by removing the ball 266 from the socket 268. The proximal electrode 14B can be moved toward the pulmonary veins 13 using the delivery tether 262, for example, by pulling the paddles 264. The distal electrode 14A and the proximal electrode 14B can each be connected to a conductor 16 in order to provide energy to the electrodes 14A and 14B. The distal electrode 14A and the proximal electrode 14B can each also be connected to a ground 258. The ball 266 and the socket 268 can be omitted in some embodiments, such as the embodiment shown in FIG. 76A, including the delivery tether 262 being coupled directly to the proximal electrode 14B. FIG. 76E illustrates an embodiment of a pin 270 used to connect the insertion tool 32 to the proximal electrode 14B via the loop 260. FIG. 76C illustrates an alternative embodiment of tubes 18 that can be used rather than the loop 260. The tubes 18 of FIG. 76C can include a diagonal crossing configuration. FIG. 76D illustrates an embodiment of the proximal electrode 14B including two recesses that can receive the loop 260.

FIG. 77 illustrates an embodiment of electrodes 14, including a first jaw 272, a second jaw 274, a clamp 276, and a spring 278. The first jaw 272 can be coupled to the second jaw 274 via the clamp 276. The spring 278 can be coupled to the first jaw 272. In one embodiment, the spring 278 can have a square cross-section in order to provide a particular orientation. FIG. 78 illustrates an insertion tool 32 coupled to a tube 18 and a blunt tip 280. The tube 18 can be comprised of a pre-curved wire that can be bent approximately 180 degrees.

FIG. 79 illustrates an embodiment of the ablation apparatus 10 including a distal electrode 14A and a proximal electrode 14B. The distal electrode 14A and the proximal electrode 14B can be coupled to one another with square supports that can be received within correspondingly-shaped square recesses. The supports 282 and the recesses 284 can have other suitable shapes such as triangular, hexagonal, or circular shapes. The supports 282 can be connected to the distal electrode 14A and the proximal electrode 14B in order to substantially surround the pulmonary veins 13.

Figure 80B:
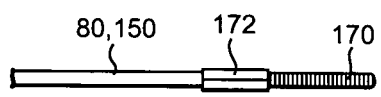
FIGS. 80A-80E are side, cross-sectional, and schematic views of ablation apparatuses according to some embodiments of the invention.
Figure 80A:
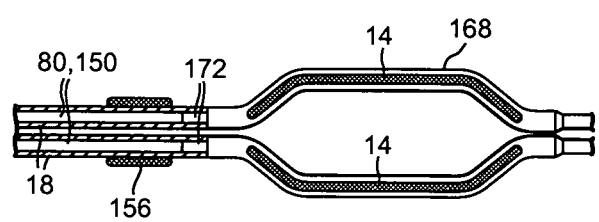
Figure 80D:
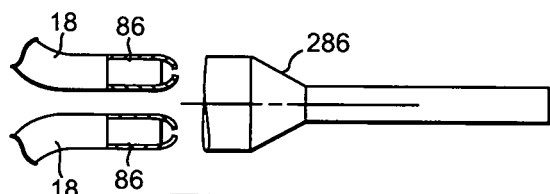
Figure 80C:
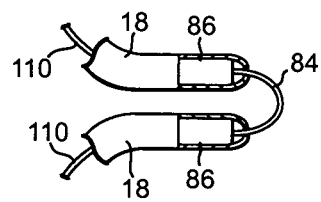
Figure 80E:
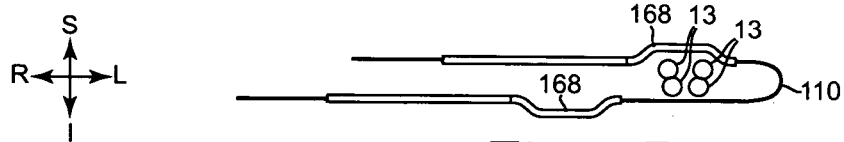

FIGS. 80A-80E illustrate an ablation apparatus 10 including electrodes 14, tubes 18, stiffening members 80, or stiffening rods 150, a proximal capture 156, a clamp frame 168, hexagonal or square portions 172, and flexible guide wires 170. FIG. 80D illustrates a distal capture device 286 for use in capturing ends of the tubes 18. FIG. 80C illustrates tubes 18 through which guide wires 110 can be threaded, and a connecting cable 84 that can couple two adapters 86 together. The adapters 86 can include blunt tips, in some embodiments. FIG. 80E illustrates the guide wire 110 positioned around the pulmonary veins 13 with two separate clamp frames 168 being slid along the guide wire 110 in order to place the clamp frame 168 adjacent the pulmonary veins 13. The clamp frames 168 and the tubes 18 can include a secondary channel that can receive the guide wire 110. In this manner, the ablation apparatus 10 of FIGS. 80A-80E can be inserted through a right side of the patient. The guide wires 110 and/or the connecting cable 84 can be pulled tight by the distal capture device 286 in order to secure the ends of the tubes 18 together. The connecting cable 84 can be constructed of a non-compressible material in order to hold the connecting cable tight. In one embodiment, the tubes can include a 3/16 inch inner diameter and a 5/16 inch outer diameter. In one embodiment, the stiffener 80 and/or the stiffening rods 150 can include a diameter of approximately 0.093 cm, and the hexagonal or square drive can be a 3/32 inch hexagonal component. In one embodiment, the clamp frame 168 can include a diameter of approximately 8 mm. In one embodiment, the electrodes 14 can include a width of approximately 0.15 cm.

Figure 81:
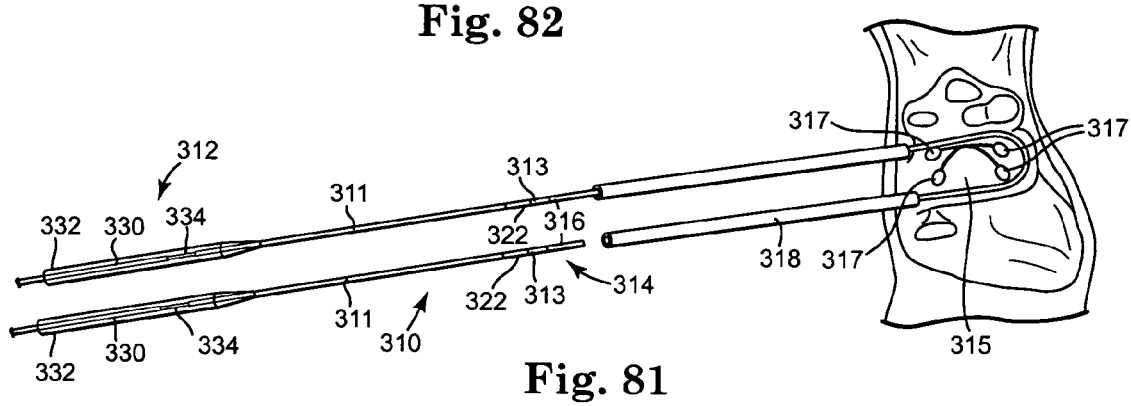
FIG. 81 is a perspective view of a loop ablation device according to one embodiment of the invention positioned around the pulmonary veins.
Figure 95:
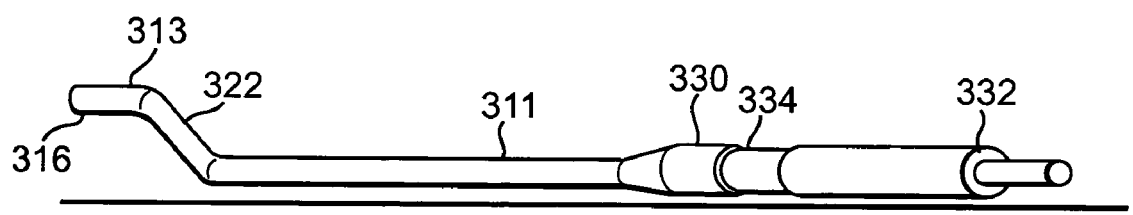
FIG. 95 is a side perspective view of an electrode with a curved tip and a handle end of the loop ablation device of FIG. 83.
Figure 96:
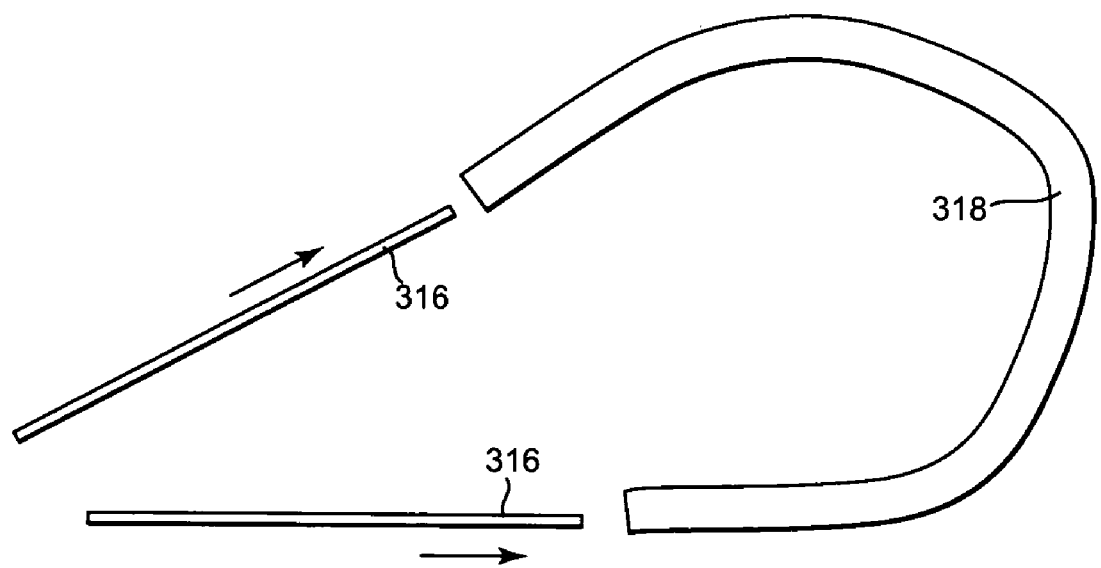
FIG. 96 is a schematic illustration of electrodes and a cannula for use in one embodiment of the invention.

FIG. 81 illustrates a loop ablation device 310 according to one embodiment of the invention. The loop ablation device 310 can include one or more electrode rods 311. As shown in FIGS. 81 and 95, the electrode rods 311 can each include a handle portion 312, a curved tip 313, a jaw 314, one or more electrodes 316, and a cam-shaped portion 322. The handle portions 312 of the electrode rods 311 can be used to rotate the curved tips 313 in order to bring the electrodes 316 closer to one another and close the jaws 314 around target tissue 315. In some embodiments, the loop ablation device 310 can include two electrodes 316 for bipolar ablation. The two electrodes 316 can be coupled to two electrode rods 311 that can be extended around the pulmonary veins 317 through a cannula 318. FIG. 96 is a schematic illustration of the cannula 318 receiving the electrodes 316. In some embodiments, the cannula 318 can be constructed of a weeping polymer, such as expanded polytetrafluoroethylene (ePTFE), in order to provide saline or other liquid to the target tissue 315. Saline or liquid can be provided to the cannula 318 to surround the electrodes 316 in order to conduct ambulatory energy through micropores in the weeping polymer and onto the target tissue 315.

As shown in FIGS. 83-90, the loop ablation device 310 can include a rotating grasping mechanism 320 coupled to the handle portions 312 of the electrode rods 311. The rotating grasping mechanism 320 can position the electrodes 316 in a particular spaced relation. The rotating grasping mechanism 320 can be used to manipulate the curved tips 313 of the electrode rods 311 to grasp and clamp the tissue while the cam-shaped portions 322 can cause the electrodes 316 to roll up onto the pulmonary veins 317 and onto the target tissue 315 of the atrium.

Figure 83:
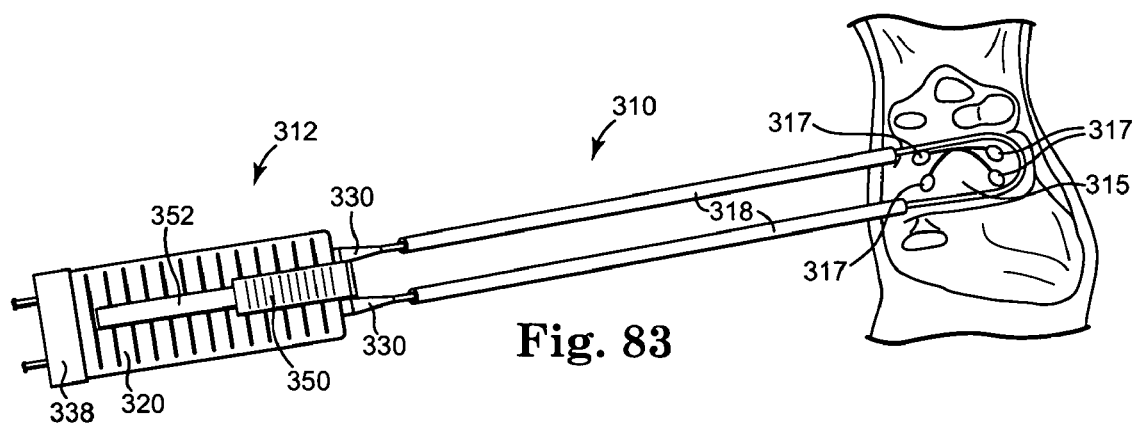
FIG. 83 is a top perspective view of the loop ablation device of FIG. 82 positioned around the pulmonary veins and including a handle.

As shown in FIG. 81, the cannula 318 can be positioned in the patient's body, such as around the pulmonary veins 317. When the cannula 318 has been placed in the body, the electrode rods 311 can be inserted into the cannula 318. As shown in FIG. 83, the electrode rods 311 can be placed along the pulmonary veins 317 with the cam-shaped portions 322 adjacent the intersection of the pulmonary veins 317 and the walls of the heart. It can be appreciated that this approach may occlude blood flow into the heart through one set of pulmonary veins while preserving blood flow through the other set of pulmonary veins.

Figure 82:
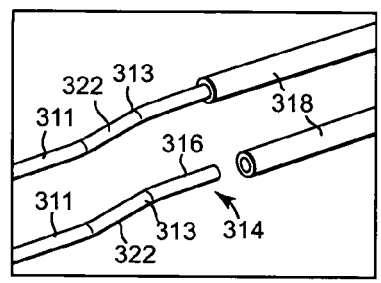
FIG. 82 is a perspective view of electrodes and a cannula for use with the loop ablation device of FIG. 81.
Figure 94:
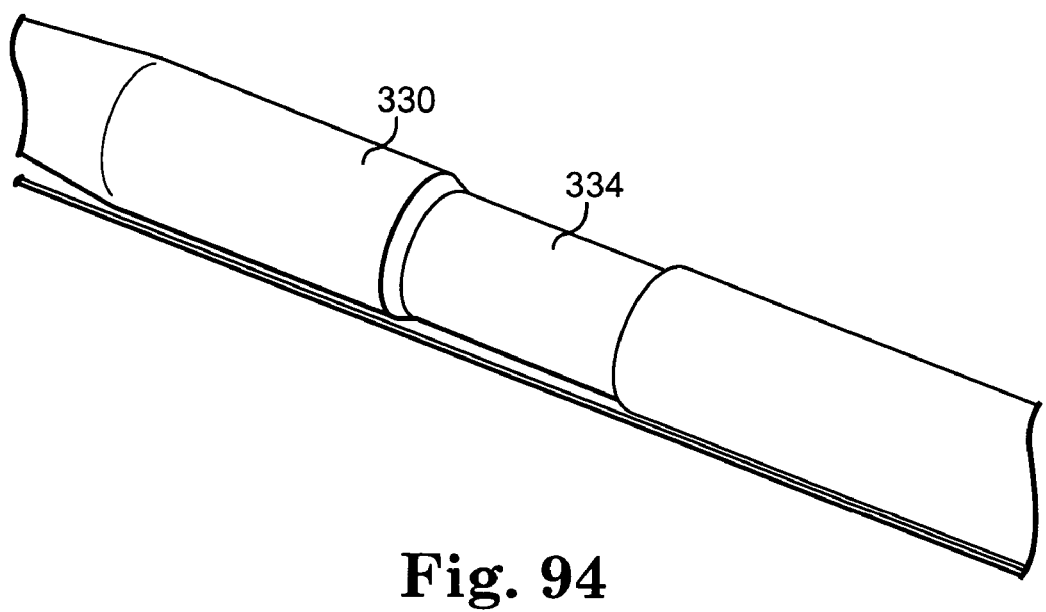
FIG. 94 is a side perspective view of a handle end of the loop ablation device of FIG. 83.

As shown in FIGS. 82 and 95, the electrode rods 311 can include curved tips 313 with cam-shaped portions 322 for engaging the target tissue 315 through the cannula 318. As shown in FIGS. 81 and 95, the electrode rods 311 can also include handle ends 330 substantially surrounded by insulating sleeves 332. The handle ends 330 can also include flats 334 that can be engaged by the rotating grasping mechanism 320. FIG. 94 illustrates a flat 334 of a handle end 330 of an electrode rod 311.

Figure 84:
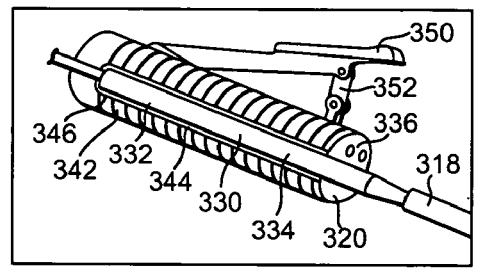
FIG. 84 is a side perspective view of the handle of the loop ablation device of FIG. 83.

As shown in FIG. 84, the rotating grasping mechanism 320 can include two C-shaped clamps 342 for receiving the electrode rods 311. A handle end 330 of an electrode rod 311 can be positioned within a channel 346 of a C-shaped clamp 342 of the rotating grasping mechanism 320. In one embodiment, magnets 344 along the electrode rods 311 can hold the electrode rods 311 in channels 346 of the rotating grasping mechanism 320. The C-shaped clamp 342 can engage the flat 332 of the electrode rod 311. A spaced relation of the electrode rods 311 can be held constant by a center portion 336 of a housing 338 between the electrodes rods 311 of the rotating grasping mechanism 320.

Figure 85:
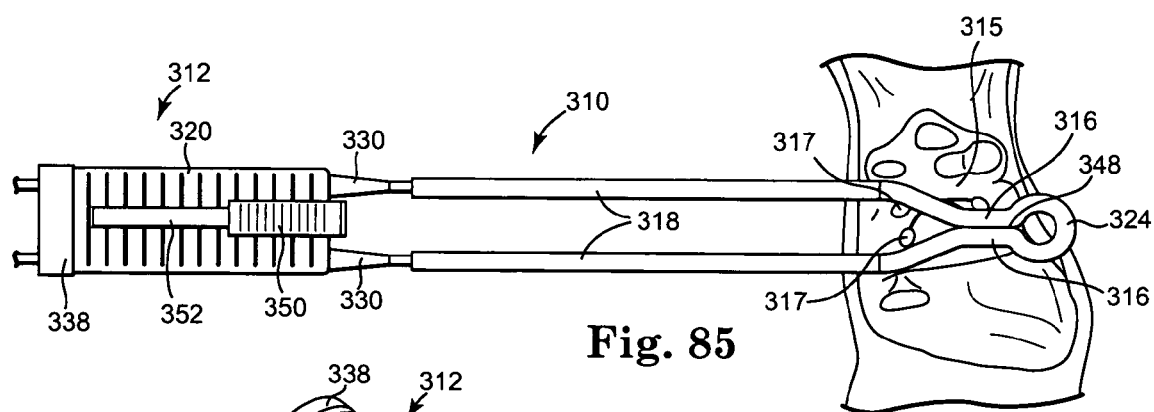
FIG. 85 is a top perspective view of the loop ablation device of FIG. 83 clamped around one set of pulmonary veins.
Figure 86:
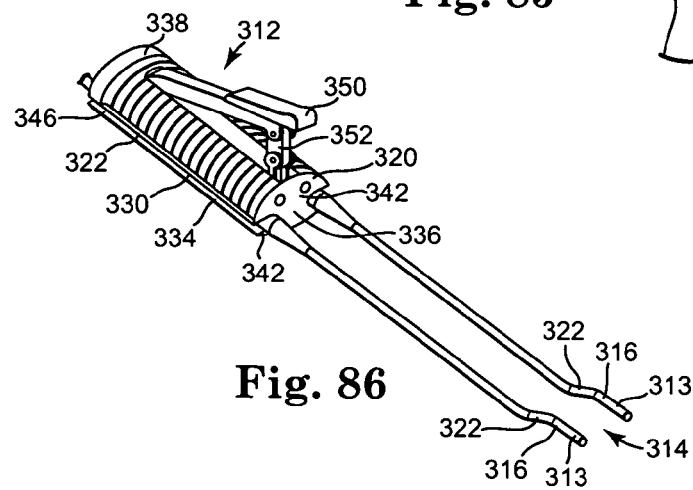
FIG. 86 is a front perspective view of the loop ablation device of FIG. 83.

As shown in FIG. 85, when the electrode rods 311 are fully extended into the cannula 318, the cam-shaped portions 322 can be rotated to create a small loop 324 of cannula 318 between the electrodes 316 that are clamped together for ablating the target tissue 315. As also shown in FIG. 85, a small occlusion 348 can be created in the cannula 318 between the electrodes 316 to prevent electrical cross over through the cannula 318.

Figure 87:
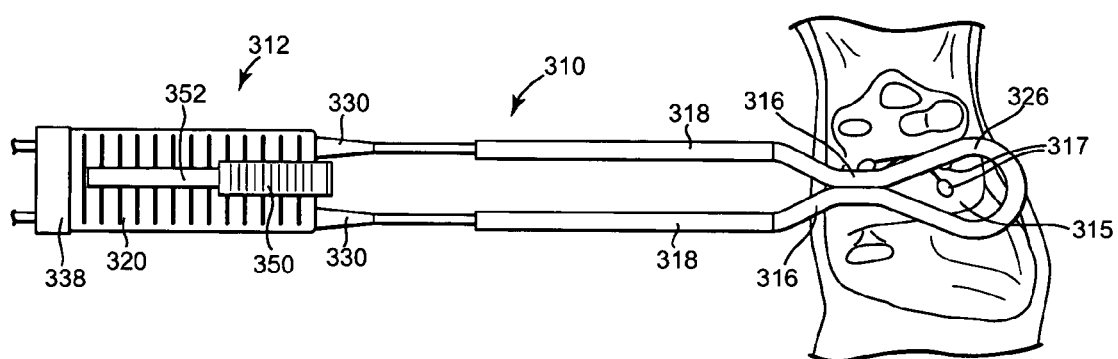
FIG. 87 is a top perspective view of the loop ablation device of FIG. 83 clamped around another set of pulmonary veins.
Figure 88:
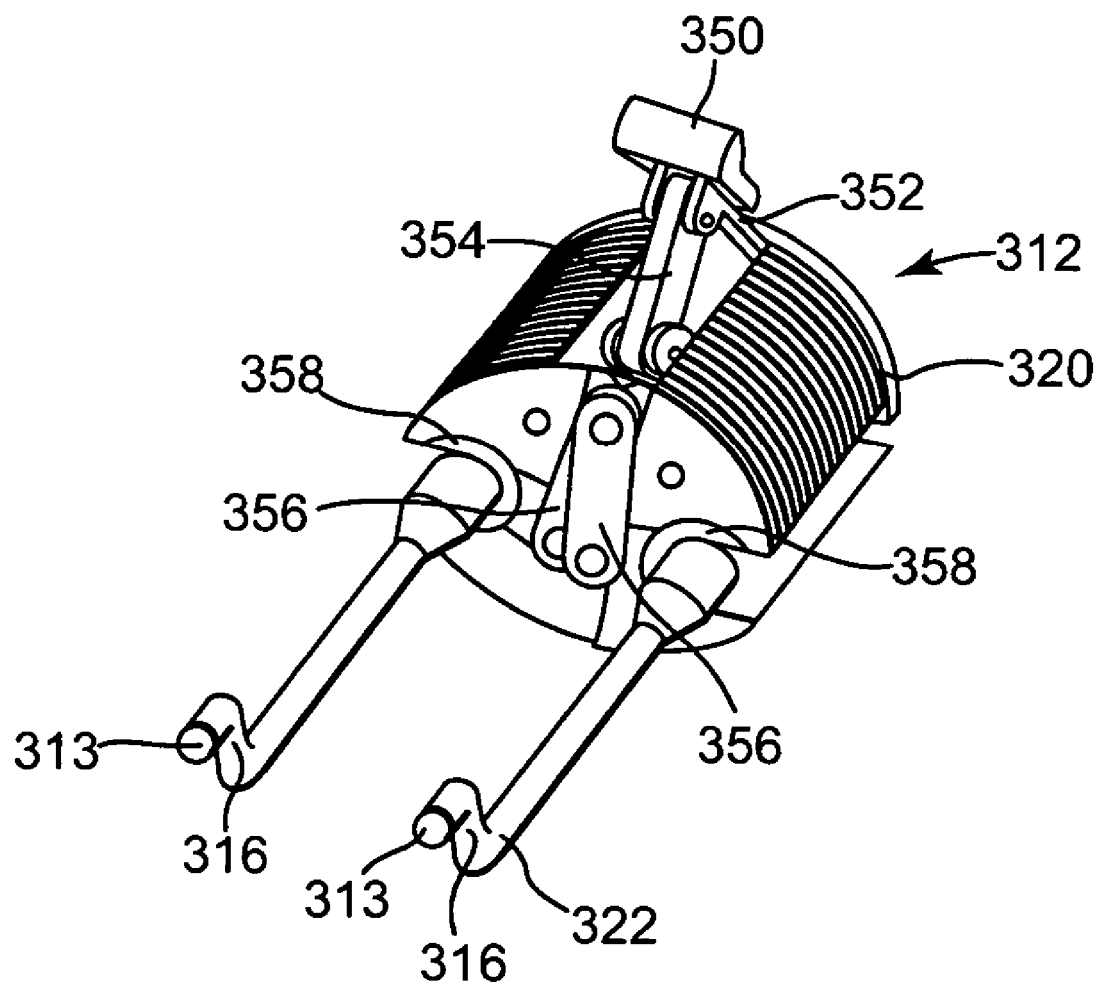
FIG. 88 is an end perspective view of the loop ablation device of FIG. 83.
Figure 89:
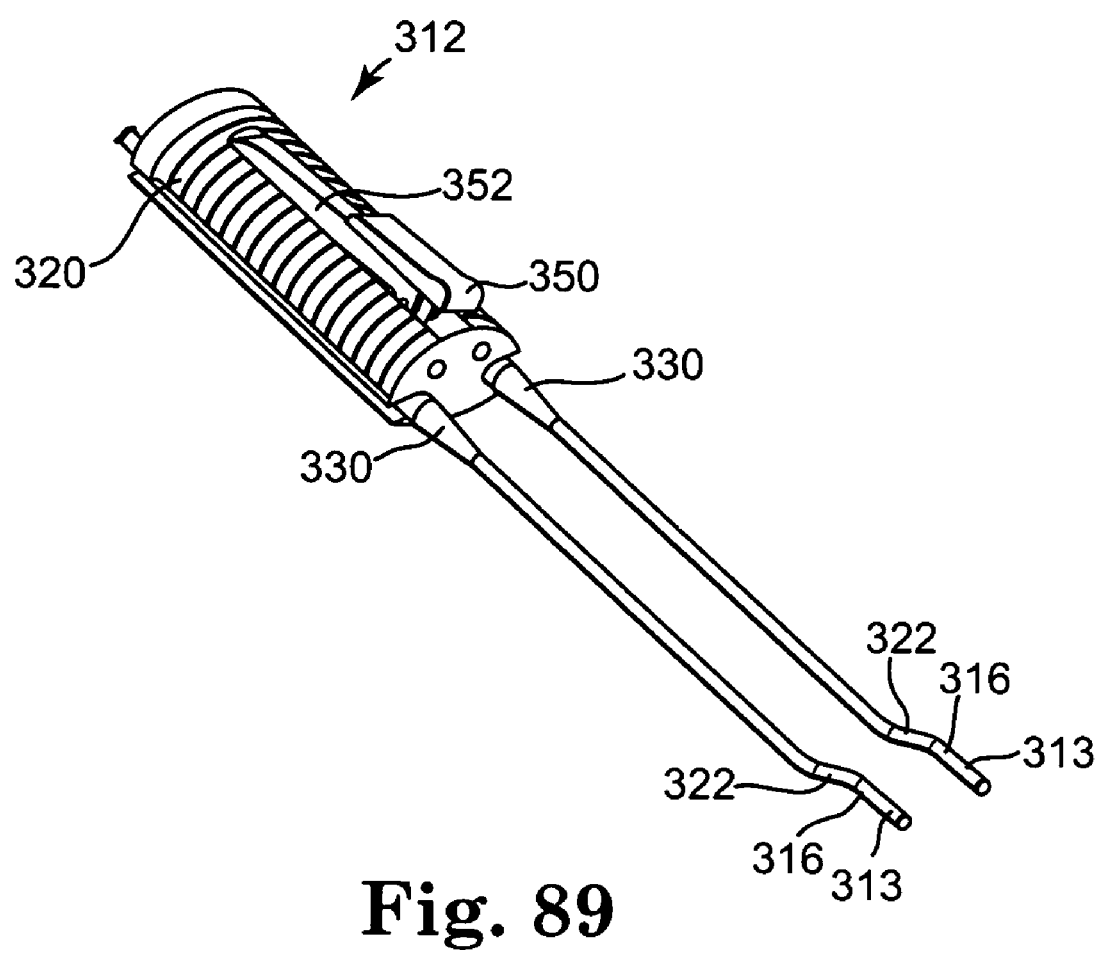
FIG. 89 is a top perspective view of the loop ablation device of FIG. 83.
Figure 90:
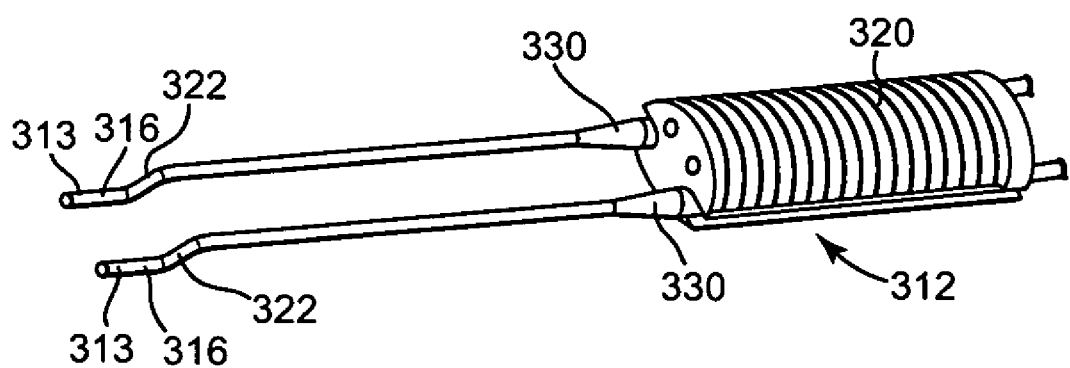
FIG. 90 is another top perspective view of the loop ablation device of FIG. 83.

As shown in FIG. 87, the cannula 318 can be left in place and the electrodes 316 can be moved along the length of the cannula 318 to ablate in a linear fashion a lesion in the target tissue 315 adjacent to the cannula path. A large loop 326 can be formed at the end of the cannula 318 as the electrodes 316 are partially withdrawn from the cannula 318.

Figure 91:
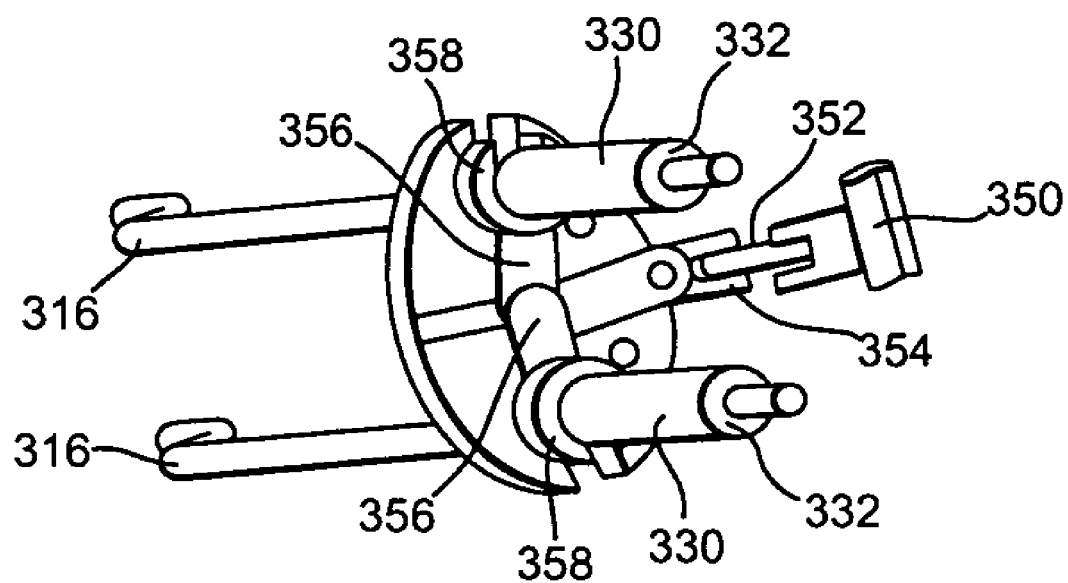
FIG. 91 is an end perspective view of the loop ablation device of FIG. 83 with a housing removed.
Figure 92:
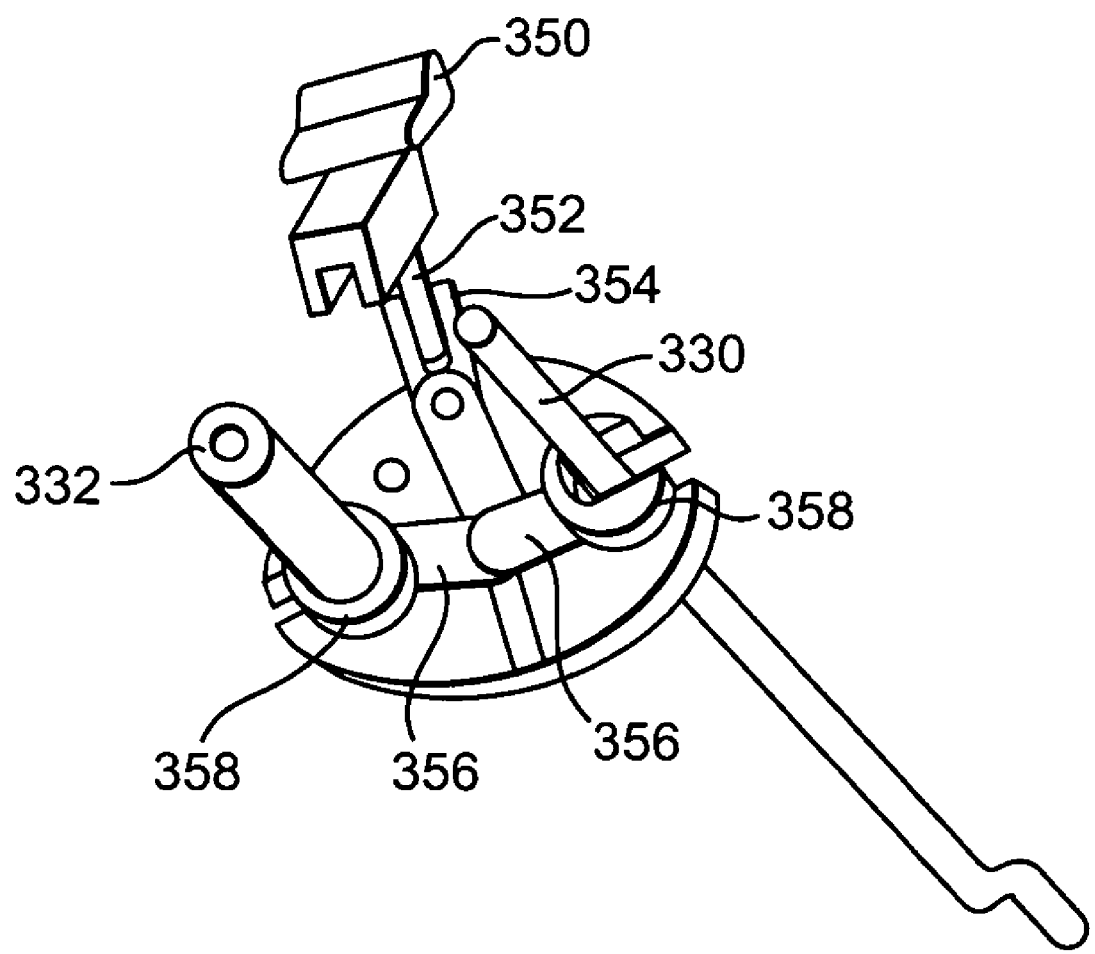
FIG. 92 is another end perspective view of the loop ablation device of FIG. 83 with the housing removed.
Figure 93:
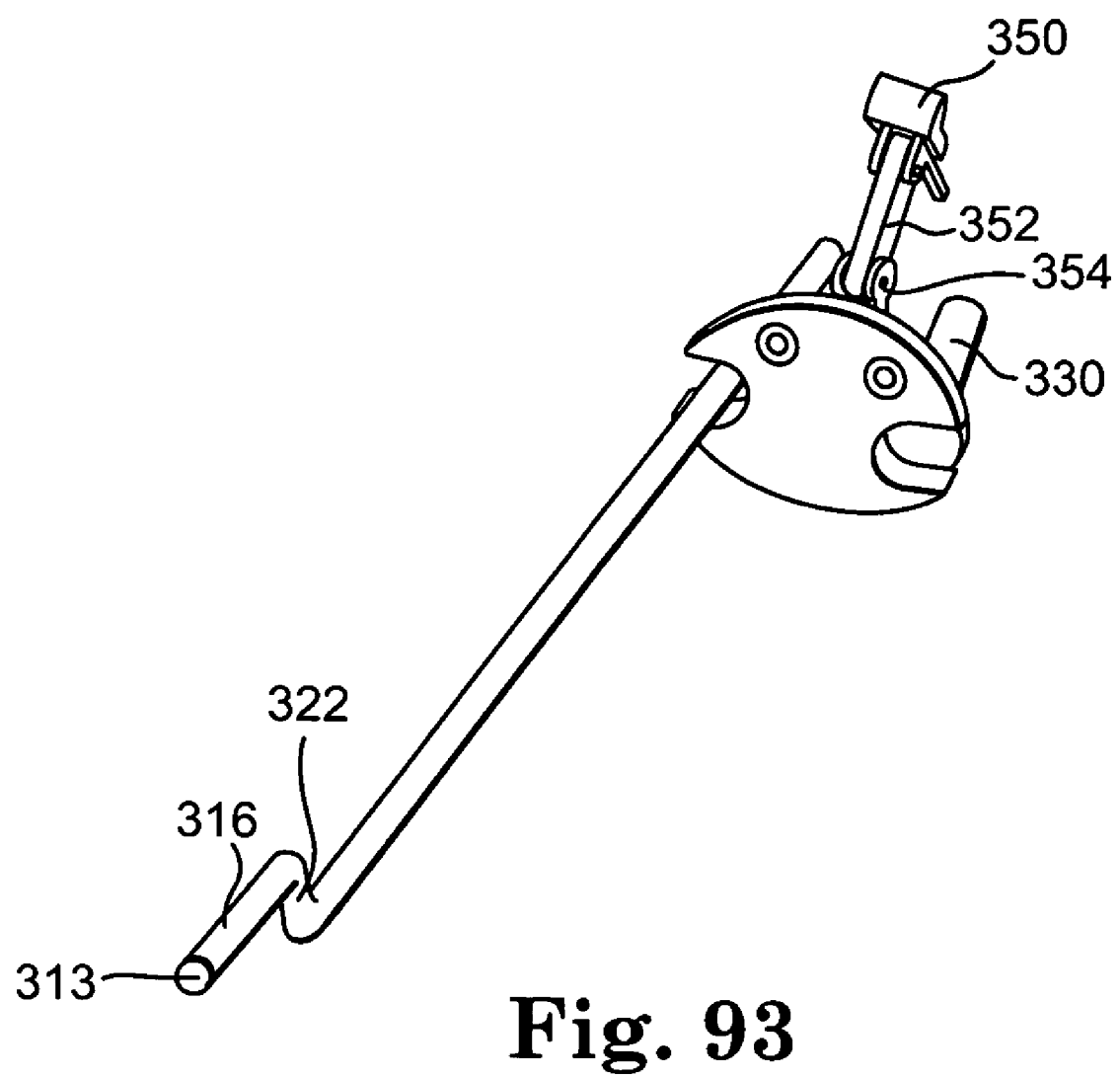
FIG. 93 is yet another end perspective view of the loop ablation device of FIG. 83 with the housing removed.

FIGS. 91-93 illustrate the rotating grasping mechanism 320 with the housing 338 removed. The rotating grasping mechanism 320 can include a cam assembly 349. The cam assembly 349 can include a thumb lever 350, a first linkage 352, a second linkage 354, two L-shaped brackets 356, and two C-shaped collars 358. The first linkage 352 can be rotatably coupled to the second linkage 354 which can be rotatably coupled to the L-shaped brackets 356. The L-shaped brackets 356 can be constructed of a single bracket member or of two links coupled together. The C-shaped collars 358 can be rigidly coupled to or integral with ends of the L-shaped brackets 356. The electrode rods 311 can be rigidly secured within the C-shaped collars 358. When a surgeon presses the thumb lever 350, the first linkage 352 can rotate the second linkage 354. The second linkage 354 can move the L-shaped brackets 356 in order to rotate the C-shaped collars 358 and the electrode rods 311.

In some embodiments, the loop ablation device 310 can be used to ablate target tissue 315 on a beating heart. In some embodiments, the loop ablation device 310 and the cannula 318 can be inserted into the patient's body through a single thoracotomy (such as a small right thoracotomy) and a limited number of ports (such as less than five ports on both the left and right side of the patient), without having to perform a sternotomy. In some embodiments, the loop ablation device 310 can bioelectrically isolate the pulmonary veins 317 from the left atrium by ablating a transmural continuous lesion surrounding the pulmonary veins 317. In some embodiments, the loop ablation device 310 can be positioned by a surgeon with two hands but can be actuated by the surgeon to ablate the target tissue 315 using only one hand. In one embodiment, no more than fifty percent of the left atrium is occluded at any time during the procedure so that the patient's hemodynamics are generally not compromised.

Various features and advantages of the invention are set forth in the following claims.

The invention claimed is:

1. A loop ablation device for ablating target tissue adjacent pulmonary veins of a patient, the loop ablation device comprising:
    a cannula capable of being advanced around the pulmonary veins to form a loop, the loop including first ends and a second end, the cannula being adapted to receive a liquid;
    at least two electrode rods carrying at least two bipolar electrodes, the at least two electrode rods being capable of being advanced through the first ends toward the second end of the loop and toward the target tissue, the at least two bipolar electrodes being adapted to receive energy to ablate the target tissue, the at least two bipolar electrodes being adapted to be surrounded by the liquid within the cannula while ablating the target tissue; and
    a rotating grasping mechanism coupled to the at least two electrode rods, the rotating grasping mechanism rotating the at least two electrode rods within the cannula.

2. The loop ablation device of claim 1 wherein the at least two electrode rods include at least one of curved tips and cam-shaped portions.

3. The loop ablation device of claim 2 wherein the device includes a earn assembly, wherein the cam assembly rotates the at least two electrodes so that the loop substantially rolls off of the pulmonary veins onto the target tissue adjacent at least one of the curved tips and the cam-shaped portions.

4. The loop ablation device of claim 1 wherein the cannula is constructed of a material including expanded polytetrafluoroethylene.

5. The loop ablation device of claim 1 wherein the at least two electrode rods include handle ends and insulating sleeves.

6. The loop ablation device of claim 1 wherein the rotating grasping mechanism includes C-shaped clamps, and wherein the C-shaped clamps include channels that receive the at least two electrode rods.

7. The loop ablation device of claim 1 wherein the at least two bipolar electrodes receive at least one of radio frequency energy, thermal energy, and radiation energy.

8. The loop ablation device of claim 1 wherein the liquid includes saline.

9. The loop ablation device of claim 1 wherein the rotating grasping mechanism includes a cam assembly with a thumb lever that can be used to rotate the at least two electrodes.

10. A loop ablation device for ablating target tissue adjacent pulmonary veins of a patient, the loop ablation device comprising:
    a cannula capable of being advanced around the pulmonary veins to form a loop, the loop including first ends and a second end, the cannula being adapted to receive a liquid;
    at least two electrode rods carrying at least two bipolar electrodes, the at least two electrode rods being capable of being advanced through the first ends toward the second end of the loop and toward the target tissue, the at least two bipolar electrodes being adapted to receive energy to ablate the target tissue, the at least two bipolar electrodes being adapted to be surrounded by the liquid within the cannula while ablating the target tissue;
    a rotating grasping mechanism coupled to the at least two electrode rods, the rotating grasping mechanism rotating the at least two electrode rods within the cannula; and
    wherein C-shaped clamps hold the at least two electrode rods with a magnetic force.

* * * * *